(12) United States Patent
Dougherty et al.

(10) Patent No.: US 9,907,548 B2
(45) Date of Patent: *Mar. 6, 2018

(54) IMPLANT PLACEMENT SYSTEMS, DEVICES AND METHODS

(71) Applicant: Tenjin LLC, Brazoria, TX (US)

(72) Inventors: Christopher P. Dougherty, Rogers, AR (US); Robert A. Van Wyk, St. Pete Beach, FL (US); Gary R. Heisler, Brazoria, TX (US)

(73) Assignee: Tenjin LLC, Brazoria, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/429,527

(22) Filed: Feb. 10, 2017

(65) Prior Publication Data
US 2017/0150960 A1 Jun. 1, 2017

Related U.S. Application Data

(63) Continuation-in-part of application No. 14/972,662, filed on Dec. 17, 2015, now Pat. No. 9,795,374,
(Continued)

(51) Int. Cl.
*A61B 17/04* (2006.01)
*A61F 2/08* (2006.01)
(Continued)

(52) U.S. Cl.
CPC ...... *A61B 17/0401* (2013.01); *A61B 17/0485* (2013.01); *A61F 2/0805* (2013.01);
(Continued)

(58) Field of Classification Search
CPC ........ A61B 17/0401; A61B 2017/0464; A61B 2017/044; A61B 2017/0409; A61B 2017/0445
See application file for complete search history.

(56) References Cited

U.S. PATENT DOCUMENTS 5,100,417 A 3/1992 Cerier
5,152,765 A 10/1992 Ross
(Continued)

OTHER PUBLICATIONS

Product Brochure for "SpeedBridge™ and SpeedFix™ Knotless Rotator Cuff Repair using the SwiveLock® C and FiberTape®: Surgical Technique", Arthrex, Inc., 2013.
(Continued)

*Primary Examiner* — Katherine M Shi
*Assistant Examiner* — Michael Mendoza
(74) *Attorney, Agent, or Firm* — Chalin A. Smith; Smith Patent, LLC

(57) ABSTRACT

Described herein is a simplified placement system and method for a tissue graft or "suture anchor", threaded, knotless or otherwise, by which a surgeon may introduce one or more sutures into a hole in a boney tissue, apply a precise amount of tension to the sutures to advance a soft tissue graft to a desired location, and then advance the anchor into the bone, preferably while maintaining the requisite pre-determined suture tension and without introducing spin to the suture. The simplified placement system and method of the present invention allows the surgeon to establish the graft position and, while maintaining that position, secure the anchor without changing the suture tension or causing a shift in the graft position and furthermore, when the anchor is threaded, without spinning of the suture. In certain preferred embodiments, the distal end of the device includes a resiliently deformable polymeric distal element, optionally including a "split" suture-capturing loop, that allows for the retention of multiple sutures. In other embodiments, the distal end may further include a depth or penetration-limiting element formed of a suitable metallic or polymeric material that serves to prevent the distal end of the device from excessively penetrating, damaging or tearing a tissue graft of interest.

32 Claims, 67 Drawing Sheets

Related U.S. Application Data which is a continuation of application No. 14/636,389, filed on Mar. 3, 2015, now Pat. No. 9,226,817, application No. 15/429,527, filed on Feb. 10, 2017, which is a continuation-in-part of application No. 15/012,060, filed on Feb. 1, 2016, now Pat. No. 9,566,060.

(60) Provisional application No. 61/966,744, filed on Mar. 3, 2014, provisional application No. 61/998,391, filed on Jun. 26, 2014, provisional application No. 61/998,766, filed on Jul. 7, 2014, provisional application No. 61/999,405, filed on Jul. 26, 2014, provisional application No. 62/125,745, filed on Jan. 30, 2015, provisional application No. 62/177,263, filed on Mar. 9, 2015, provisional application No. 62/230,682, filed on Jun. 11, 2015, provisional application No. 62/284,151, filed on Sep. 21, 2015.

(51) Int. Cl.
*A61B 17/06* (2006.01)
*A61B 17/00* (2006.01)
*A61B 90/00* (2016.01)

(52) U.S. Cl.
CPC ......... *A61F 2/0811* (2013.01); *A61B 17/0482* (2013.01); *A61B 17/06061* (2013.01); *A61B 2017/00305* (2013.01); *A61B 2017/00309* (2013.01); *A61B 2017/00314* (2013.01); *A61B 2017/00353* (2013.01); *A61B 2017/00477* (2013.01); *A61B 2017/044* (2013.01); *A61B 2017/0409* (2013.01); *A61B 2017/0412* (2013.01); *A61B 2017/0445* (2013.01); *A61B 2017/0458* (2013.01); *A61B 2017/0464* (2013.01); *A61B 2017/0496* (2013.01); *A61B 2090/064* (2016.02); *A61F 2002/0841* (2013.01); *A61F 2002/0858* (2013.01); *A61F 2002/0888* (2013.01)

(56) References Cited

U.S. PATENT DOCUMENTS

| | | |
|---|---|---|
| 5,217,486 A | 6/1993 | Rice |
| 5,466,243 A * | 11/1995 | Schmieding ....... A61B 17/0485 606/104 |
| 5,584,860 A | 12/1996 | Goble |
| 5,690,677 A * | 11/1997 | Schmieding ....... A61B 17/0485 606/104 |
| 5,827,291 A | 10/1998 | Fucci |
| 5,948,000 A | 9/1999 | Larsen |
| 6,544,281 B2 | 4/2003 | El Attrache et al. |
| 6,641,597 B2 | 11/2003 | Burkhart |
| 7,329,264 B2 | 2/2008 | Merves |
| 8,100,942 B1 | 1/2012 | Green et al. |
| 8,435,264 B2 | 5/2013 | Sojka |
| 8,758,367 B2 | 6/2014 | Phillipon |
| 8,814,905 B2 | 8/2014 | Sengun |
| 8,858,596 B2 | 10/2014 | Robison |
| 9,095,331 B2 | 8/2015 | Hernandez |
| 9,226,817 B2 | 1/2016 | Dougherty |
| 9,370,351 B2 | 6/2016 | Sojka |
| 2006/0100627 A1 | 5/2006 | Stone et al. |
| 2009/0306671 A1 | 12/2009 | McCormack et al. |
| 2009/0312795 A1 | 12/2009 | Barbieri |
| 2014/0277128 A1 | 9/2014 | Moore et al. |

OTHER PUBLICATIONS

Product Brochure for "Healix Knotless™ Anchor", DePuy Mitek, Inc., 2012.

"Optimized Sports Medicine Solutions", Parcus Medical, LLC, 2013.

"ReelX STT™ Knotless Anchor System", Stryker® Corporation, 2010.

"PopLok 3.5 & 4.5 MM", ConMed Corporation, 2015.

* cited by examiner

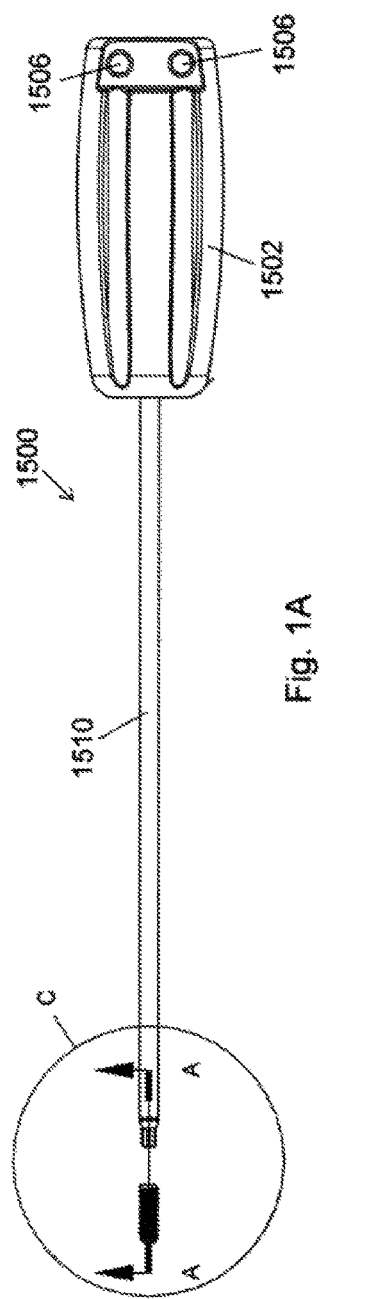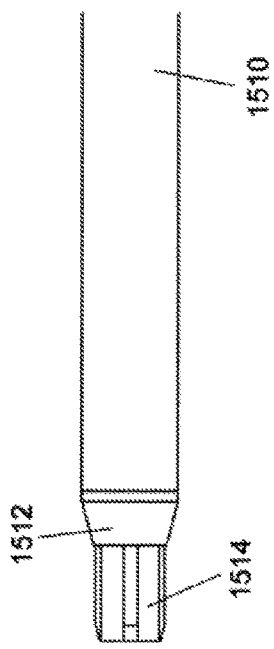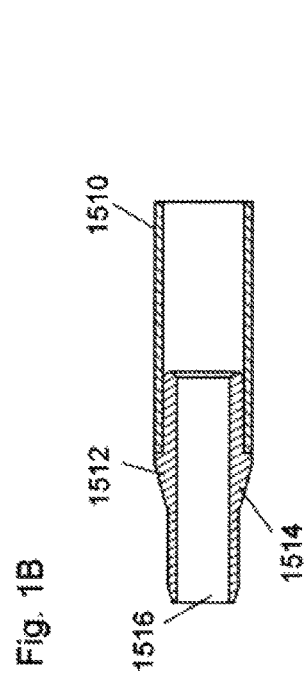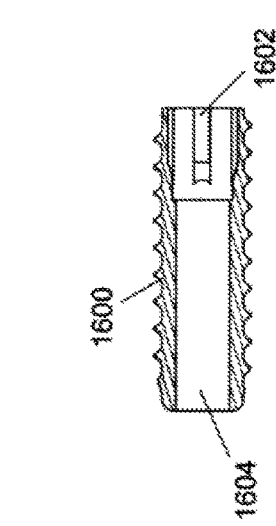
Fig. 1A
Fig. 1B
Fig. 1C

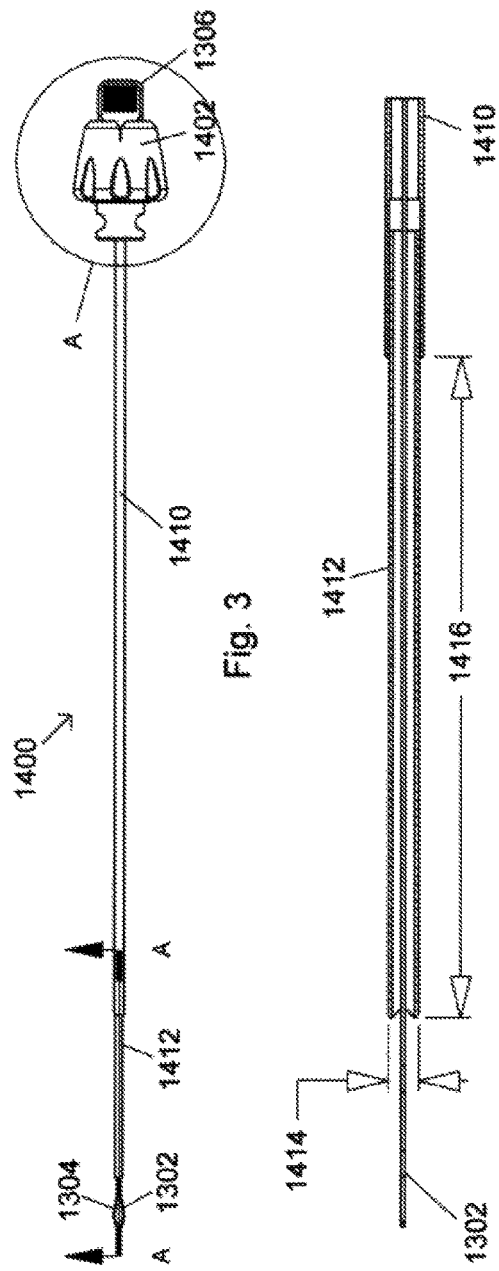
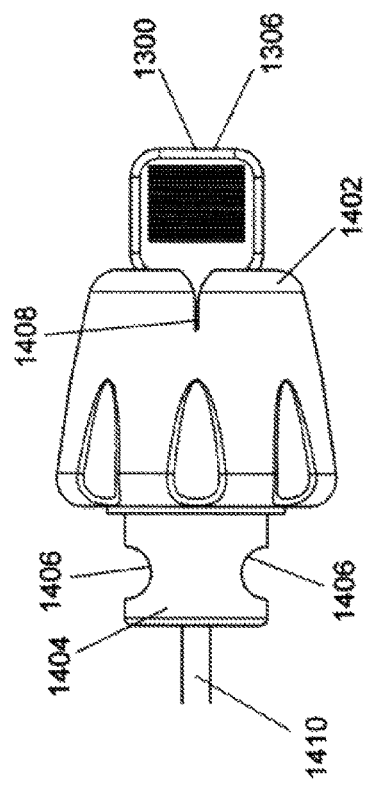

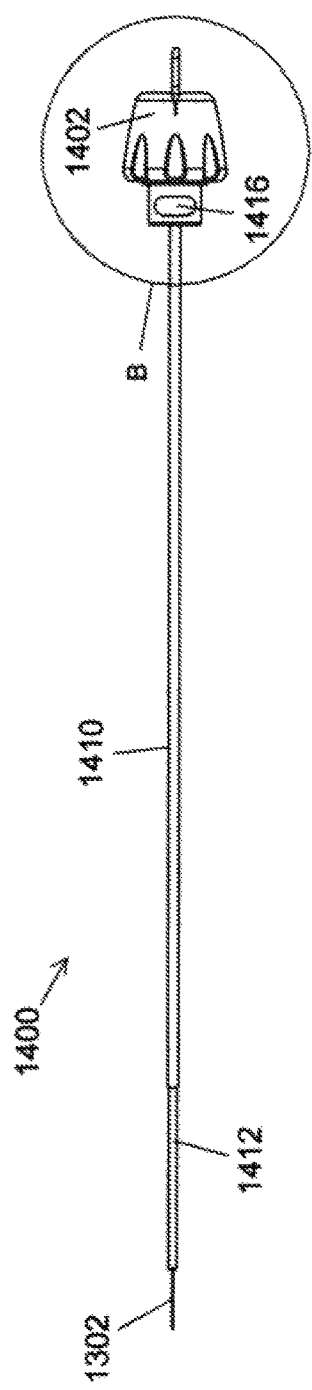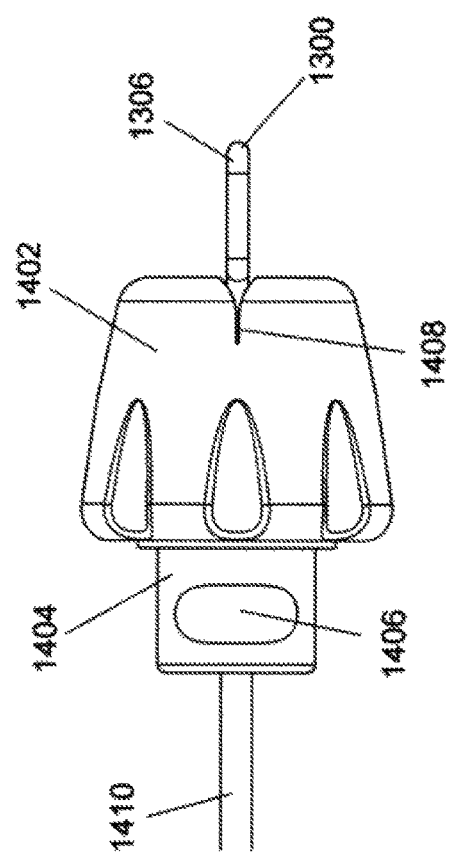

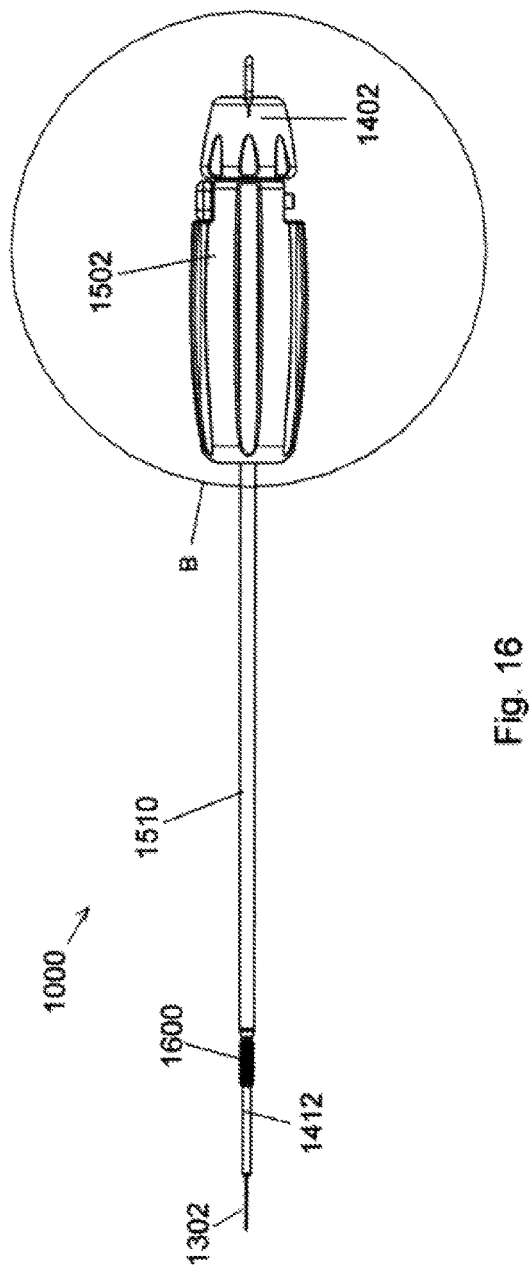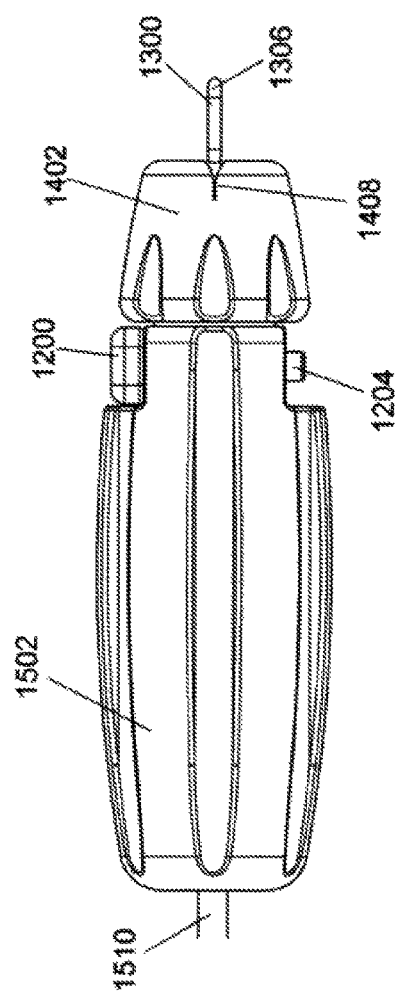
Fig. 16
Fig. 17

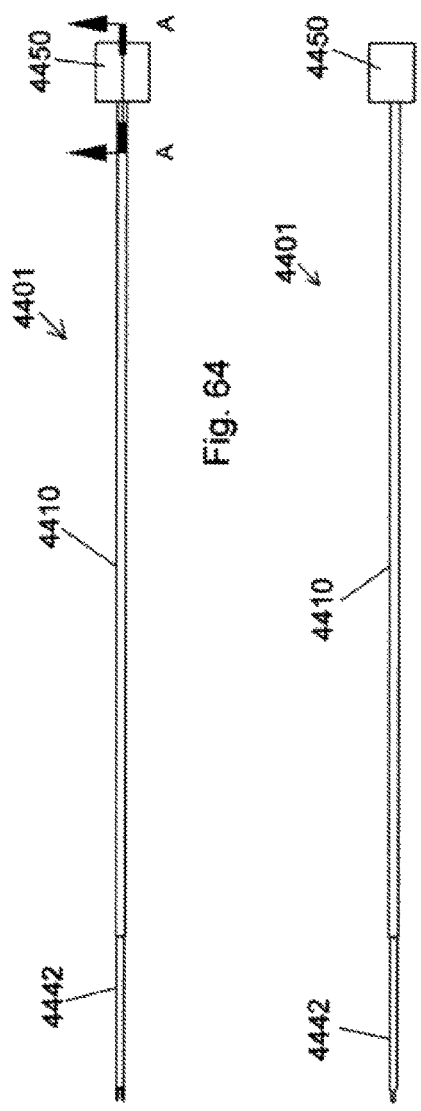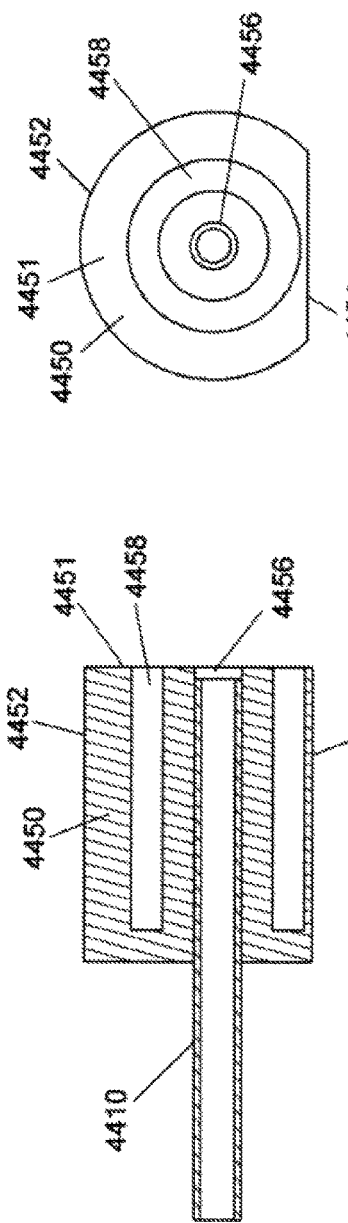

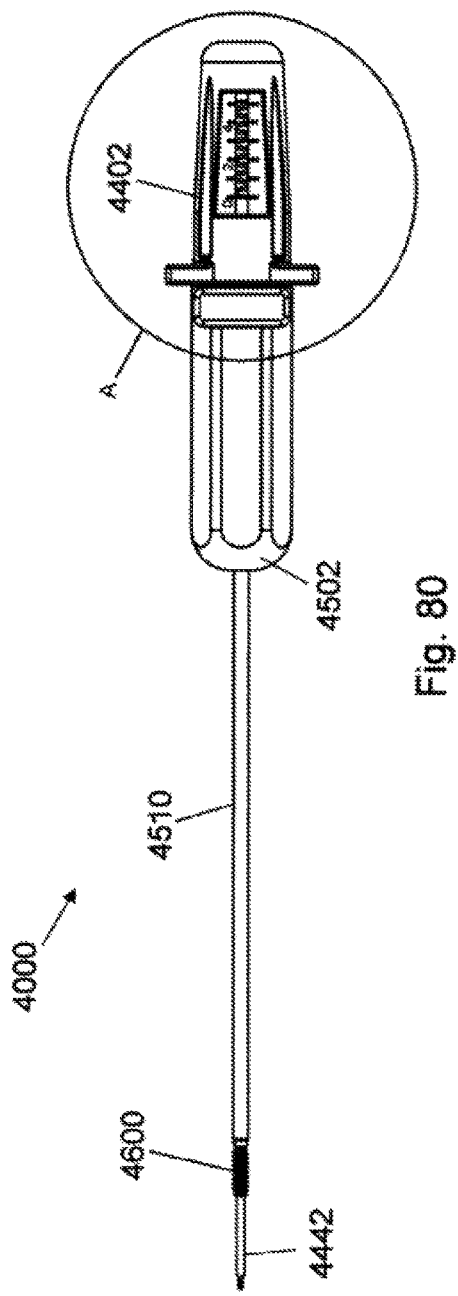
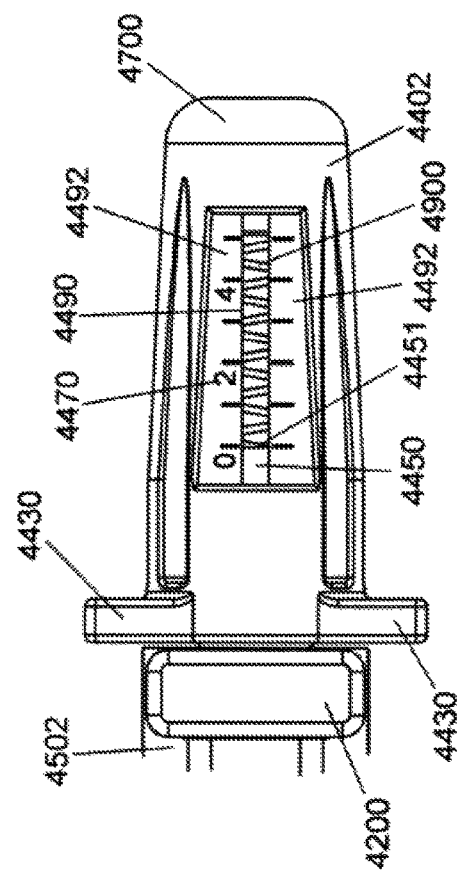
Fig. 80
Fig. 81

IMPLANT PLACEMENT SYSTEMS, DEVICES AND METHODS

PRIORITY

This application is a continuation-in-part of U.S. patent application Ser. No. 14/972,662 filed Dec. 17, 2015, (now U.S. Pat. No. 9,795,374 issued Oct. 24, 2017) which, in turn, is a continuation of U.S. patent application Ser. No. 14/636,389 filed Mar. 3, 2015 (now U.S. Pat. No. 9,226,817 issued Jan. 5, 2016), which, in turn, claims the benefit of U.S. Provisional Application Ser. Nos. 61/966,744 filed Mar. 3, 2014; 61/998,391 filed Jun. 26, 2014; 61/998,766 filed Jul. 7, 2014; and 61/999,405 filed Jul. 26, 2014, the contents of each of which are hereby incorporated by reference in their entirety. This application is also a continuation-in-part of U.S. patent application Ser. No. 15/012,060 filed Feb. 1, 2016, (now U.S. Pat. No. 9,556,060issued Feb. 14, 2017) which, in turn, claims the benefit of U.S. Provisional Application Ser. Nos. 62/125,745 filed Jan. 30, 2015; 62/177,263 filed Mar. 9, 2015; 62/230,682 filed Jun. 11, 2015; and 62/284,151 filed Sep. 21, 2015, the contents of each of which are hereby incorporated by reference in their entirety.

TECHNICAL FIELD OF THE INVENTION

The present invention relates generally to the field of endoscopic and arthroscopic surgery and suture anchor systems and devices for use therein. More particularly, the invention relates to a knotless suture anchor device utilized to secure soft tissue to bone or a boney surface to preclude the need to tie surgical knots to secure the tissue in place with the device. Specifically, the invention relates to a simplified anchor system and method by which the surgeon may introduce one or more sutures into a hole in the bone, apply tension to the sutures to advance the soft tissue to a desired location, and then advance the anchor into the bone while maintaining the suture tension and graft position.

BACKGROUND OF THE INVENTION

The use of implants to affix tissue grafts to bone is well known in the orthopedic arts. Common procedures in which such implants are used include, for example, the repair of rotator cuff tears, the repair of torn ligaments in the knee, among others. In these procedures, a socket is drilled or punched in the bone at the attachment site and a graft is secured to the bone using an implant placed in the socket. The graft may be secured to the implant by sutures, or, alternatively, an end of the graft may be placed in the socket and secured directly by an implant.

In rotator cuff repair implants commonly referred to as "anchors" are used. These anchors occur in two types: conventional anchors in which the suture is passed through the cuff after anchor placement, and "knotless" anchors in which the suture is passed through the cuff prior to anchor placement. In the former case, the graft is secured in place by tying knots in the suture after it has been passed through the cuff so as to secure the cuff in the desired location. Conversely, as the name implies, when using a knotless anchor the sutures are passed through the cuff and through a feature of the anchor such that when the anchor is inserted into the socket, the suture position is secured by the anchor. The tying of knots is not required. This is particularly advantageous when performing endoscopic (arthroscopic) repairs since the tying of knots arthroscopically through a small diameter cannula may be difficult for some surgeons and, moreover, there is an opportunity for tangling of the sutures.

Many anchors, both conventional and knotless, are supplied to the surgeon mounted on a driver—a device that the surgeon uses to place the anchor in the prepared socket in the bone. In the case of threaded anchors, the driver has a form like that of a screwdriver, and indeed functions in the same manner. The proximal portion of the device forms a handle that is grasped by the surgeon. Distal to the handle, an elongate distal portion has formed at its distal end features for transmitting torque to an implant. Some anchors, generally metallic anchors such as, for instance, the Revo® Suture Anchor by Conmed Corporation (Utica, N.Y.) and Ti-Screw Suture Anchor by Biomet Corporation (Warsaw, Ind.), have a protruding (male) proximal portion with a cross-section suitable for transmitting torque (typically hexagonal or square) and a transverse eyelet formed therein. The driver for such devices has a complimentary socket (female) formed in its distal end and a cannulation that extends from the interior of the socket to the proximal handle portion of the device. Sutures loaded into the eyelet of the anchor extend through the driver cannulation (or "lumen") and are removably secured to the handle so as to retain the anchor in the socket of the driver. Such anchors are referred to in the orthopedic arts as "pre-loaded", meaning that sutures come loaded into an anchor that is ready for placement by the surgeon using the associated driver.

Other threaded anchors have a socket (female) formed in their proximal ends. Once again, the socket has a cross-section suitable for transmitting torque that is typically polygonal, usually square or hexagonal. Typical of these are the V-LoX™ family of titanium suture anchors by Parcus Medical (Sarasota, Fla.) and the ALLthread™ anchors by Biomet Corporation (Warsaw, Ind.). The drivers for such devices have a protruding (male) torque-transmitting feature complementary to the socket (female) formed in the proximal end of the anchor. These drivers may be cannulated to accommodate sutures that are preloaded into the anchor in the manner previously described, with the sutures being either for the purpose of securing tissue after anchor placement, or for the purpose of removably securing the anchor to the driver, wherein the sutures are released from the driver after the anchor is placed in the bone and subsequently removed and discarded so as to allow removal of the driver from the anchor. The depth of the socket in the proximal end of the implant must be sufficient to enable transmission of the requisite torque needed for anchor placement without deforming or fracturing the implant. As the maximum depth of the torque-transmitting portion is generally limited only by the configuration of the anchor, it is considered to be matter of design choice. Indeed, the implant may have a cannulation that extends axially through the implant as well as a torque-transmitting cross-section forming a substantial proximal portion or the entirety of the implant's length. Implants of the Bio-Tenodesis Screw™ System by Arthrex, Inc have a cannulation with a constant torque-transmitting cross-section, and are used with a driver having a torque-transmitting portion that extends beyond the distal end of the anchor, wherein the portion of the driver extending beyond the anchor and a suture loop in the driver cannulation are used together to insert the end of a graft into a prepared socket prior to placement of the implant.

Knotless suture anchor fixation is a common way of repairing soft tissue that has been torn from bone. Illustrative examples of such "knotless" anchors include the Allthread™ Knotless Anchors by Biomet Incorporated (Warsaw, Ind.), the SwiveLock® Knotless Anchor system by Arthrex, Incorporated (Naples, Fla.), the HEALIX Knotless™ Anchors by Depuy/Mitek, Incorporated (Raynham, Mass.) and the Knotless Push-In Anchors such as the Knotless PEEK CF Anchor by Parcus Medical (Sarasota, Fla.). The procedure requires drilling or punching of holes into a properly prepared boney surface. After suture has been passed through soft tissue the suture anchor is introduced into the socket and driven into the socket using a mallet or by screwing the anchor into the socket using a driver device. These driver devices typically resemble a screwdriver in form, having a proximal handle portion for applying torque or percussive force, and an elongate rigid distal portion having at its distal end a torque or percussive force-transmitting configuration. In the case of torque transmitting drivers used with threaded anchors, the distal end of the driver typically has an elongate hexagonal or square distally extending portion that, through coupling with a lumen in the anchor having a complementary cross-section, transmits torque to the anchor. The lumen may extend through anchor so that the distal portion of the driver protrudes from the distal end of the anchor and rotates with the anchor during anchor placement.

Because the suture is drawn into the prepared socket along with the anchor during anchor placement, it is essential that a suitable length of suture extends between the graft and the anchor so that when the anchor is suitably positioned within the socket, the graft is properly positioned. Determining the proper length of suture to allow between the anchor and the graft so as to achieve optimal graft positioning is complicated since suture may twist (a process referred to in the orthopedic arts as "suture spin") during anchor placement, thereby shortening the effective length and changing the final graft position and/or undesirably increasing the suture tension.

U.S. Pat. No. 6,544,281 to ElAttrache et al. describes a cannulated anchor placement system having a rotating inner member (which acts as the anchor driver) and a stationary outer member, wherein the rotating inner member serves to drive the threaded anchor. The rotating "driver" extends past the distal end of the anchor and is inserted into a prepared socket in the boney surface. A suture loop formed distal to the distal end of the driver "captures" or "secures" sutures attached to a graft or the graft itself to the distal end of the driver. The distal end of the driver is then inserted into the socket to a proper depth for anchor placement thereby drawing the graft to the desired position prior to placement of the anchor. The anchor is then threaded into the socket to the predetermined depth. This system constitutes an improvement over other commercially available alternatives. However, because the graft or sutures are secured to or pass through the distal end of the rotating inner (or "driver"), torque is transmitted not only to the anchor but also to the graft or sutures attached thereto by the suture loop. Accordingly, twisting of the sutures or graft frequently occurs, thereby changing the resulting suture tension and/or the graft position (a process referred to in the orthopedic arts as "graft shift").

U.S. Pat. No. 8,663,279 by Burkhart et al. describes a knotless anchor system similar in construction to that of ElAttrache et al. A "swivel" implant having formed therein an eyelet is releasably and pivotably mounted to the distal end of a driver distal portion that extends distally beyond the distal end of an anchor. After sutures are passed through the graft, they are threaded into the eyelet of the swivel implant at the distal end of the driver. The distal end of the driver with the swivel implant is then inserted into the socket. By pulling on the suture tails, the graft is moved into position and secured by screwing the anchor into the socket. However, because the sutures/graft are secured to the driver by means of the swivel eyelet implant, the torque that may be transmitted to the sutures/graft is limited. Torque transmission is not eliminated since the swivel implant is retained in the driver distal end by a suture loop under tension, which extends through the cannula of the driver to the driver's proximal end where the suture ends are cleated. While an improvement over the ElAttrache anchor system, suture spin is not eliminated in all cases, and indeed, cannot be since the suture-retaining implant is mounted to the driver, which rotates during anchor placement. As such, some level of torque transmission due to friction between the driver distal end and the swivel eyelet implant is inevitable.

Other knotless anchors such as the ReelX STT™ Knotless Anchor System by Stryker® Corporation (Kalamazoo, Mich.) and PopLok® Knotless Anchors by ConMed Corporation (Utica, N.Y.) have complex constructions and require that the surgeon perform a sequence of steps to achieve a successful anchor placement with the desired suture tension and proper cuff position. The sequence of steps adds to procedure time and creates opportunities for failure of the placement procedure if a step is not performed properly.

Accordingly, there is a need in the orthopedic arts for a knotless anchor system that allows the surgeon to establish the graft position, and, while maintaining that position, place the anchor without changing the suture tension or causing a shift in the graft position due to suture spin. Furthermore, if the anchor is threaded, placement of the anchor in the socket must occur without spinning of the suture.

If a graft such as a biceps tendon is directly affixed to a bone by insertion of the graft into a socket (a technique referred to as "bio-tenodesis"), it is essential that the graft be fully inserted so as to be engaged by the full length of the implant. It is also important that the position of the graft be maintained during anchor insertion. Further, it is essential that the alignment of the implant (referred to in this case as an "interference screw") be coaxial, or if slightly shifted, parallel to the axis of the socket. It is also desirable that the sutures used to draw the graft into the socket do not spin or twist during anchor placement as this may change the position and tension of the graft from that intended by the surgeon. In sum, there is a also need in the suture arts for an interference screw and implant placement system in which graft position within the socket is maintained throughout the implant placement process, and in which suture spin or twisting is prevented.

Improved implant systems can also find utility in the context of spinal fusion surgery, wherein rigid posterior or lateral or anterior elements, either pedicle based, interbody based, or vertebral body based, or posterior element based, are routinely performed, by the placement of screws into the bony spinal elements and, through either internal mechanisms or rigid bridging devices, engage into adjacent bony elements or interspaced to provide rigid fixation. Illustrative examples of commercially available spinal fixation devices include, for example, Synthes (Raynham, Mass.), Nuvasive (San Diego, Calif.) and Amendia (Atlanta, Ga.), devices that interlock cervical, thoracic or lumbar or sacral levels to rigidly prevent movement and fuse or allow for fusion of diseased or degenerated segments of spine to prevent painful or disabling movement. These rigid zones of fixation create zones above and below these constructs, which are known as junctional or transitional zones or levels. There is need in the art for a bracing mechanism that can disperse load from the rigidly fixed spinal segments having undergone prior fusion or fixation, to unfused adjacent spinal segments. Such a bracing device, while not providing absolute rigid fixation but allowing for movement, would provide for bracing of the non fused segments while off-loading or reducing the forces that, prior to the application of such a device, would have been entirely borne by the intervertebral discs and adjacent bony elements and ligaments adjacent to the prior rigid fixed segments. It is this increased force that is postulated to result in failure of the adjacent segment.

Suitable bracing devices can be inserted either along the anterior aspect of the spinal segments, the posterior aspect of the spinal segments, or between spinal segments. Between these anchor devices and the spinal segments or between the fusion devices and spinal segments, or bridging these spinal segments and fusion devices to intact spinal segments, either soft tissue in the form of grafts, or with braided suture constructs, or with a combination thereof, bone anchors are utilized to insert these tension bearing or tension off loading constructs. Such tension-bearing constructs serve to provide a dynamic rather that rigid transition from the fused spinal segments to the adjacent spinal segments. The purposes of theses constructs are to reduce the load applied to the intervertebral discs above and below the fused spinal segments. This transitional loading allows the adjacent musculature to recover following spinal fusion surgery while protecting the discs until the muscle has recovered sufficiently, while also allowing needed movement at the transitional levels so as to not have created another static or rigidly fixed level. In addition, such constructs can be utilized to reconstruct spinal ligaments. Such reconstructions can be performed either independent of, or in addition to rigid spinal fixation or along with intervertebral body disc replacements to help restore normal spinal segment mobility and preserve or protect the constructs.

SUMMARY OF THE INVENTION

A primary objective of the present invention is to provide improved means and methods of attaching soft tissues (i.e., "grafts") to bone in situ. The embodiments of the instant invention are described hereinbelow as a system and method for producing a matrix of implants for the anchoring of a graft to bone. Any graft fixation system which uses an implant placement system with an optionally cannulated non-rotating tensioning device (i.e., the relatively fixed "inner assembly") positioned within a lumen of a cannulated driver (i.e., the relatively movable "outer assembly") to tension sutures in a prepared socket for the placement of a simple one-piece cannulated anchor are contemplated by the present invention. Illustrative aspects and embodiments of the present invention in accordance with the foregoing objective are as follows:

In a first aspect, the present invention provides prosthetic implants and systems for their placement in a target boney surface for the knotless securing of a soft tissue graft thereto. The instant invention contemplates a novel placement system including a non-rotating cannulated tensioning device ("inner assembly") positioned within a rotationally and axially movable cannulated driver ("outer assembly"). In a preferred embodiment, a distal element of the tensioning device extends distally beyond the distal end of the cannulated driver. A cannulated threaded implant (or "anchor") is removably mounted to the torque transmitting distal portion of the driver. Sutures placed in the graft are drawn into the distal end of the elongate distal portion of the cannulated tensioning device, which extends beyond the distal end of the implant. If a threaded implant is used, the distal end of the cannulated driver preferably includes torque-transmitting features that, together with complementary features formed in the proximal portion of the implant or anchor, allow the transmission of torque thereto. If an interference plug-type anchor is used, the distal end of the driver is preferably configured to transmit axial force to the anchor, the distal end of which has suitable complementary features to enable secure attachment.

In operation, sutures placed in the graft are drawn into the distal end of the tensioning device. The elongate distal portion of tensioning device is inserted into a properly prepared socket in the target boney surface so that the distal end of the tensioning device, with its sutures is positioned at the bottom of the socket. Tension is then applied to the sutures by pulling on their proximal ends, which extend beyond the proximal portion of the tensioning device to move the graft into the desired position, namely into the prepared socket adjacent to the distal element of the tensioning device. The desired tension may be maintained by cleating proximal portions of the suture(s) into slots optionally formed in the handle of the tensioning device. The anchor (or interference screw) may then be screwed, threaded or otherwise driven into the socket, thereby trapping the sutures or graft between the anchor exterior surface and the socket wall. Critically, twisting of the sutures or graft is prevented by the non-rotating distal portion of the tensioning device that remains distal to the anchor distal end during anchor placement. In addition, tension on the sutures and the position of the graft are maintained during placement of the anchor throughout the procedure. After anchor placement, the driver and tensioning device are withdrawn, removed from the site, at which point the sutures may be trimmed to complete the procedure.

In contrast to the Burkhart and ElAttrache anchor systems, suture tensioning and establishment of the graft position are not accomplished using the driver's distal end or using an implant positioned in the driver's distal end. Rather, suture tension and graft position are established and maintained by the distal portion of a non-rotating tensioning device that extends beyond the driver and anchor distal ends. Because of this, the transmission of torque to the sutures and/or graft by the driver present in the Burkhart and ElAttrache systems is eliminated along with its associated suture or graft spin.

The system and method of the instant invention provide a simplification over other currently available anchoring methods and hardware in that fewer steps are required and moreover the anchor has a simple, single-piece construction. The anchor system is scalable and, due to its simple construction, may be used with anchors smaller than those permitted using other currently available systems. The composition and construction in the anchor may be readily modified simply by changing the material from which it is constructed, by increasing or reducing the diameter or length of the anchor, by increasing or decreasing the wall thickness of the anchor, by modifying the profile of the exterior, or by any combination of these means. All such modifications are contemplated as within the scope of the present invention.

In another aspect, the present invention provides a method for affixing a soft tissue graft to a target boney surface, the method comprising the steps of:

a. providing a placement system having a cannulated non-rotating tensioning device ("inner assembly") and a cannulated driver device ("outer assembly"), wherein the tensioning device is positioned within the cannulation or "lumen" of the driver device, b. positioning a cannulated anchor onto the distal torque-transmitting portion of the driver, over a distally extending element of the tensioning device,
c. producing a suitably configured hole (i.e., "socket") in a prepared boney surface at a desired target location using a drill, tap, punch or equivalent hole-producing device,
d. drawing sutures from the graft into the lumen of the tensioning device,
e. inserting the distal end of the tensioning device into the socket,
f. applying tension to the sutures to draw the graft to a desired position,
g. placing the anchor (or interference screw) in the socket,
h. withdrawing the placement system,
i. trimming the suture tails, and
j. optionally repeating steps (c) through (i) as required.

In an alternate embodiment of the present invention, identical in all aspects to the previous embodiment except as subsequently described, the tubular distal portion of the tensioning device is replaced by a rod having formed at its distal end a sharpened fork portion, optionally wherein two (or more) parallel, axially extending tines form the fork, the tines being spaced apart so that sutures may slide freely through the channel(s) formed between the tines. Alternatively, the distal end may include linear or curved "tines" that bend or extend medially at their distal ends so that channel formed between distally extending portions forms an eyelet having a gap in its distal end, a configuration referred to herein as a "split" suture-capturing loop.

An anchor placement system commensurate with any such alternate embodiment is used in the following manner: First, a cannulated threaded implant is removably mounted to the torque-transmitting distal portion of the driver. Sutures placed in the graft are then positioned in the channel(s) (or eyelet) of the distal fork portion of the tensioning device. The elongate distal portion of the tensioning device with the sutures positioned within its distal channel is then inserted into a prepared socket so that the distal end of the tensioning device with its sutures is positioned at the bottom of the socket. Tension is then applied to the sutures by pulling on their proximal ends to draw the graft into the desired position. The desired tension and graft position may be maintained by cleating the suture proximal portions in slots optionally formed in the handle of the tensioning device. The anchor is then screwed, threaded or otherwise driven into the socket by the driver, thereby trapping the sutures or graft between the anchor exterior surface and the socket wall. Twisting of the sutures or graft is prevented by the non-rotating distal fork portion of the tensioning device which remains distal to the anchor distal end during anchor placement. The tension on the sutures and the position of the graft are maintained during placement of the anchor. After anchor placement, the driver and tensioning device are removed from the site and the sutures trimmed to complete the procedure.

An anchor placement system of the present embodiment may also include a mechanism for releasably preventing relative axial and rotational movement between the driver and the tensioning device, such means optionally positioned within the cannulation (or "lumen") of the driver. In a first condition used during tensioning of the suture, relative axial and rotational motion is of the driver relative to the tensioning device is prevented. In a second condition, used during placement of the anchor, the driver may be advanced axially on the tensioning device to bring the anchor to the socket, and rotated to screw the anchor into the socket, with the tensioning device remaining stationery so as to maintain suture tension and prevent twisting of the sutures.

In a particularly preferred embodiment, prevention of relative motion is provided by a removable key having one or more protrusions, coupled with features formed on the handles of the tensioning device and driver such that, when the features are in alignment, engagement by the one or more protrusions of the key prevents relative axial or rotational movement between the torque-transmitting driver and the tensioning device. Removal of the key allows the driver to be advanced distally and rotated relative to the tensioning device. Other embodiments are anticipated in which other means are used to releasably prevent relative motion.

In another aspect, like the previous in all other respects except as subsequently described, the suture attached to the graft is positioned within the distal fork and tensioned such that the proximal end of the graft is adjacent to the fork, the tension being maintained by cleating of the sutures on the tensioning device handle. The distal portion of the tensioning device with the graft is inserted into the prepared socket. The anchor is then threaded or driven into the socket as previously described, thereby trapping the graft proximal portion between the anchor exterior surface and a first portion of the socket wall, and the attached sutures between the anchor exterior surface and a second, laterally opposed portion of the socket wall.

In a variation of the previous aspect, the graft may be pierced by one or more sharpened, distally extending member(s) or "tine(s)" of the distal portion. The distal portion may optionally further include a depth-limiting element of a suitable metallic or polymeric material that is axially slidable along and removably affixed to, for example via a friction fit, the one or more sharpened distally extending member(s) that prevents undue penetration, damage and/or tearing of the graft. In either case, the distal portion of the tensioning element with the graft is inserted into the prepared socket. Once again, the anchor is then threaded or driven into the socket, thereby trapping the graft proximal portion between the anchor exterior surface and a portion of the socket wall.

In another variation of the previous aspect, the graft is pierced by the sharpened distally extending members of the distal fork a predetermined distance from the graft distal end such that when the distal portion of the tensioning element with the graft is inserted into the prepared socket, the proximal end of the graft protrudes above the opening of the socket. The anchor is then threaded or driven into the socket, thereby trapping the graft proximal portion between the anchor exterior surface and first and second laterally opposed portions of the socket wall.

In still yet another aspect, identical in form to the devices and insertion systems previously herein described, the tensioning device has a proximal handle portion that is an assembly of first and second rigid elements with an elastic element positioned therebetween. Applying a distal force to a first rigid element of the handle of the tensioning device causes deflection of the elastic element proportional to the tension in the graft attached to the distal fork. This allows the practitioner to measure the tension in the graft. By establishing the tension in the graft to a predetermined value prior to placement of the anchor, the tension may then be maintained at the predetermined value during anchor placement.

These and other aspects are accomplished in the invention herein described, directed to a system and method for producing a matrix of implants for the anchoring of a graft to bone. Further objects and features of the invention will become more fully apparent when the following detailed description is read in conjunction with the accompanying figures and examples. For example, any graft fixation system that uses a non-rotating inner member (tensioning device) and a movable outer member (driver) to tension sutures in a prepared socket for the placement of a simple one-piece cannulated anchor falls within the scope of this invention. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 1A is a plan view of the cannulated driver and anchor of an implant placement system of the present invention.

FIG. 1B is an expanded view of the distal portion of the objects of FIG. 1A at location C.

FIG. 1C is a side elevational sectional view of the objects of FIG. 1A at location A-A of FIG. 1A.

FIG. 3 is a plan view of the tensioning device of an implant placement system of the present invention.

FIG. 4 is an expanded sectional view of the tensioning device of FIG. 3 at location A-A.

FIG. 5 is an expanded view of the proximal hub portion of the tensioning device of FIG. 3 at location A.

FIG. 6 is a side elevational view of the objects of FIG. 3.

FIG. 7 is an expanded view of the objects of FIG. 6 at location B.

FIG. 16 is a side elevational view of the objects of FIG. 13.

FIG. 17 is an expanded view of the objects of FIG. 13 at location B.

FIG. 64 is a plan view of a distal assembly for the tensioning device for an alternate embodiment anchor placement system that includes a force indicating inner tensioning assembly.

FIG. 65 is a side elevational view of the objects of FIG. 64.

FIG. 66 is a sectional view of the objects of FIG. 64 at location A-A.

FIG. 67 is an expanded proximal axial view of the objects of FIG. 64.

FIG. 80 is a plan view of an alternate embodiment anchor placement system of the present invention that allows the surgeon to measure the tension in the graft during the attachment of the graft in accordance with the methods of the present invention.

FIG. 81 is an expanded view of the proximal portion of the objects of FIG. 80 at location A.

FIG. 115 is a perspective view of the handle portions of another alternate embodiment of the present invention.

FIG. 116 is a plan view of the objects of FIG. 115.

FIG. 117 is a perspective view of the hub portion of a tensioning device for an alternate embodiment implant placement system of the present invention.

FIG. 118 is a perspective view of the proximal portion of the handle of a driver for an alternate embodiment implant placement system of the present invention.

FIG. 119 is an expanded plan view of the distal end of a tensioning device for an alternate embodiment implant placement system of the present invention.

FIG. 120 is a distal perspective view of the objects of FIG. 119.

FIG. 121 is a proximal perspective view of the objects of FIG. 119.

FIG. 122 is an expanded plan view of the distal end of an alternate embodiment implant placement system in accordance with the present invention.

FIG. 123 is a perspective view of the objects of FIG. 122.

FIG. 124 is an expanded perspective view of the objects of FIG. 122.

FIG. 125 is a perspective view of a depth-limiting element for an alternate embodiment implant placement system of the present embodiment.

FIG. 126 is a side elevational view of the objects of FIG. 125.

Figure 125:
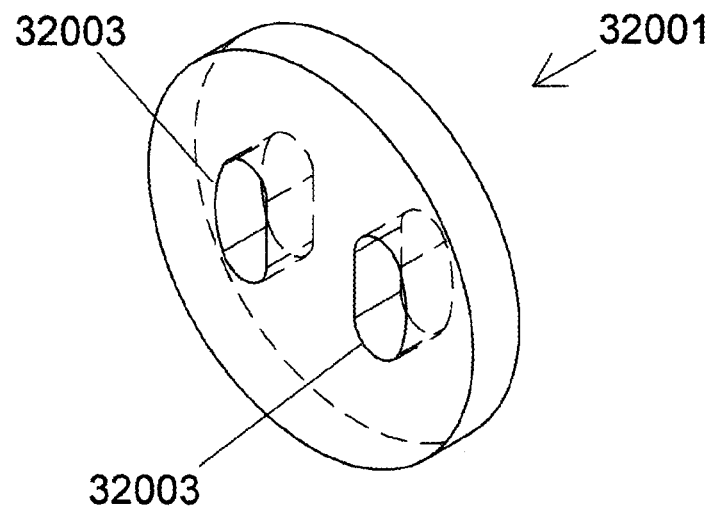
Figure 127:
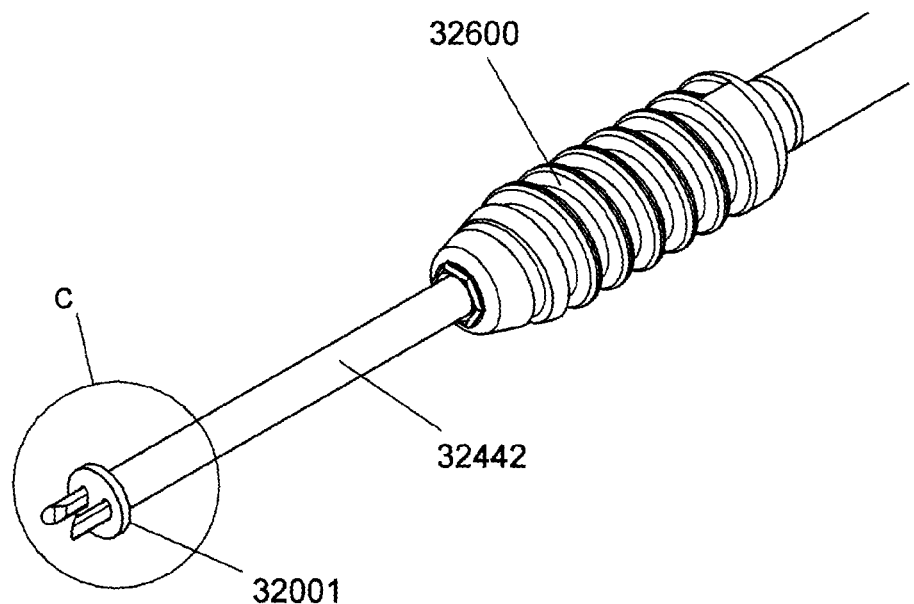

FIG. 127 is an expanded perspective view of an alternate embodiment implant placement system of the present invention incorporating the depth-limiting element of FIG. 125.

Figure 128:
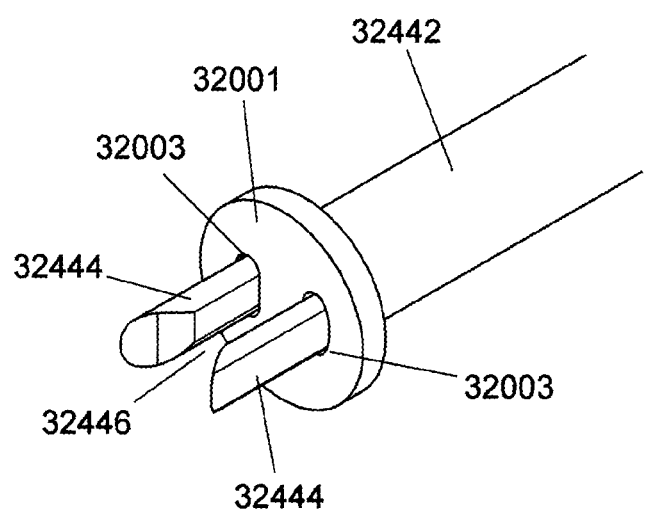

FIG. 128 is an expanded view of the objects of FIG. 127 at location C.

Figure 129:
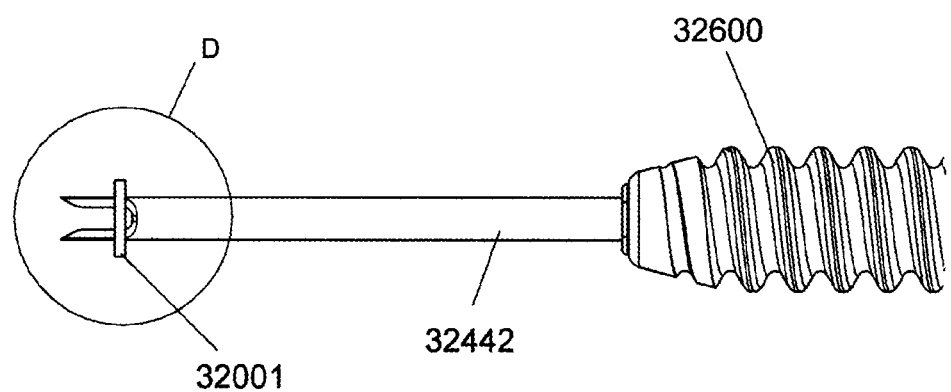

FIG. 129 is a plan view of the objects of FIG. 127.

Figure 130:
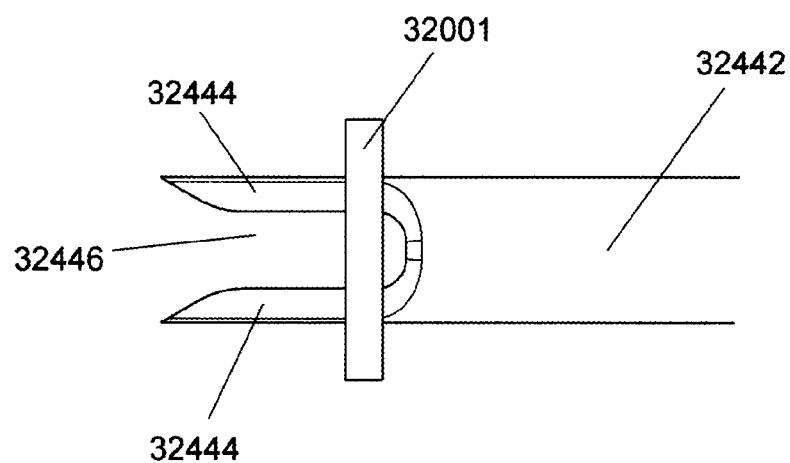

FIG. 130 is an expanded view of the objects of FIG. 129 at location D.

Figure 131:
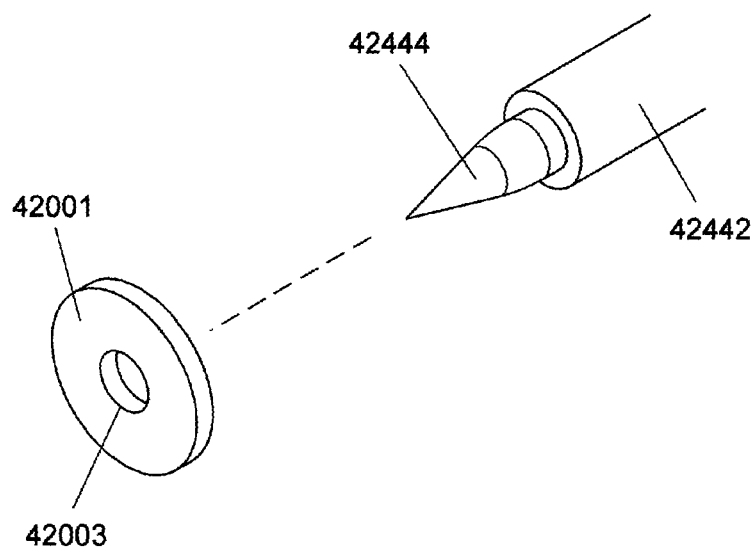

FIG. 131 is a perspective view of the distal portion of an alternate embodiment implant placement system of the present invention depicting a depth limiting element positioned for mounting to the distal end of a distal element.

Figure 132:
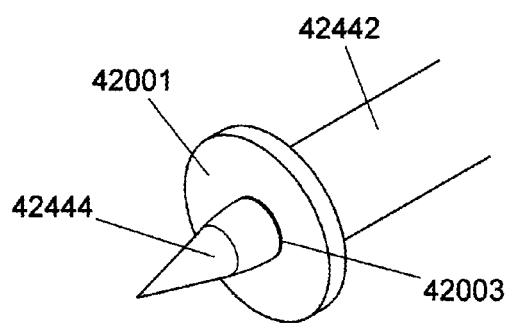

FIG. 132 is a perspective view of the elements of FIG. 131 assembled in preparation for use.

Figure 133:
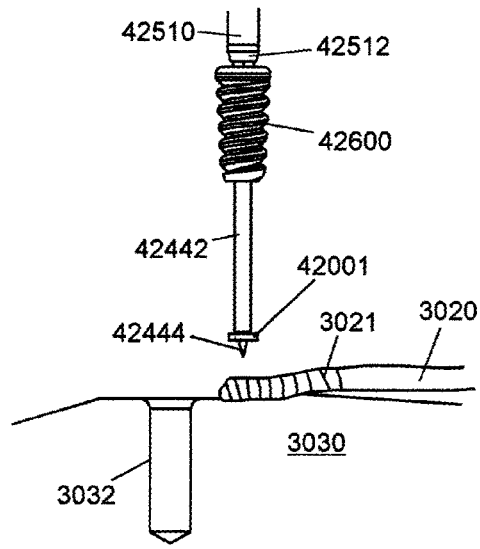

FIG. 133 depicts a first step of an alternate repair method for securing a graft in a socket using an implant.

Figure 134:
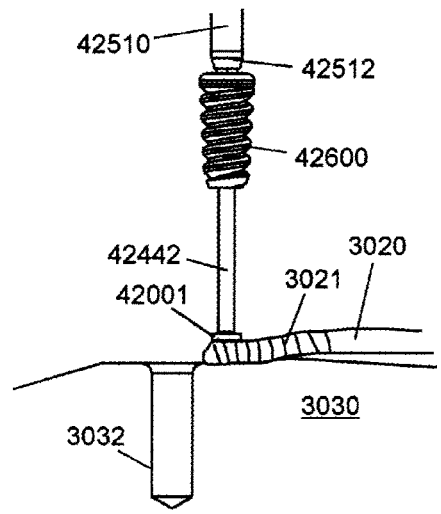

FIG. 134 depicts a second step of the alternate repair method

Figure 135:
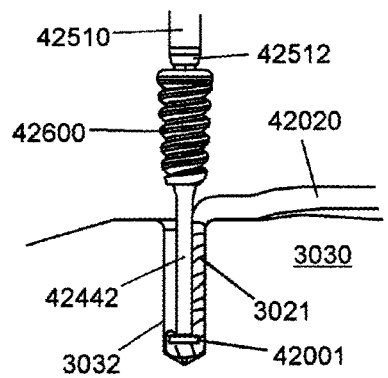

FIG. 135 depicts a third step of the alternate repair method.

Figure 136:
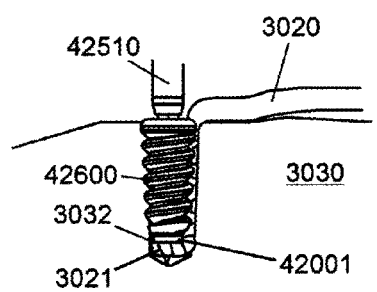

FIG. 136 depicts a fourth step of the alternate repair method.

Figure 137:
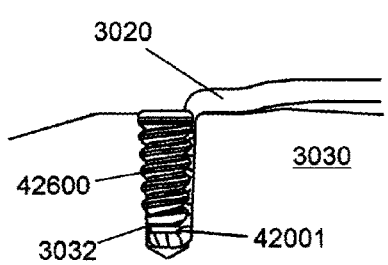

FIG. 137 depicts the site of the graft attachment at the completion of the repair using the alternate embodiment repair method.

Figure 138:
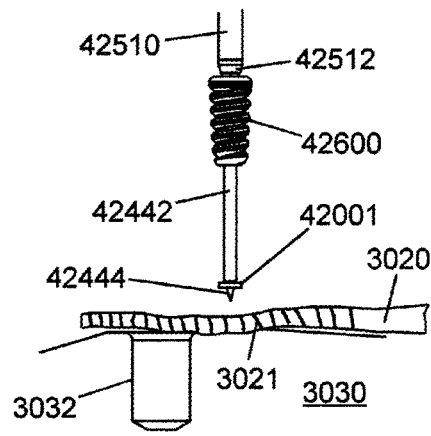

FIG. 138 depicts a first step of another alternate repair method for securing a graft in a socket using an implant.

Figure 139:
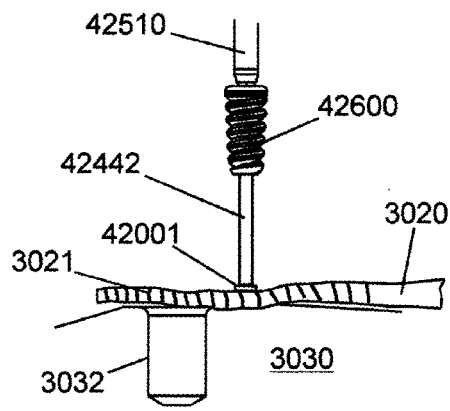

FIG. 139 depicts a second step of the alternate repair method

Figure 140:
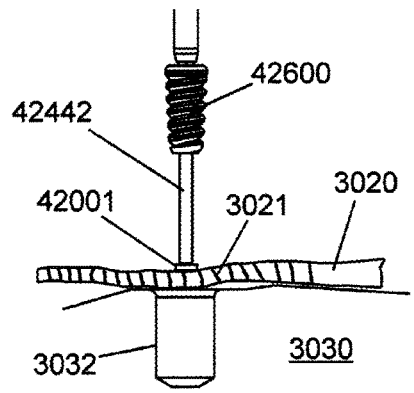

FIG. 140 depicts a third step of the alternate repair method.

Figure 141:
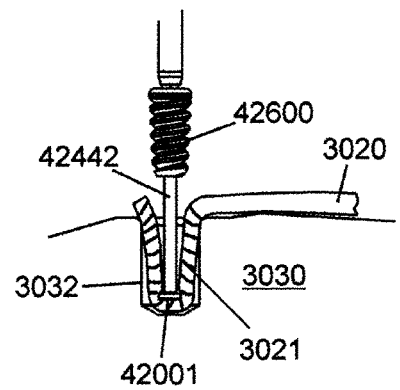

FIG. 141 depicts a fourth step of the alternate repair method.

Figure 142:
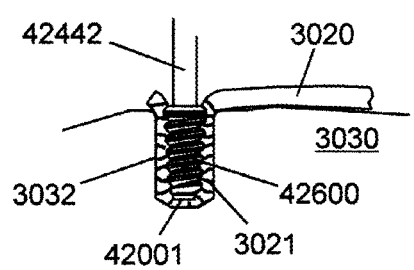

FIG. 142 depicts a fifth step of the alternate repair method.

Figure 143:
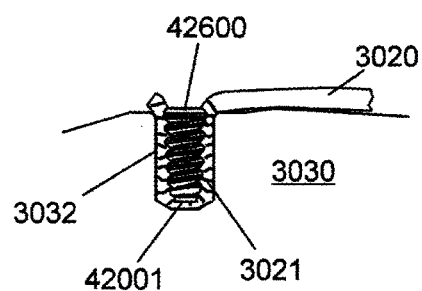

FIG. 143 depicts the site of the graft attachment at the completion of the repair using the alternate embodiment repair method.

DETAILED DESCRIPTION OF THE PREFERRED EMBODIMENTS

Aspects of the present invention relate to, overlap with and/or find utility in conjunction with aspects described in the following related co-pending applications, the entire contents of which are hereby incorporated in their entirety:

U.S. application Ser. No. 15/256,815 filed Sep. 6, 2016 entitled "Ceramic Implant Placement Systems And Superelastic Suture Retention Loops For Use Therewith";

U.S. application Ser. No. 15/256,838 filed Sep. 6, 2016 entitled "Implant Placement Systems And One-Handed Methods For Tissue Fixation Using Same"; and U.S. application Ser. No. 15/256,945 filed Sep. 6, 2016 entitled "Multiple Implant Constructions and Fixation Methods Associated Therewith.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the implant system of the present invention includes the driver and handle portions.

The term "distal" as used herein refers to that end or portion situated farthest away from the user of the device, closest to the target surgical site. In the context of the present invention, the distal end of the implant systems of the present invention includes components adapted to fit within the pre-formed implant-receiving socket.

In the context of the present invention, the terms "cannula" and "cannulated" are used to generically refer to the family of rigid or flexible, typically elongate lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" as used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, when a tissue, more particularly a soft connective tissue in a joint space, becomes damaged or torn from its associated bone or cartilage, surgery is usually required to reattach the tissue or reconstruct the bone. The present invention is directed to various means and mechanisms for securing the displaced tissue to boney tissue.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the shoulder, elbow, knee or ankle joint.

In a similar fashion, while the present invention is not restricted to any particular boney tissue, a term used herein to refer to both bones and cartilage, aspects of the present invention find particular utility in the repair or reattachment of connective tissues to the boney elements of the shoulder, elbow, knee or ankle joint.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;

Isografts, i.e., grafts taken from one individual and placed on another individual of the same genetic constitution, e.g., grafts between identical twins;

Allografts, i.e., grafts taken from one individual placed on genetically non-identical member of the same species; and Xenografts, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket", i.e., a hole punched or drilled into the bone into which a prosthetic device such as an implant may be received. The socket may be prepared at the desired target location using conventional instruments such as drills, taps, punches or equivalent hole-producing devices.

While certain procedures contemplate directly attaching the graft to the bone, the more common route involves the employment of an implant specially configured to hold and/or enable attachment of the graft to the boney tissue. As used herein, the term "implant" refers to a prosthetic device fabricated from a biocompatible and/or inert material. In the context of the present invention, examples of such "implants" include conventional and knotless anchors of both the screw-threaded and interference-fit variety.

In certain embodiments, the present invention contemplates fabrication of the implant from either a metallic material or a suitable polymeric material, including, but not limited to, polyetheretherketone (PEEK), a polymeric composite such as, for instance, carbon fiber reinforced PEEK (PEEK CF), or of a suitable bioabsorbable material such as, for instance, polylactic acid (PLA). The present invention also contemplates the use of very small knotless anchors produced from ceramic materials using a process known as "Ceramic Injection Molding" or simply "CIM". The tensile strength of PEEK material is typically between 10,000 and 15,000 psi. In comparison, the tensile strength of alumina is generally in excess of 200,000 psi. Furthermore, recently developed materials such as Zirconia Toughened Alumina (ZTA) by Coorstek Inc. (Golden, Colo.) have a high degree of toughness in addition to high tensile strength. These materials, being ceramic, do not have a yield point and therefore do not deform under load. The high tensile strength and the absence of yielding under load of an implant constructed of such ceramic materials allow torque to be transmitted to the implant through features that are not producible by the machining of metal or that would fail in use if formed from a polymeric material such as PEEK.

In other embodiments, the implant may take the form of a ceramic interference plug, wherein the high elastic modulus and high strength of the ceramic materials is beneficial for small and miniature interference type anchors that are driven axially into a prepared socket. The high modulus and high strength of the materials allows the thickness of the wall between the central lumen and the outer surface to be reduced compared to interference type anchors produced from polymeric materials without reducing the compressive force which retains the one or more sutures between the outer wall of the implant and the wall of the socket.

The preferred implant system of the present invention is comprised of a cannulated tensioning device (e.g., the insertion device) slidably received within the lumen of a cannulated driver (e.g., the implant driver) that together serve to tension sutures in a prepared socket for the placement of a simple one-piece cannulated anchor. In the Examples below, the present invention makes reference to various lock-and-key type mating mechanisms that serve to establish and secure the axial and rotational arrangement of these device components. It will again be readily understood by the skilled artisan that the position of the respective coordinating elements (e.g., recessed slots and grooves that mate with assorted projecting protrusions, protuberances, tabs and splines) may be exchanged and/or reversed as needed.

The implant placement system of the present invention requires a robust connection between the "driver device" and the associated "implant" or "anchor" so as to ensure that the two rotate as a single unit such that rotational force or "torque" applied to the proximal end of the system (e.g., via the proximal handle portion of the driver device) is transmitted to the distal end of the system (e.g., the distal end of the implant disposed in the prepared socket) without incident or interruption. This continuous "torque transfer" along the length of the system, from proximal to distal end, is critical to the function of the driver, enabling it to distally advance the implant and firmly secure the implant (and any associated sutures or tissues) in the biological site of interest. In the context of the present invention, this continuous torque transfer is achieved by means of coordinating "torque-transmitting" elements, namely a distal "torque-transmitting portion" of the driver device that is configured to mate with and/or conform to a "torque-transmitting" (or alternatively "torque-receiving" or "torque-transferring") portion of the implant, such "portion" including at a minimum the proximal end of the implant though the present invention contemplates embodiments where "torque-transmitting" features on the implant extend along the length of the implant. The respective "torque-transmitting" features on the driver device and implant cooperate to ensure that any proximal torque applied by the user to the proximal handle portion of the device is directly conveyed ("transmitted") to the distal end of the implant.

In certain embodiments, the torque-transmitting portion of the implant may take the form of a laterally extending slot in the proximal end of the implant similar to a standard screwdriver slot; however, other geometries are contemplated and described in detail herein as well as in disclosures incorporated by reference herein. In addition, like the implant itself, the distal torque-transmitting portion of the driver may also be fabricated from a ceramic material and formed by ceramic injection molding so as to allow miniaturization of the torque-transmitting features.

The present invention makes reference to insertion devices commonly referred to in the art as "drills" and "drivers", i.e., devices that "drill" the socket and "drive" the implant into the socket. In the context of the present invention, the drills and drivers may be conventional, e.g., rigidly linear as previously herein described, or, as discussed in detail herein, "off-axis", e.g., having an angularly offset distal portion adapted to drill off-axis sockets in boney tissues that are remote and difficult to access and drive therein the corresponding implant, such as an anchor or interference screw.

The present invention contemplates securing the graft to the implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

In certain embodiments, the present invention makes reference to an elongate element of a superelastic and/or shape memory material configured to include a suture retention loop at its distal end and designed to be slidably received within a lumen of a cannulated tensioning device or inserter. In certain preferred examples, the elongate element takes the form of a "nitinol wire". In the context of the present invention, "nitinol" is a super elastic metal alloy of nickel and titanium. In a preferred embodiment, the two elements are present in roughly equal atomic percentage (e.g., Nitinol 55, Nitinol 60). Nitinol alloys exhibit two closely related and unique properties: shape memory effect (SME) and superelasticity (SE; also called pseudoelasticity, PE). Shape memory is the ability of nitinol to undergo deformation at one temperature, then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal.

The present invention also makes reference to high strength polymeric materials and high tensile strength ceramic materials, such as alumina or zirconia, that may be formed to complex shapes by a process referred to as Ceramic Injection Molding (CIM). In this process, ceramic powder and a binder material are molded to a shape that is subsequently fired in a furnace to eliminate the binder material and sinter the ceramic powder. During this sintering operation the item is reduced in size by twenty to thirty percent and achieves near 100% density with very high dimensional repeatability. Ceramic materials that are routinely molded and thus contemplated by the present invention include, but are not limited to, alumina, zirconia toughened alumina (ZTA) and partially stabilized zirconia (PSZ). The flexular strengths of these materials range from 55,000 psi to 250,000 psi, far higher than the 25,000 psi flexular strength of implantable PEEK material.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

Figure 85:
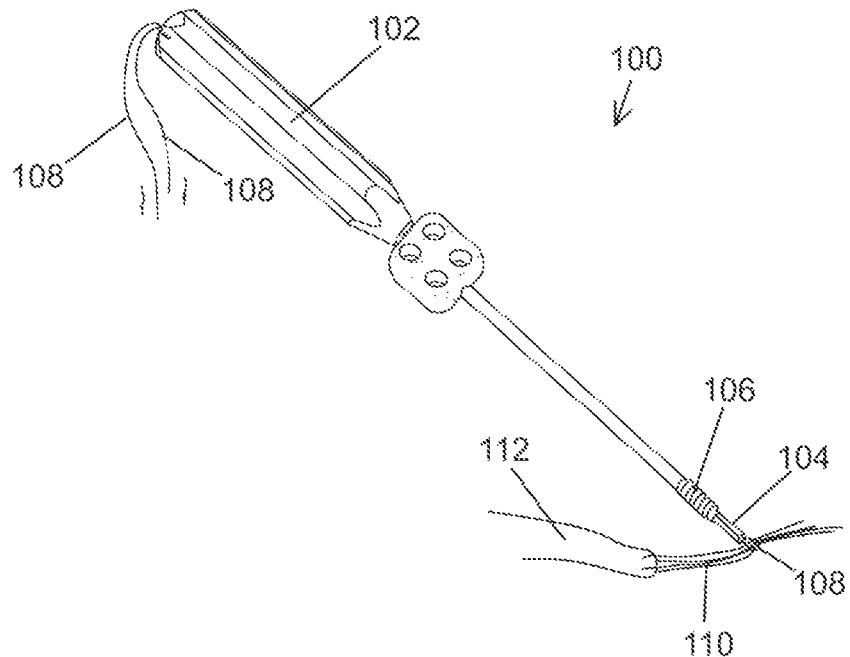
FIG. 85 is a perspective view of a prior art system for knotless anchor fixation of a tissue graft.
Figure 86:
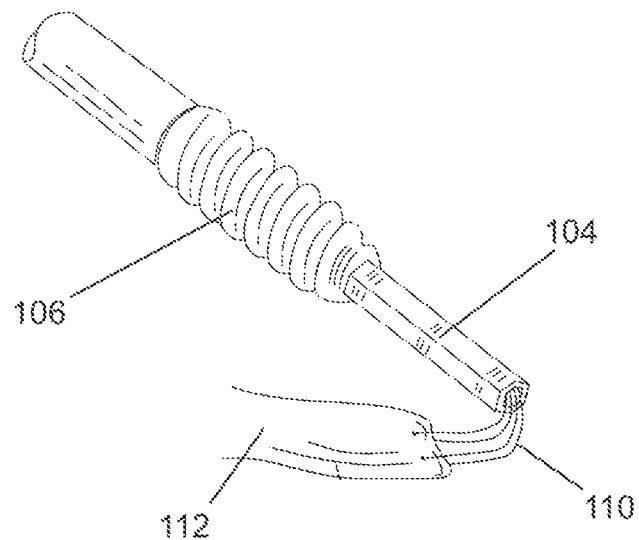
FIG. 86 is a perspective view of a prior art system for knotless anchor fixation of a tissue graft.
Figure 87:
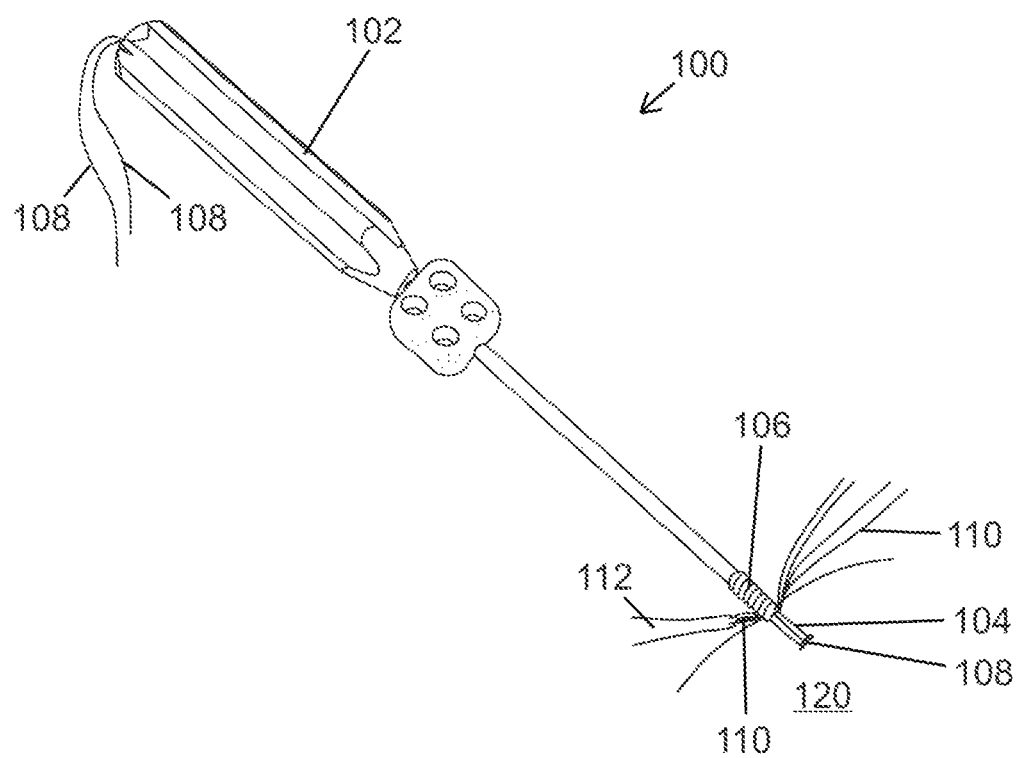
FIG. 87 is a perspective view of the prior art system of FIG. 85 positioning a graft for fixation prior to anchor placement.
Figure 88:
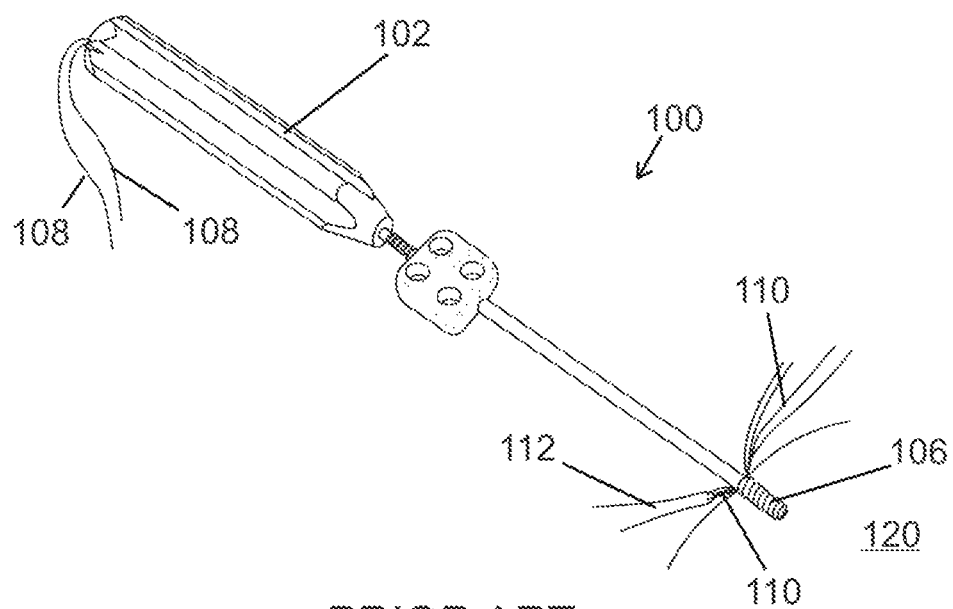
FIG. 88 is a perspective view of the system of FIG. 87 with the anchor placed.

FIGS. 85 through 88 depict a prior art device and method for the placement of a knotless suture anchor. Cannulated driver 100 has a handle portion 102 and a distal hexagonal portion 104 that protrudes beyond anchor 106. Suture 108 in the cannulation of driver 100 forms a loop at the distal end of distal hexagonal portion 104. In FIG. 85, sutures 110, which have been passed through graft 112, are positioned within the distal loop of sutures 108 where they are secured against the distal end of distal hexagonal portion 104 by tension applied by the surgeon to the proximal ends of sutures 108. Alternatively, graft 112 may be positioned within the distal loop of suture 108 and secured against the distal end of distal hexagonal portion 104 and maintained in that position by tension applied to sutures 108. Substantial tension must be maintained in sutures 108 when graft 112 is secured in this manner to ensure that the position of graft 112 does not change during insertion of the graft into the prepared socket and placement of anchor 106. In FIG. 86, sutures 110 have been drawn into the lumen of hexagonal distal portion 104 of driver 100. Subsequently, sutures 110 are placed under tension by the surgeon so as to secure graft 112 to the distal end of distal hexagonal portion 104 of driver 100. In FIG. 87, distal hexagonal portion 104 of driver 100, along with the sutures/graft secured to its distal end, have been inserted into a prepared socket thereby drawing graft 112 to the desired position. In FIG. 88, implant 106 has been screwed into the prepared socket thereby securing graft 112. Because sutures 110 or graft 112 are/is secured or captured at the distal end of rotating driver 100 by tensioned sutures 108 or 110, friction between the sutures 110 and the distal end of the driver 100 or between graft 112 and the distal end of driver 100 transmits torque to the sutures or graft. This transmitted torque may cause suture spin, graft shift, or improper tensioning of the construct.

Figure 89:
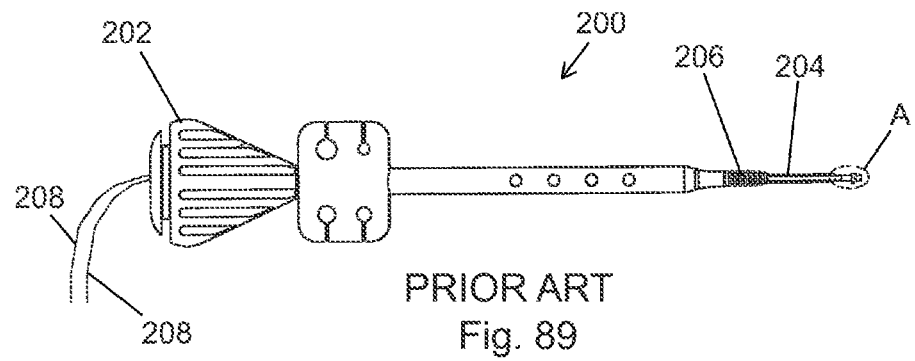
FIG. 89 is a plan view of a prior art system for knotless anchor fixation of a tissue graft.
Figure 90:
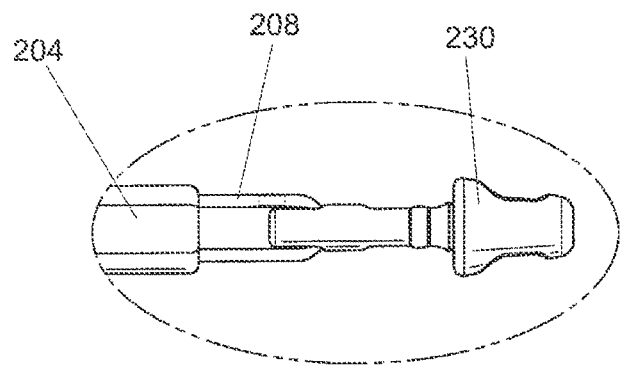
FIG. 90 is an expanded view of the objects of FIG. 89 at location A.
Figure 91:
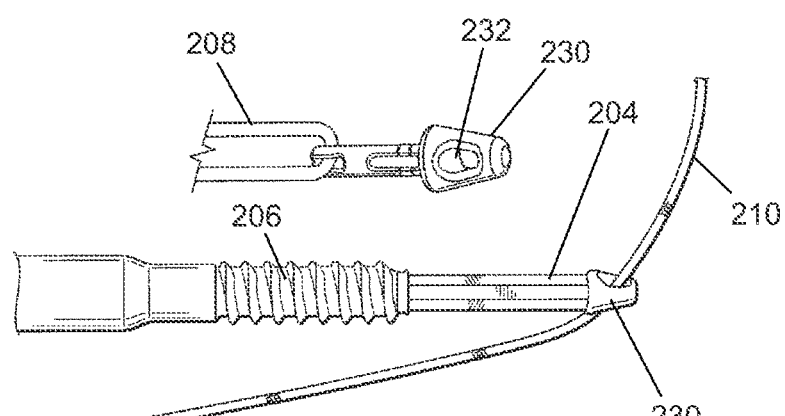
FIG. 91 is an expanded view of the distal portion of the objects of FIG. 89 with suture loaded in preparation for use.

FIGS. 89 through 91 depict another prior art device 200. Cannulated driver 200 has a handle portion 202 and a distal hexagonal portion 204 that protrudes beyond anchor 206. Suture 208 in the cannulation of driver 200 is looped through aperture 231 of implant 230. Tension applied to the proximal ends of suture 208 retains implant 230 in the distal end of hexagonal portion 204. As depicted in FIG. 91, during use one or more sutures 210 are threaded through eyelet 232 of implant 230. During use the distal portion of hexagonal portion 204 with implant 230 mounted to its distal end is inserted into a prepared socket and sutures 210 are tensioned to move the graft to its intended position. Thereafter, anchor 206 is screwed into the socket; suture 208 is released thereby freeing implant 230 from driver 200; and driver 200 is removed, following which the sutures are trimmed proximal to anchor 206. Although implant 230 is pivotably mounted to the distal end of hexagonal drive portion 204, due to friction between implant 230 and the distal end of hexagonal drive portion 204 in which it is retained by tension in suture 208, some level of torque is transmitted to implant 230, and therethrough to suture(s) 210. This torque transmitted to implant 230 may cause twisting of suture(s) 210 leading to improper tensioning and graft shift, a negative effect referred to in the art as "suture spin".

The present invention attempts to address these aforenoted problems in the art. To that end, FIGS. 1A through 1C and 2A and 2B depict a cannulated driver 1500 for a knotless anchor system of the instant invention. Driver 1500 has a proximal handle 1502 in which is formed a proximal cylindrical recess 1504, and off-axis lateral holes 1506, and a tubular distal portion 1510 having at its distal end tubular drive element 1512. The distal portion 1514 of drive element 1512 is configured to be complementary to internal drive features 1602 in the proximal portion of the lumen of cannulated threaded anchor 1600; accordingly, torque supplied by driver 1500 is transmitted to anchor 1600. The distal portion of drive element 1512 may be fabricated in a variety of sizes, shapes, configurations and lumen sizes to suit a variety of anchors 1600, the requirements for a particular anchor 1600 depending on its size, configuration and material properties. For example, the complementary drive elements may take the form of an internally or externally positioned hexagonal or square drive, an internal or external spline, or slots positioned internal or external to the anchor. However, the present invention contemplates alternate cooperating configurations and thus is not limited to any one particular embodiment.

Referring now to FIGS. 3 through 9, cannulated tensioning device 1400 has a proximal hub 1402 optionally provided with a distal cylindrical portion 1404 in which are formed off-axis lateral grooves 1406, and cleats 1408 formed in the proximal rim of proximal hub 1402.

Tensioning device 1400 has a tubular middle portion 1410, and a tubular distal portion 1412, distal portion 1412 having a diameter 1414 and length 1416. Diameter 1414 is selected such that distal portion 1412 may be slidably positioned within distal drive element 1512 of cannulated driver 1500. Length 1416 is determined such that when tensioning device 1400 is positioned within the lumen of the cannulated driver 1500, distal portion 1412 of tensioning device 1400 protrudes beyond distal drive element 1512 of driver 1500 a sufficient distance so that when anchor 1600 is mounted on distal drive element 1512 and distal portion 1412 is inserted to the full depth of a suitable socket formed in bone, anchor 1600 is still proximal to and clear of the socket. Elongate wire element 1302 having at its distal end loop 1304 and at its proximal end polymeric element 1306 forming a pull tab forms a loading loop 1300 for drawing sutures into the lumens of tubular members 1410 and 1412.

Figure 2A:
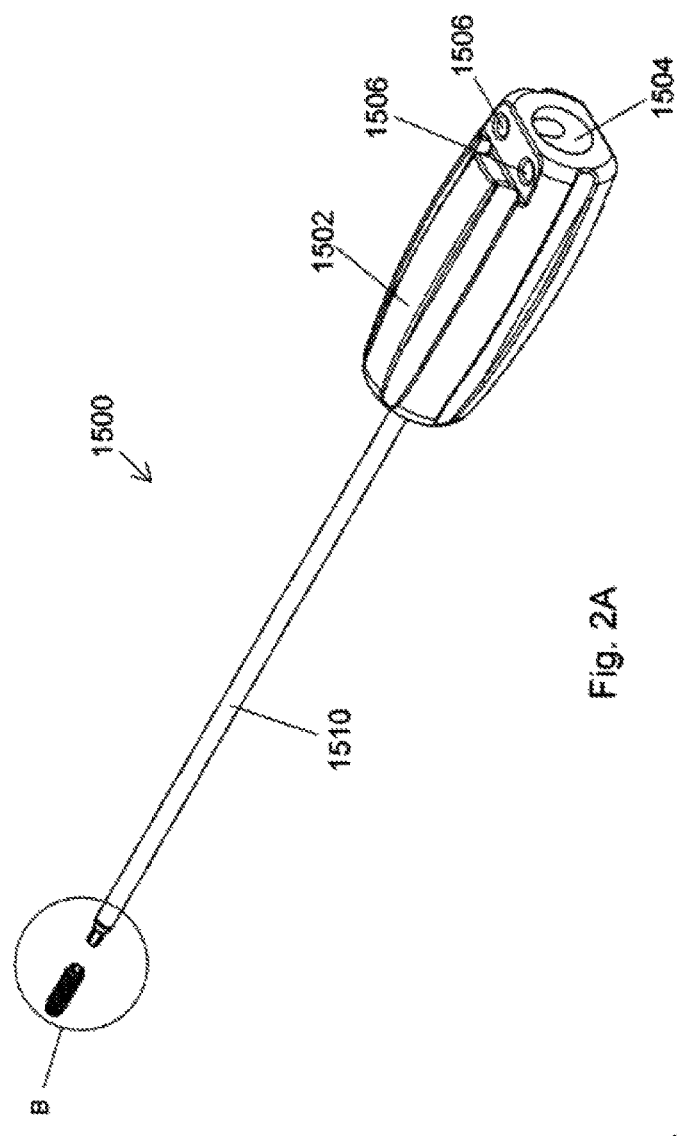
FIG. 2A is a perspective view of the objects of FIG. 1A.
Figure 2B:
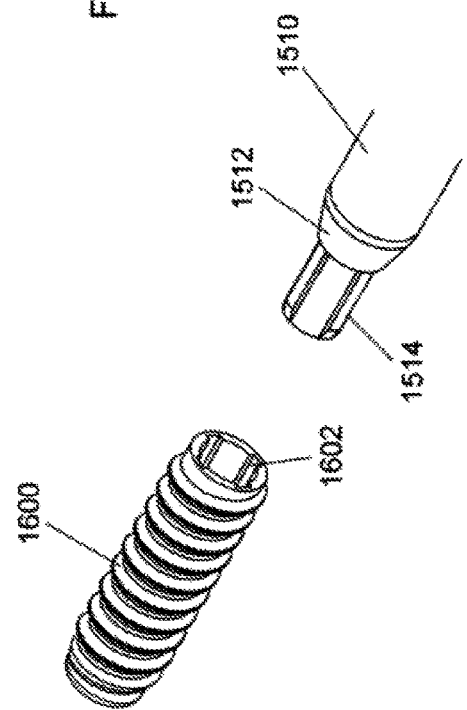
FIG. 2B is an expanded view of the distal portion of the objects of FIG. 2A at location B.
Figure 8:
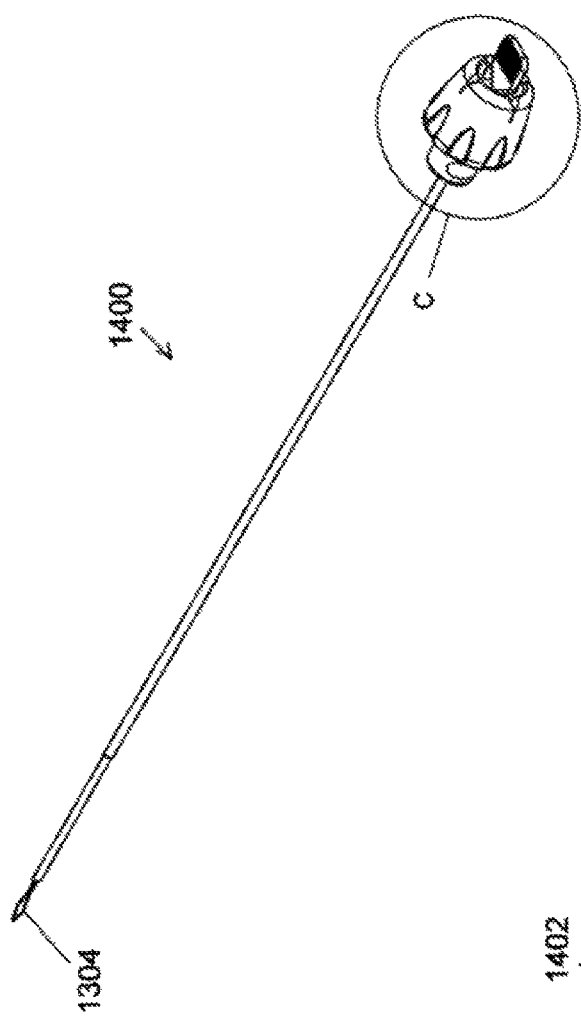
FIG. 8 is a perspective view of the tensioning device of FIG. 3.
Figure 9:
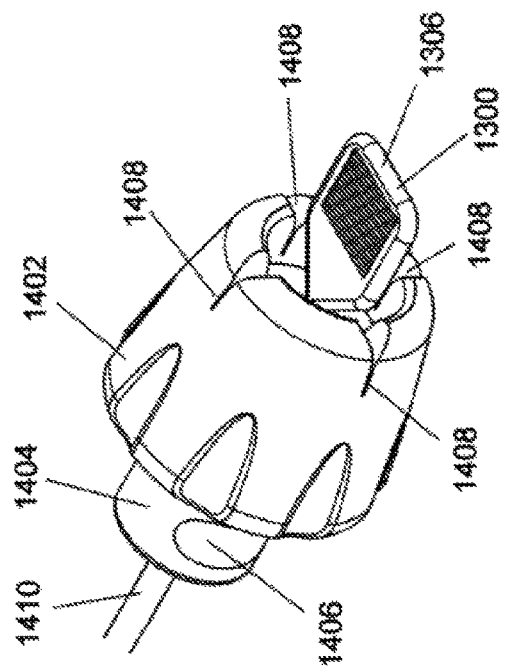
FIG. 9 is an expanded view of the objects of FIG. 8 at location C.
Figure 11:
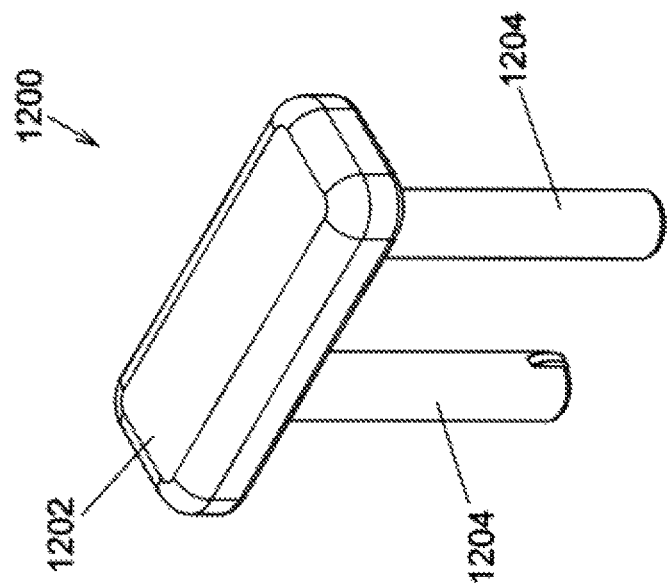
FIG. 11 is a perspective view of the objects of FIG. 10.
Figure 10:
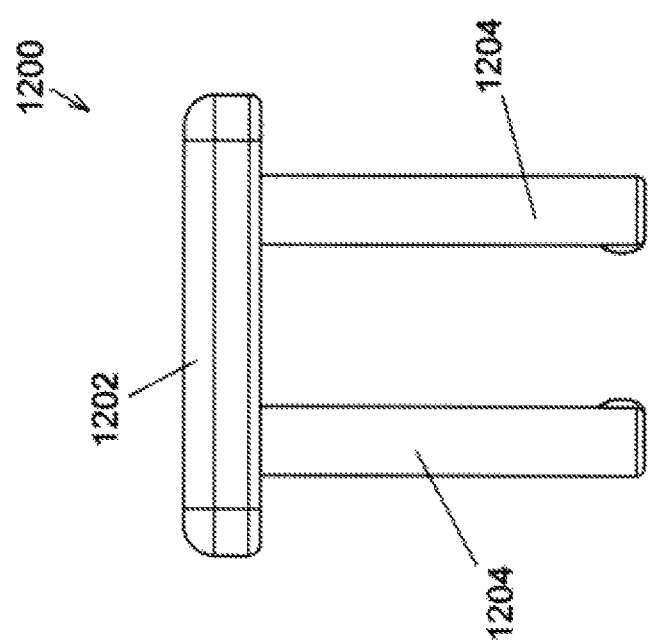
FIG. 10 is a side elevational view of a key for an implant placement system of the present invention.

FIGS. 10 and 11 depict an illustrative embodiment of removable key 1200 that may serve to prevent relative axial and rotational movement between the cannulated driver and the tensioning device. In this embodiment, key 1200 has a planar portion 1202 and cylindrical portions 1204 that are sized and spaced such that cylindrical portions 1204 may be inserted into off-axis lateral holes 1506 of handle 1502 of cannulated driver 1500.

Figure 12:
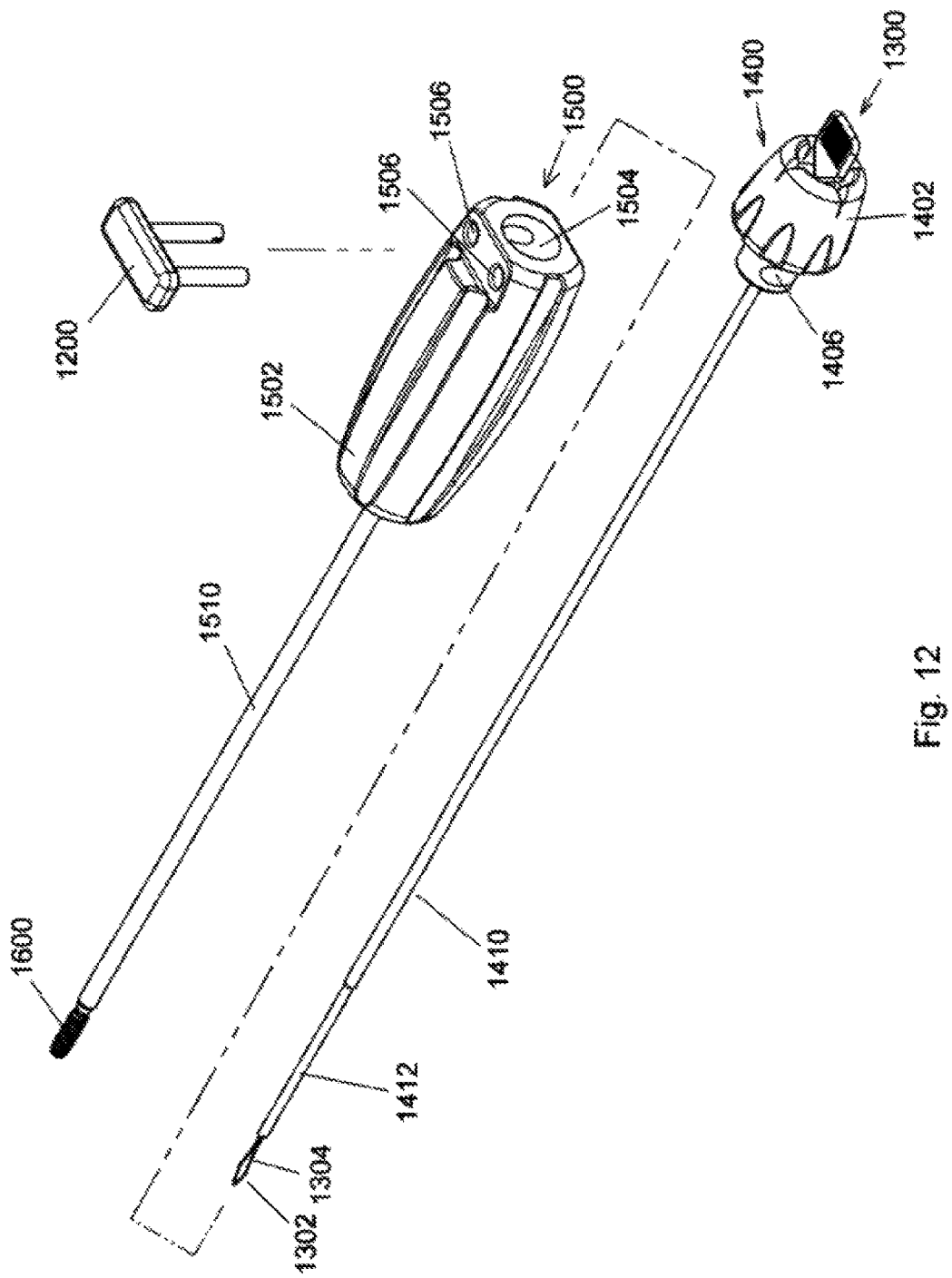
FIG. 12 is an exploded view of the assembly of a first embodiment of an implant placement system of the present invention.
Figure 13:
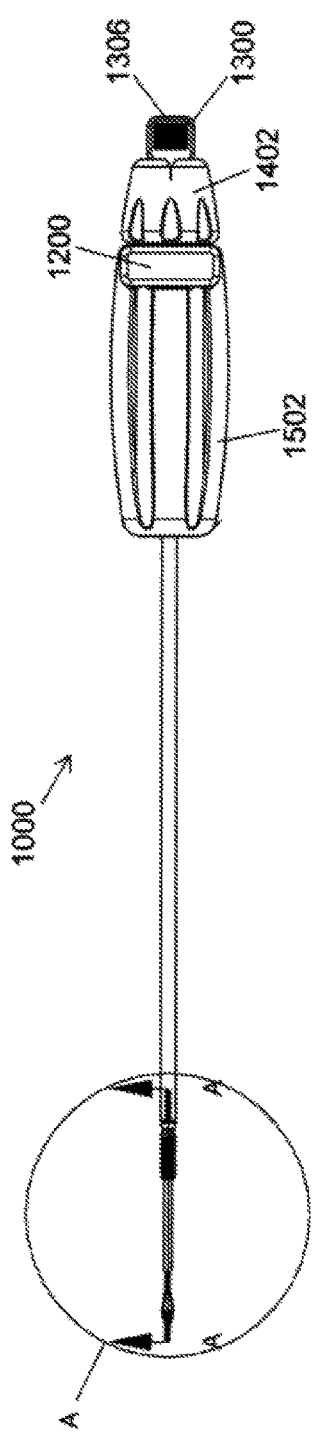
FIG. 13 is a plan view of a fully assembled first embodiment of an implant placement system of the instant invention.
Figure 14:
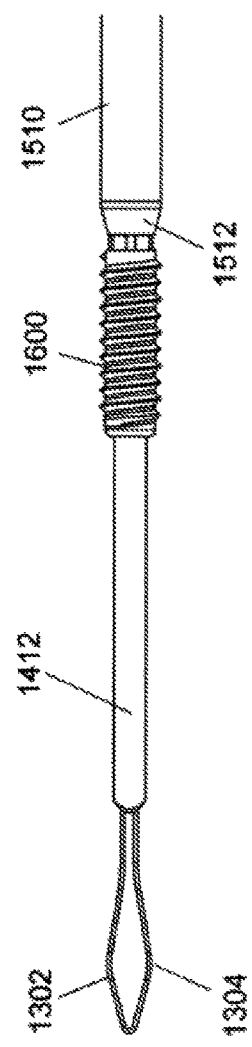
FIG. 14 is an expanded view of the distal portion of FIG. 13 at location A.
Figure 15:
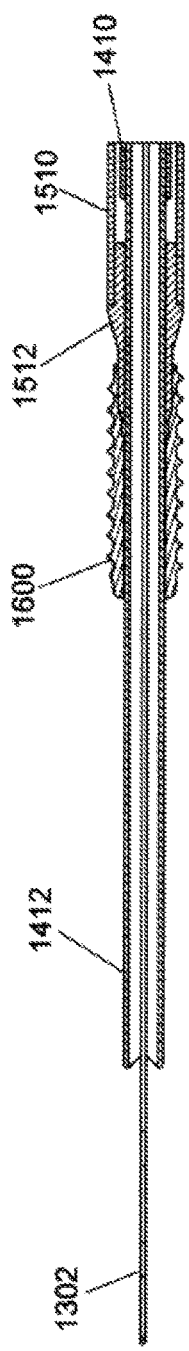
FIG. 15 is an expanded side elevational sectional view of the objects of FIG. 13 at location A-A.
Figure 18:
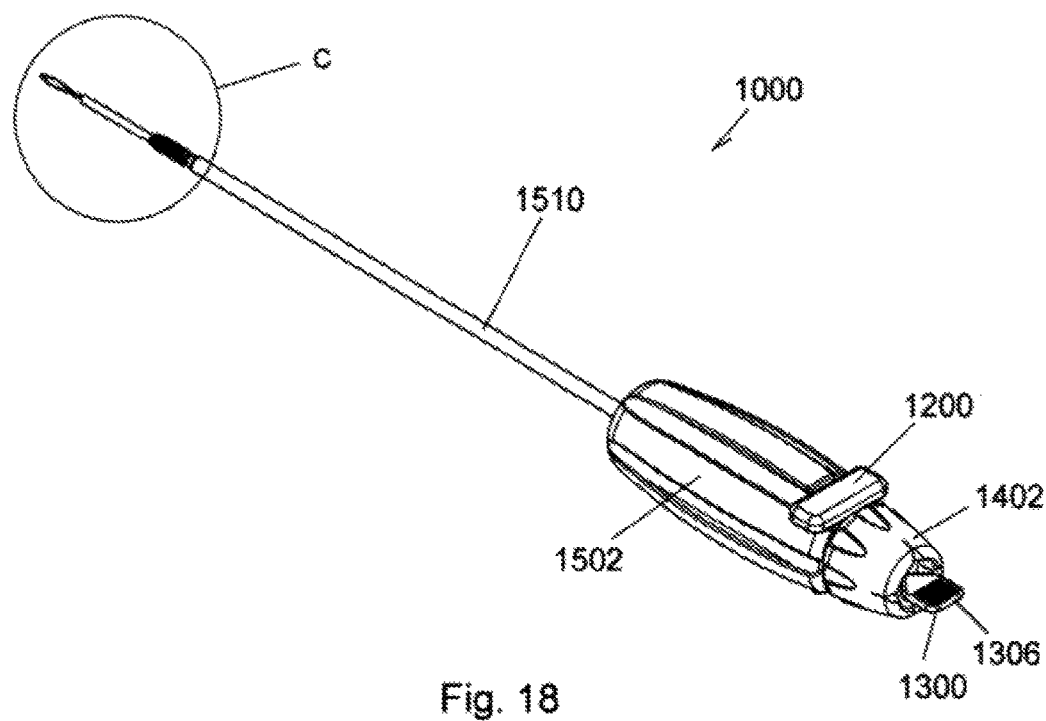
FIG. 18 is a perspective view of the objects of FIG. 13.
Figure 19:
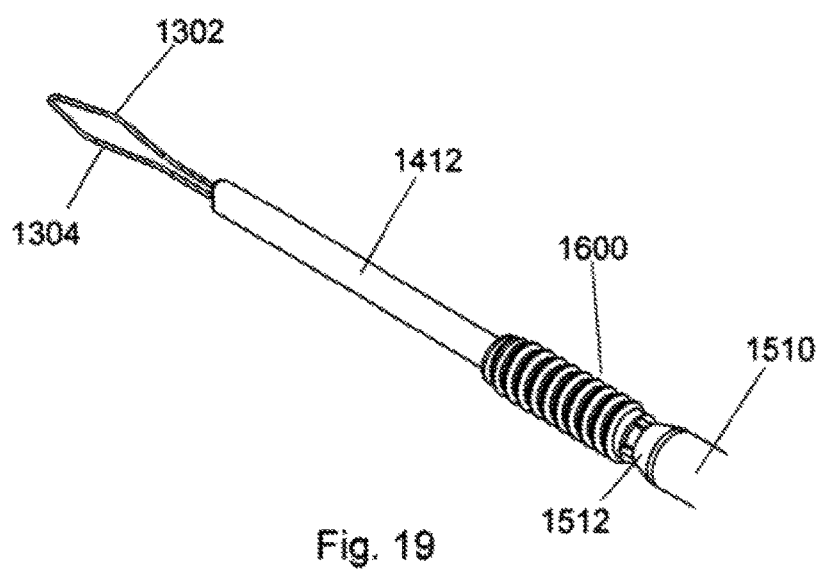
FIG. 19 is an expanded view of the objects of FIG. 13 at location C.

FIG. 12 depicts cannulated driver 1500 with anchor 1600 loaded thereto, tensioning device 1400 with loading loop 1300 positioned for loading a suture, and key 1200 prior to mounting of driver 1500 to tensioning device 1400 in preparation for use. When driver 1500 is mounted to tensioning device 1400, off-axis slots 1406 of handle 1402 of tensioning device 1400 are aligned with off-axis holes 1506 of handle 1502 of driver 1500 and cylindrical portions 1204 of key 1200 are inserted into the passages so formed. Positioning of key 1200 in this manner prevents axial and rotational movement of tensioning device 1400 relative to driver 1500. FIGS. 13 through 19 depict knotless suture anchor system 1000 of the instant invention prepared for use with key 1200 and loading loop 1300 in place.

Figure 20:
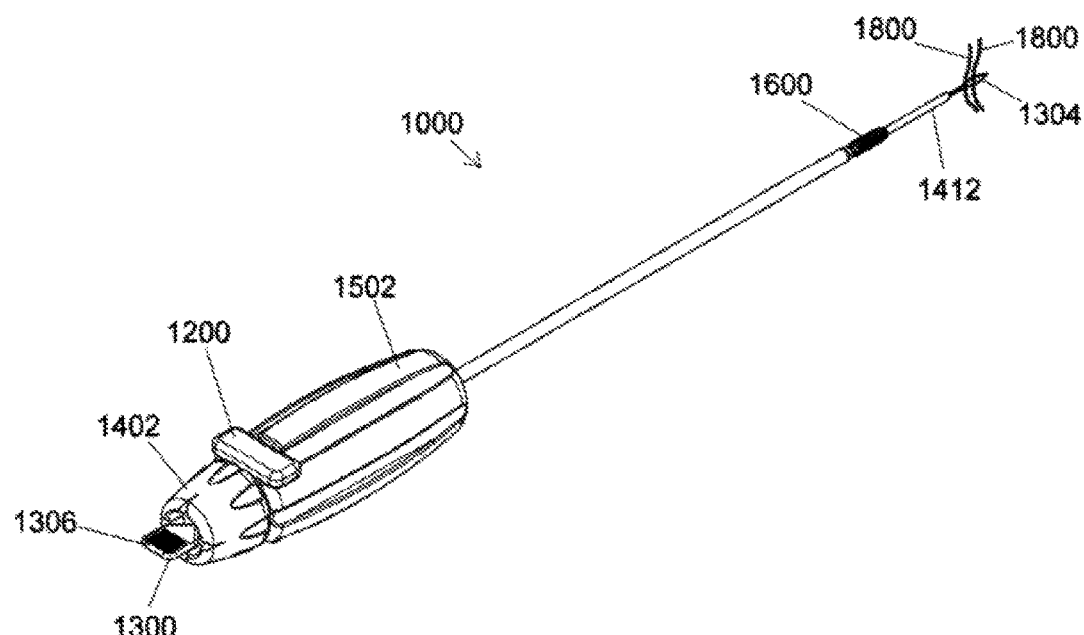
FIG. 20 is a perspective view of a first embodiment implant placement system with sutures being loaded into the system.
Figure 21:
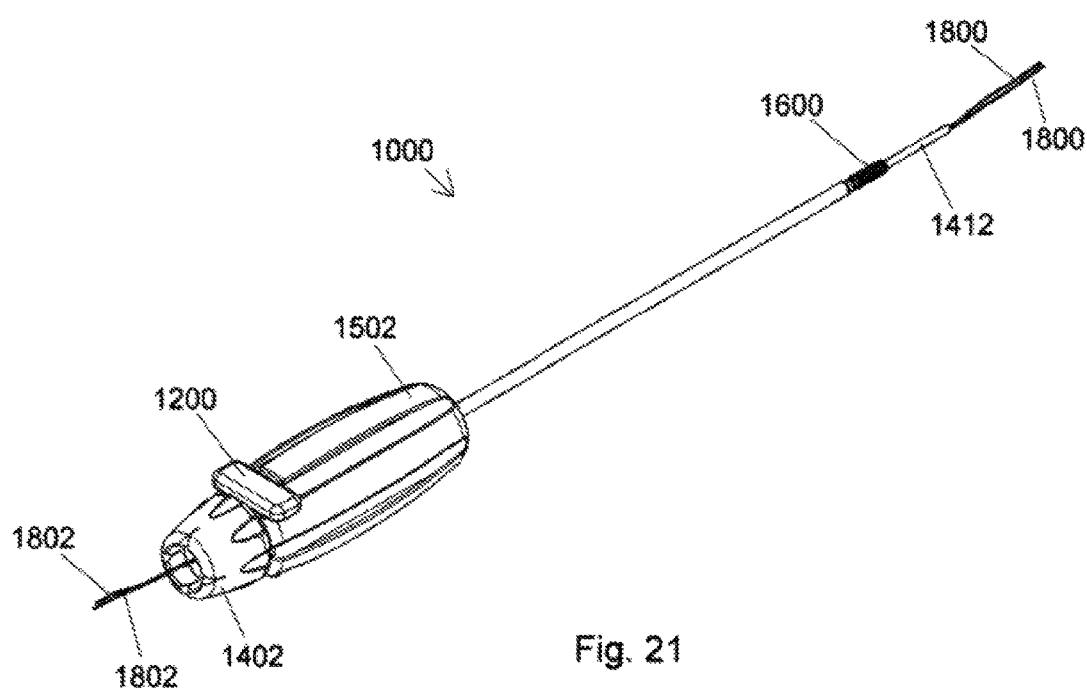
FIG. 21 is a perspective view of the first embodiment implant placement system with the sutures loaded.

Sutures 1800 are loaded into system 1000 by placing the proximal ends of sutures 1800 in distal loop 1304 of loading loop 1300 as depicted in FIG. 20. Tab 1306 of loading loop 1300 is withdrawn proximally until proximal ends 1802 of sutures 1800 extend proximally beyond hub 1402 of tensioning device 1400 as depicted in FIG. 21.

Figure 22:
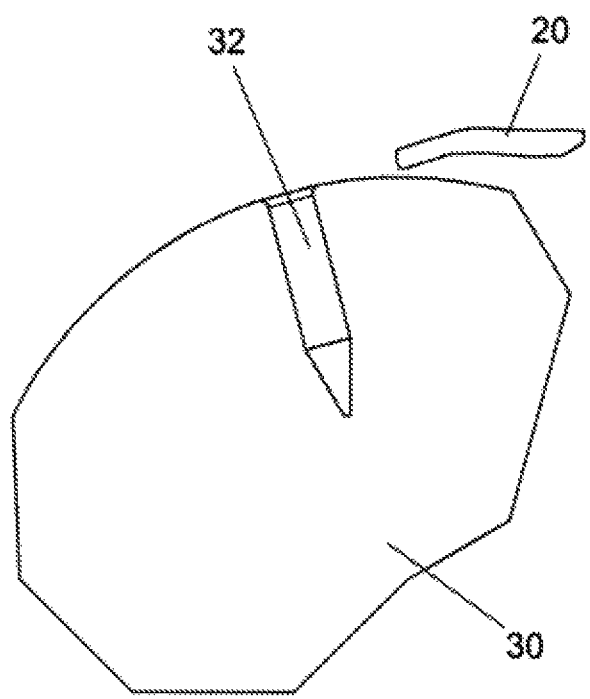
FIG. 22 schematically depicts a socket placed in a bone prior to the placement of an implant.
Figure 23:
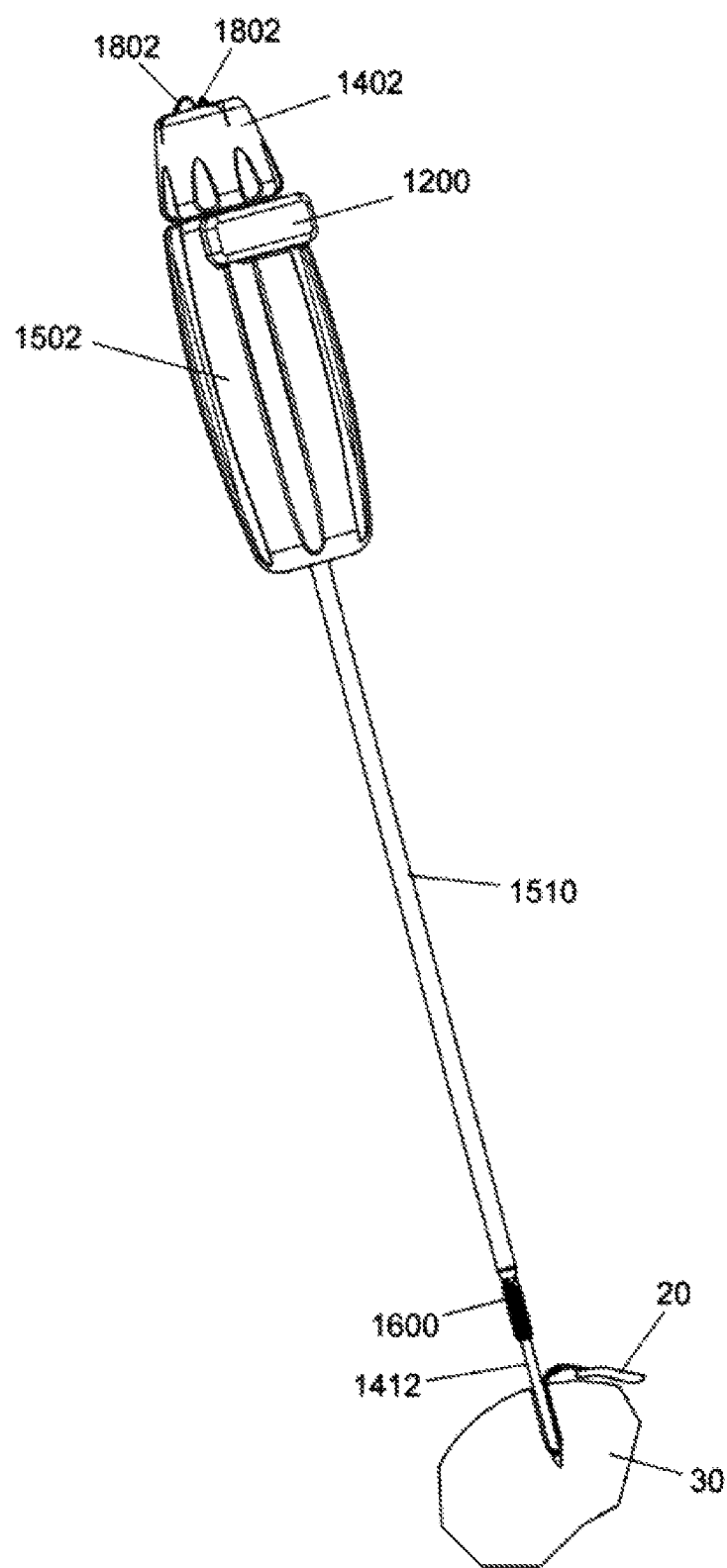
FIG. 23 depicts the first embodiment implant placement system positioned for the first step of implant placement.
Figure 24:
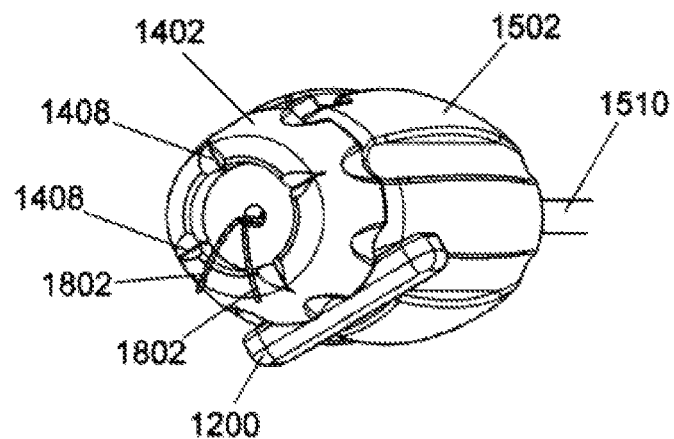
FIG. 24 depicts the proximal portion of the first embodiment implant placement system during the first step of implant placement.
Figure 25:
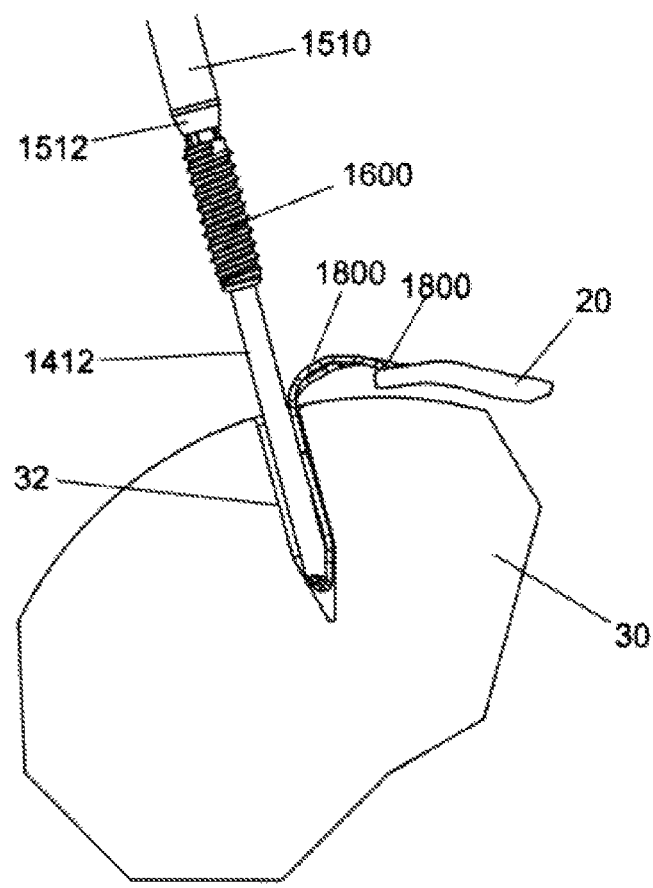
FIG. 25 depicts the distal portion of the first embodiment implant placement system during the first step of implant placement.
Figure 26:
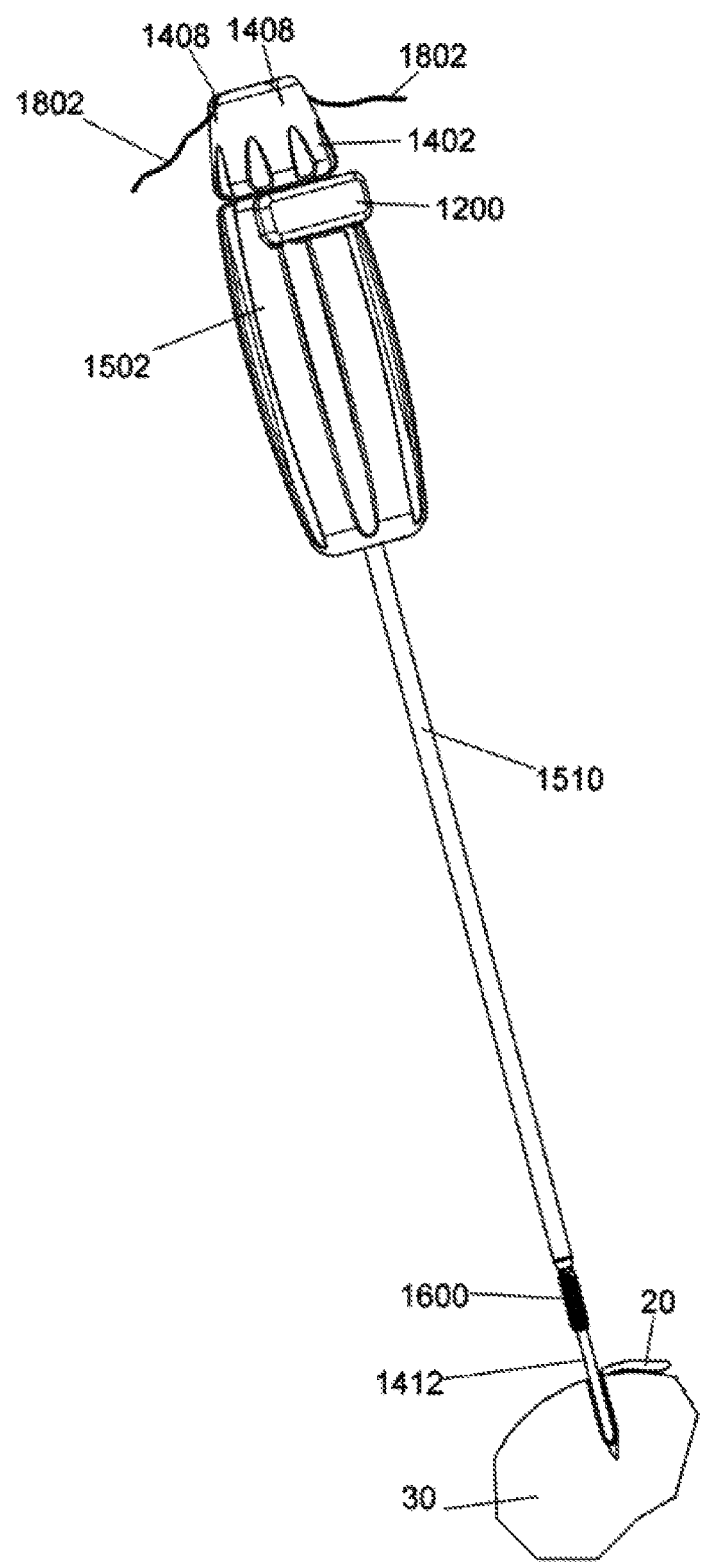
FIG. 26 depicts the first embodiment implant placement system positioned for the second step of implant placement.
Figure 27:
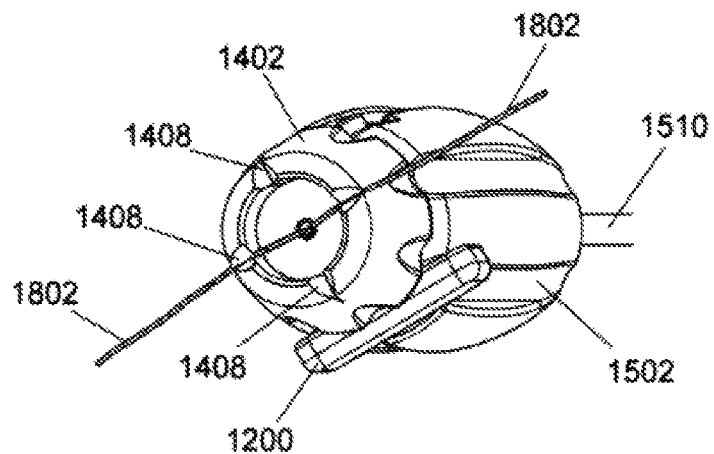
FIG. 27 depicts the proximal portion of the embodiment implant placement system during the second step of implant placement.
Figure 28:
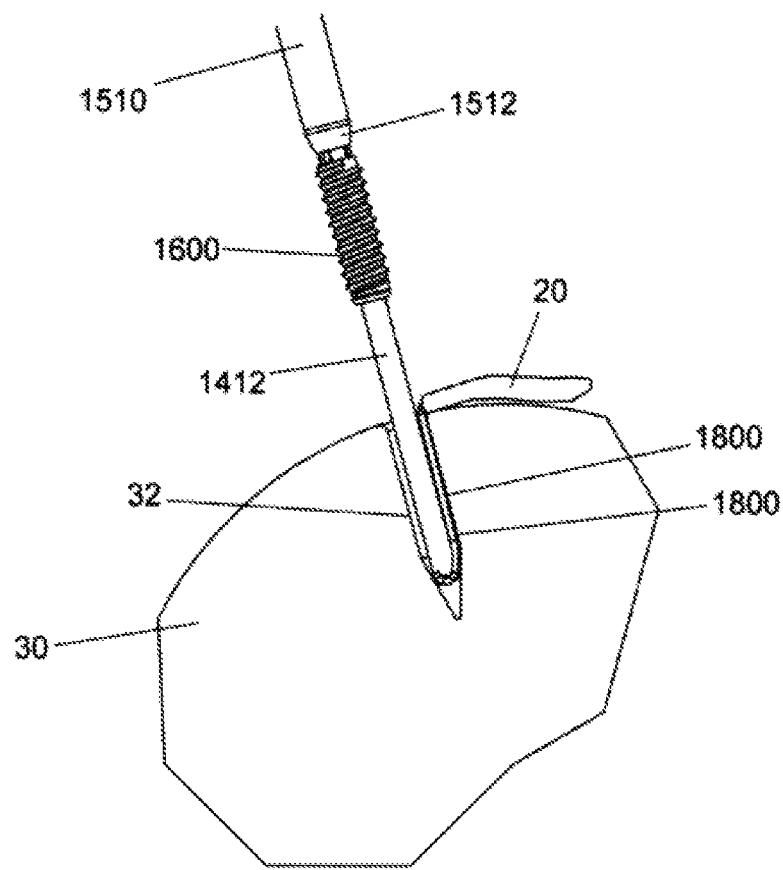
FIG. 28 depicts the distal portion of the first embodiment implant placement system during the second step of implant placement.
Figure 29:
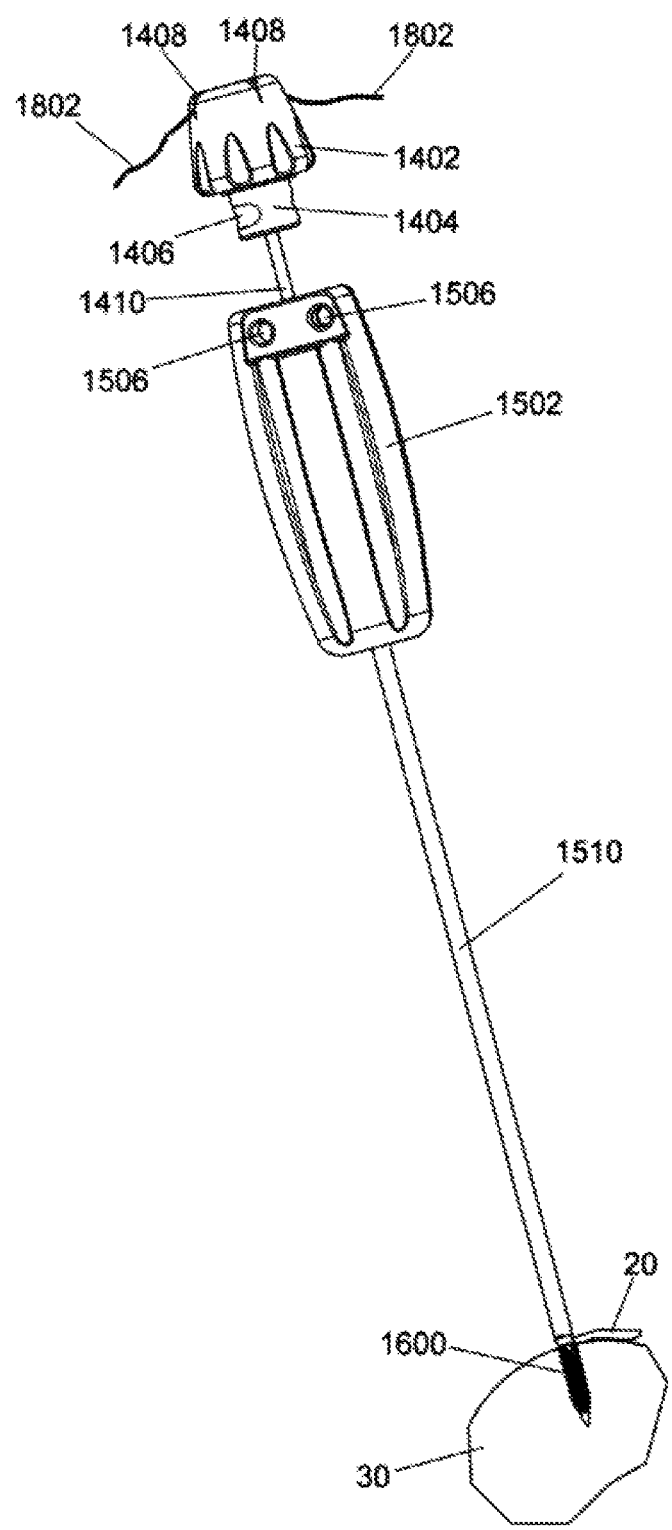
FIG. 29 depicts the first embodiment implant placement system positioned for the third step of implant placement.
Figure 30:
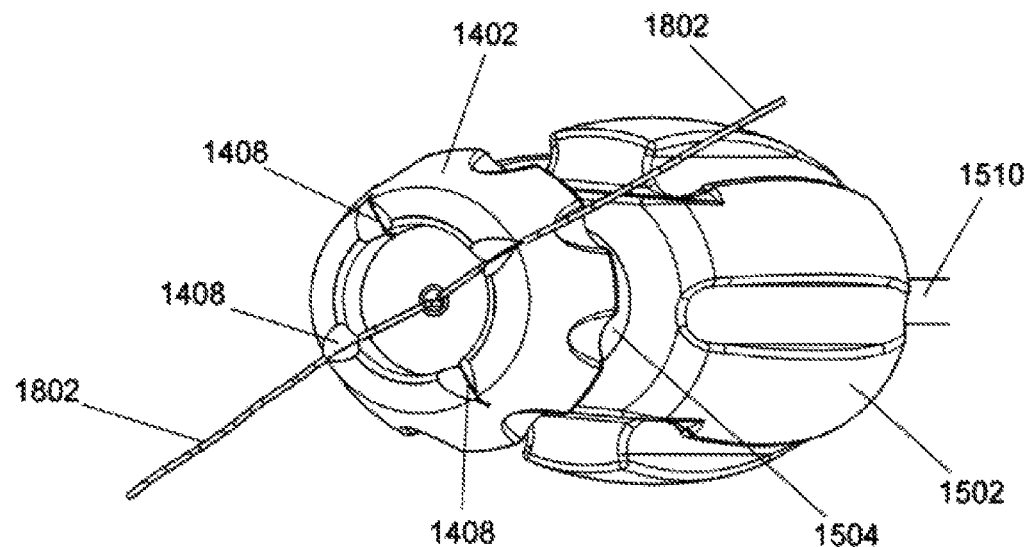
FIG. 30 depicts the proximal portion of the first embodiment implant placement system during the second step of implant placement.
Figure 31:
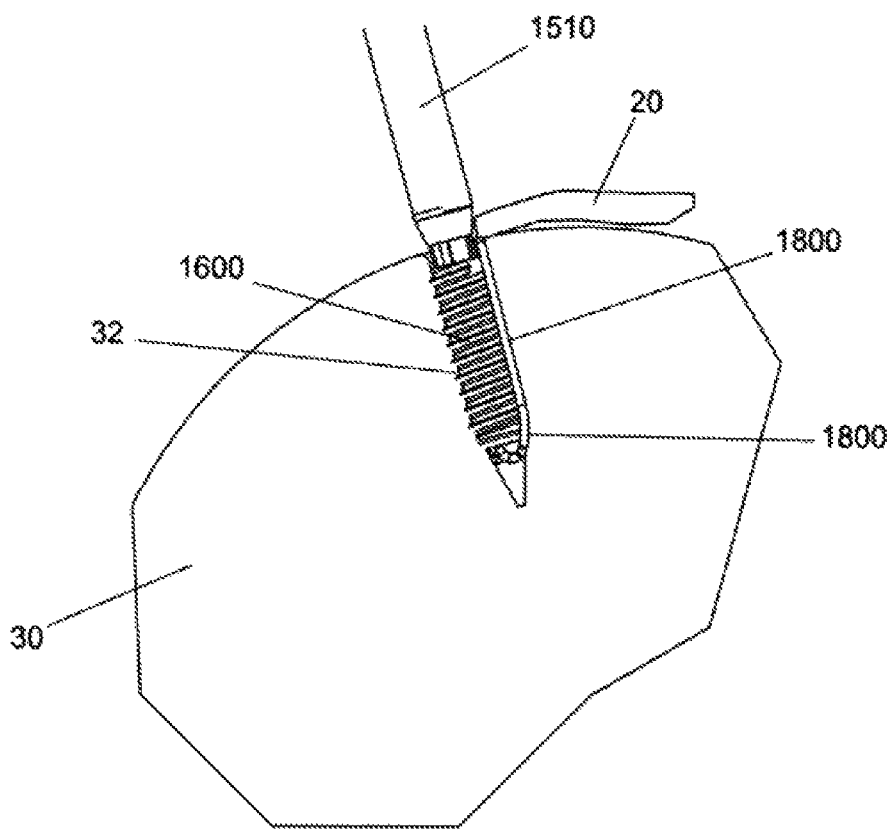
FIG. 31 depicts the distal portion of the first embodiment implant placement system during the third step of implant placement.
Figure 32:
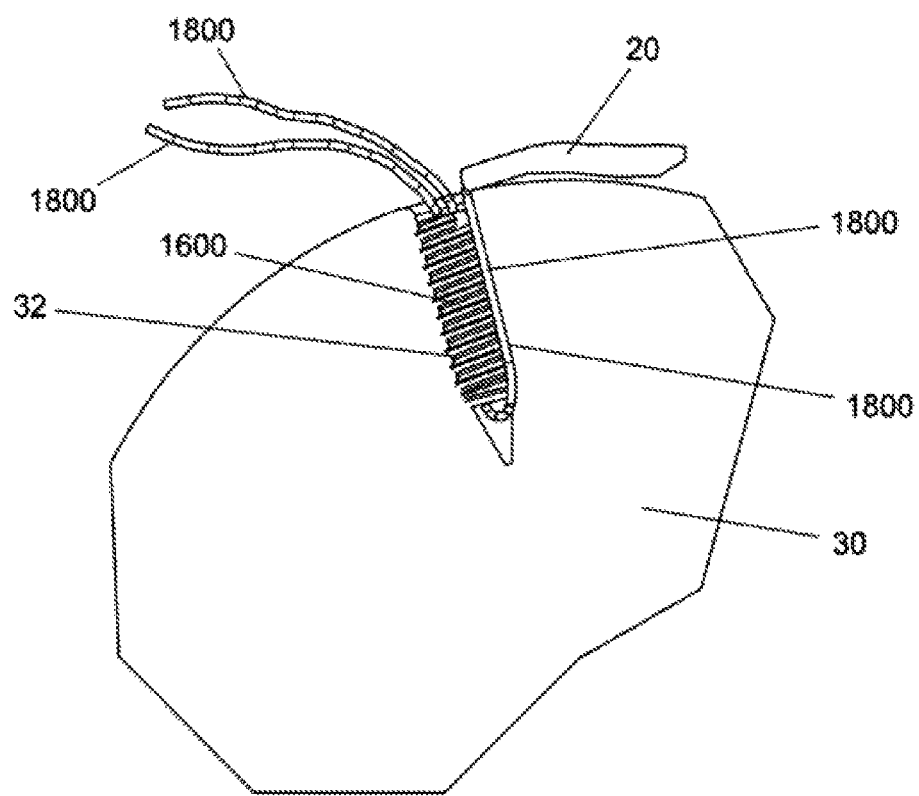
FIG. 32 depicts the site at the completion of implant placement using an implant placement system of the instant invention.
Figure 33:
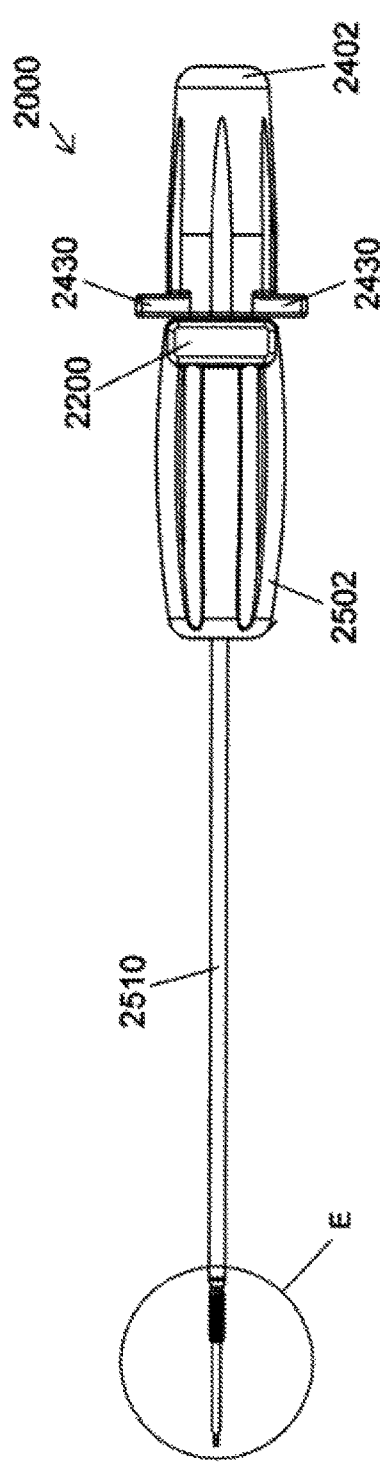
FIG. 33 is a plan view of a second embodiment of an implant placement system of the instant invention wherein the tubular distal portion of the tensioning device is replaced by a rod having formed at its distal end a sharpened fork portion.
Figure 34:
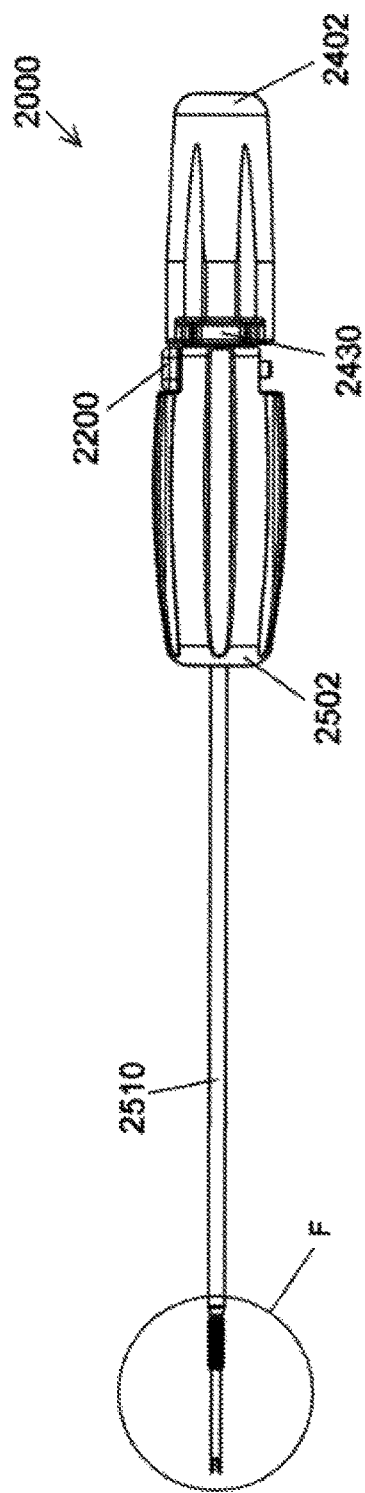
FIG. 34 is a side elevational view of the objects of FIG. 33.
Figure 35:
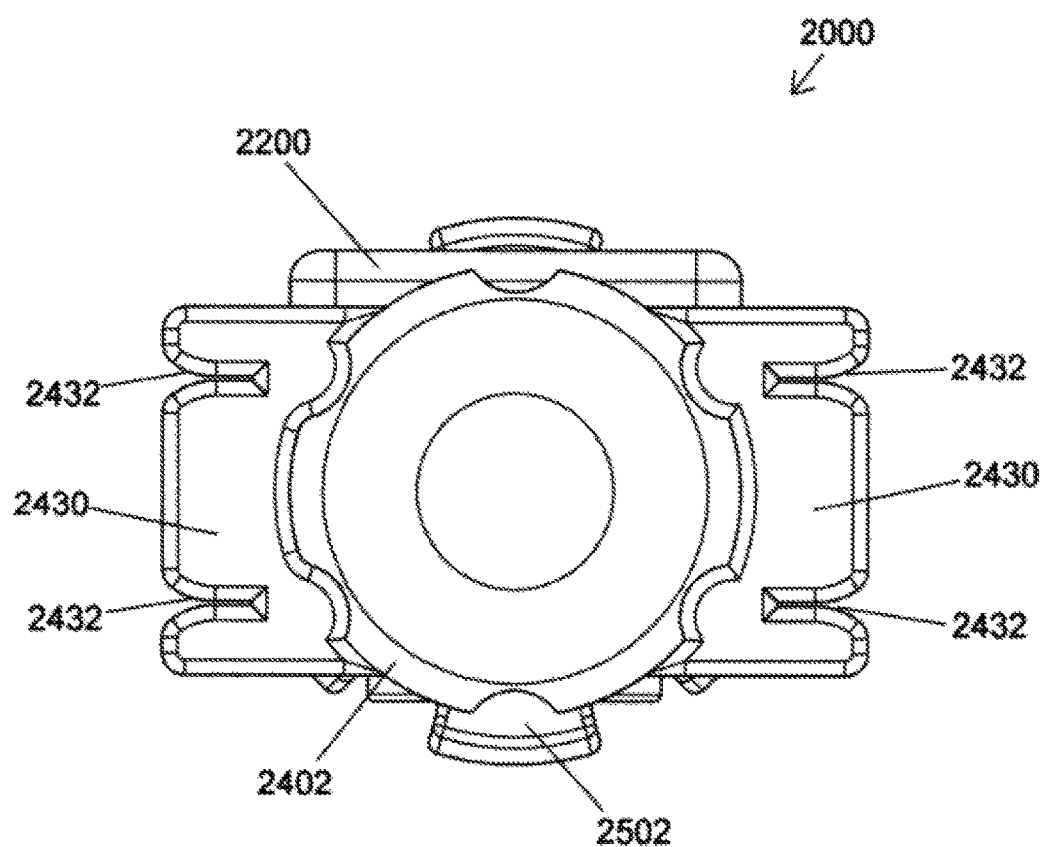
FIG. 35 is an expanded proximal end view of the objects of FIG. 33.
Figure 36:
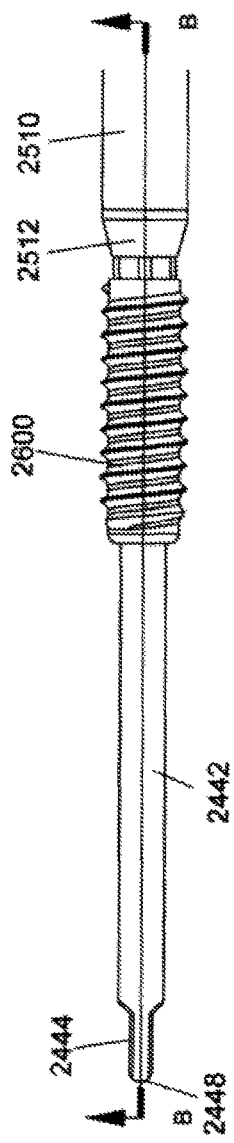
FIG. 36 is an expanded plan view of the distal portion of the elements of FIG. 33.
Figure 37:
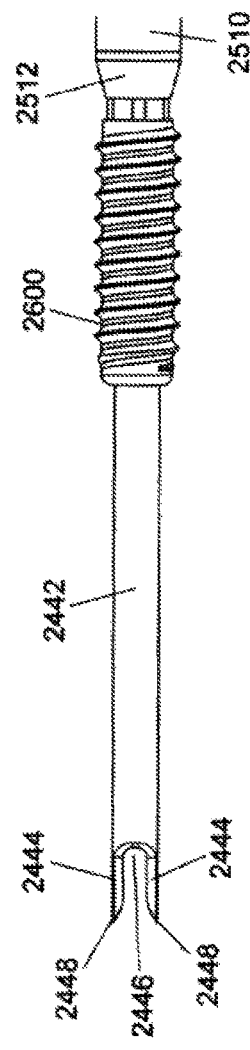
FIG. 37 is a side elevational view of the objects of FIG. 36.
Figure 38:
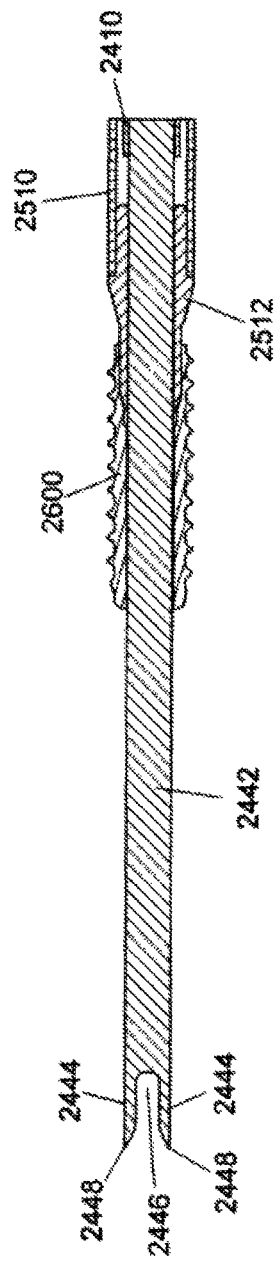
FIG. 38 is a sectional view of the objects of FIG. 36 at location B-B.
Figure 39:
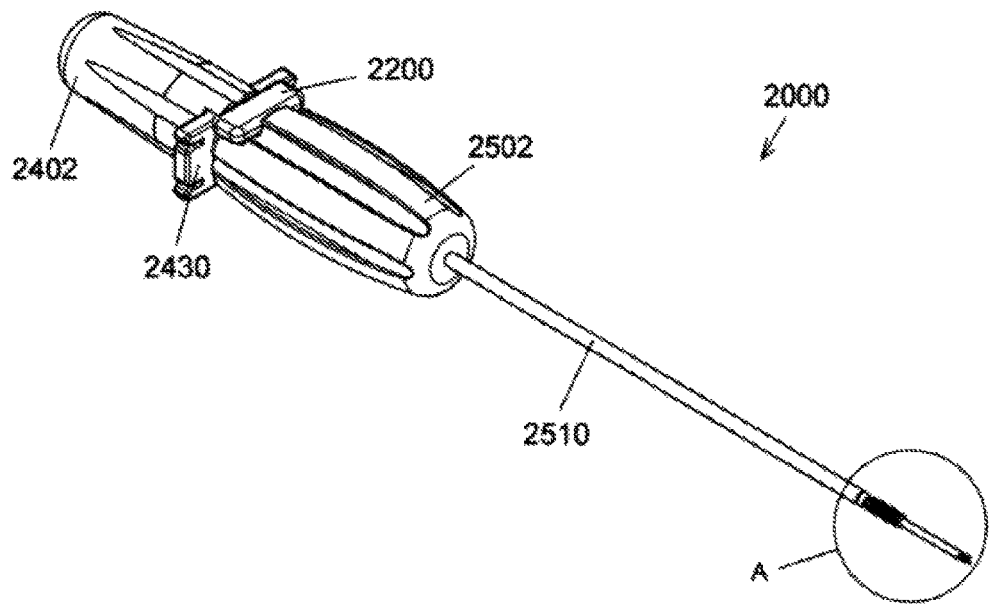
FIG. 39 is a distal perspective view of the objects of FIG. 33.
Figure 40:
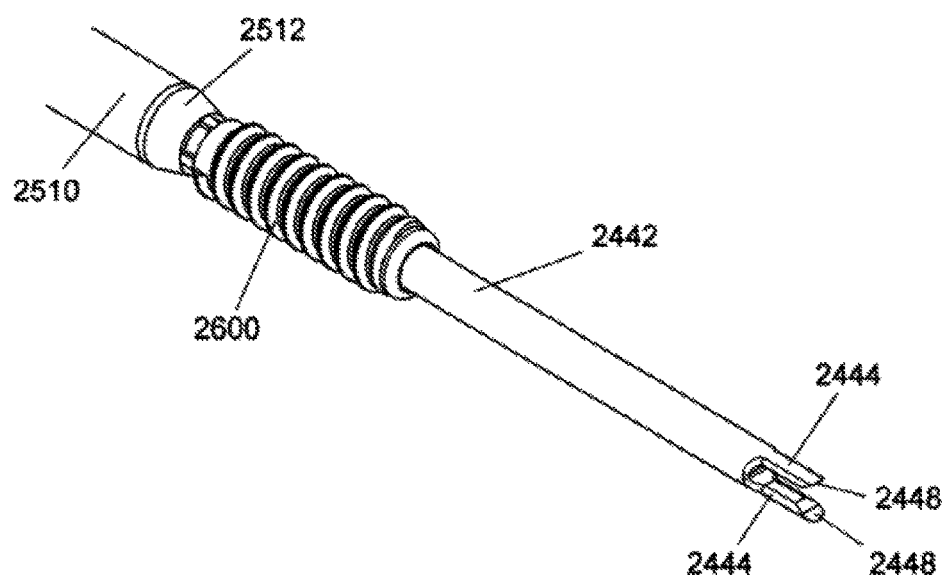
FIG. 40 is an expanded view of the objects of FIG. 39 at location A.
Figure 41:
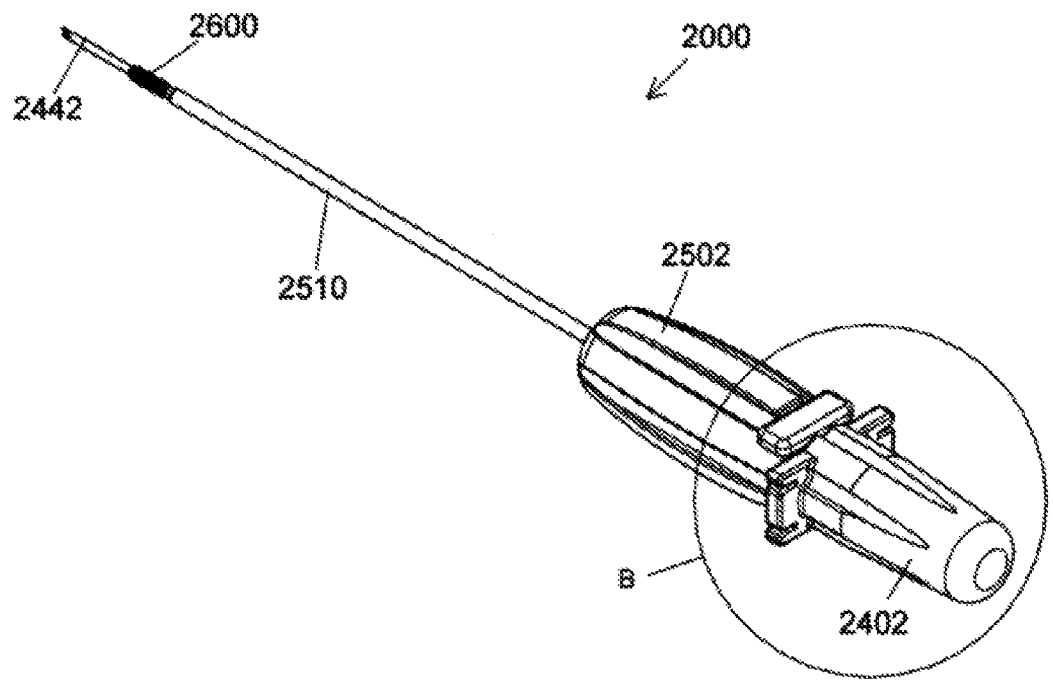
FIG. 41 is a proximal perspective view of the objects of FIG. 33.
Figure 42:
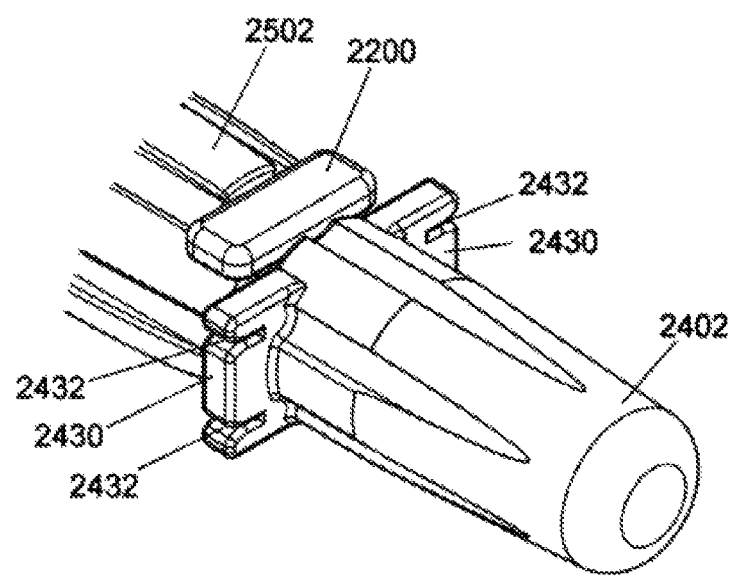
FIG. 42 is an expanded view of the objects of FIG. 41 at location B.

The present invention may be used to secure any type of soft tissue, graft, or tendon, such as, for example, a biceps tendon or a rotator cuff. An illustrative method of fixation according to the principles of the instant invention is depicted in FIGS. 22 through 32. FIG. 22A schematically depicts a socket 32 formed by drilling or punching in bone 30, and a graft 20 to be affixed to bone 30. Sutures 1800 are passed through graft 20 in a usual manner; and the sutures loaded into system 1000 as previously described and depicted in FIGS. 20 and 21, such that suture proximal ends 1802 are accessible to the surgeon. Subsequently, distal tubular portion 1412 of tensioning device 1400 is inserted into socket 32 as depicted in FIGS. 23 through 25, the distal end of tubular portion 1412 contacting the bottom surface of socket 32. Thereafter, referring to FIGS. 26 through 28, the surgeon grasps proximal ends 1802 of sutures 1800 and withdraws them proximally so as to advance graft 20 towards socket 32. When graft 20 is in the desired position, proximal ends 1802 of sutures 1800 are secured in cleats 1408 to maintain the graft position. So long as proximal ends 1802 of sutures 1800 remain securely cleated and the distal end of tubular element 1412 is maintained in contact with the bottom surface of socket 32, the position of graft 20 will not change. The surgeon may adjust sutures 1800 as required to achieve optimal placement of graft 20. When this optimal placement of graft 20 has been achieved, while maintaining contact between the distal end off distal tubular element 1412 and the bottom of socket 32, the surgeon removes key 1200 from system 1000 so as to allow axial and rotational movement of driver 1500. The surgeon then advances anchor 1600 to socket 32 and screws the anchor into socket 32 so as to trap sutures 1800 between anchor 1600 and the wall of socket 32 in bone 30 as depicted in FIGS. 29 through 31. When anchor 1600 is fully inserted in socket 32, proximal ends 1802 of sutures 1800 are released from cleats 1408 and system 1000 is withdrawn from the joint, leaving the repair site as depicted in FIG. 32. Subsequently sutures 1800 are cut adjacent to anchor 1600 and the anchor placement is complete.

In an alternate method for anchor placement according to the present invention, the process may be simplified through use of an alternate embodiment system of the present invention in which the sutures are not drawn into a cannulation of the tensioning device, but rather are positioned and retained within a forked portion formed at the distal end of the tensioning device. In this alternate embodiment, sutures do not enter the lumen of the cannulated anchor, but rather wrap around the distal end of the anchor during insertion and are retained in place by friction between the external surfaces of the anchor and the boney surface of the socket at laterally opposed locations.

Alternate embodiment anchor placement system 2000, depicted in FIGS. 33 through 42, is identical to system 1000 in all aspects except as specifically subsequently described. Specifically, cannulated distal tubular element 1412 of system 1000 is replaced by distal element 2442 that is not cannulated and has formed at its distal end elongate laterally opposed, distally extending portions 2444 with sharpened distal ends 2448. Elongate portions 2444 form the tines of a fork with channel 2446 formed between portions 2444. Tensioning device handle 2402 has formed near the distal end of its external surface flanges 2430 wherein are formed slots 2432 which serve as cleats for maintaining the tension of sutures placed therein, flanges 2430 and slots 2432 replacing slots 1408 in hub 1402 of system 1000.

Figure 43:
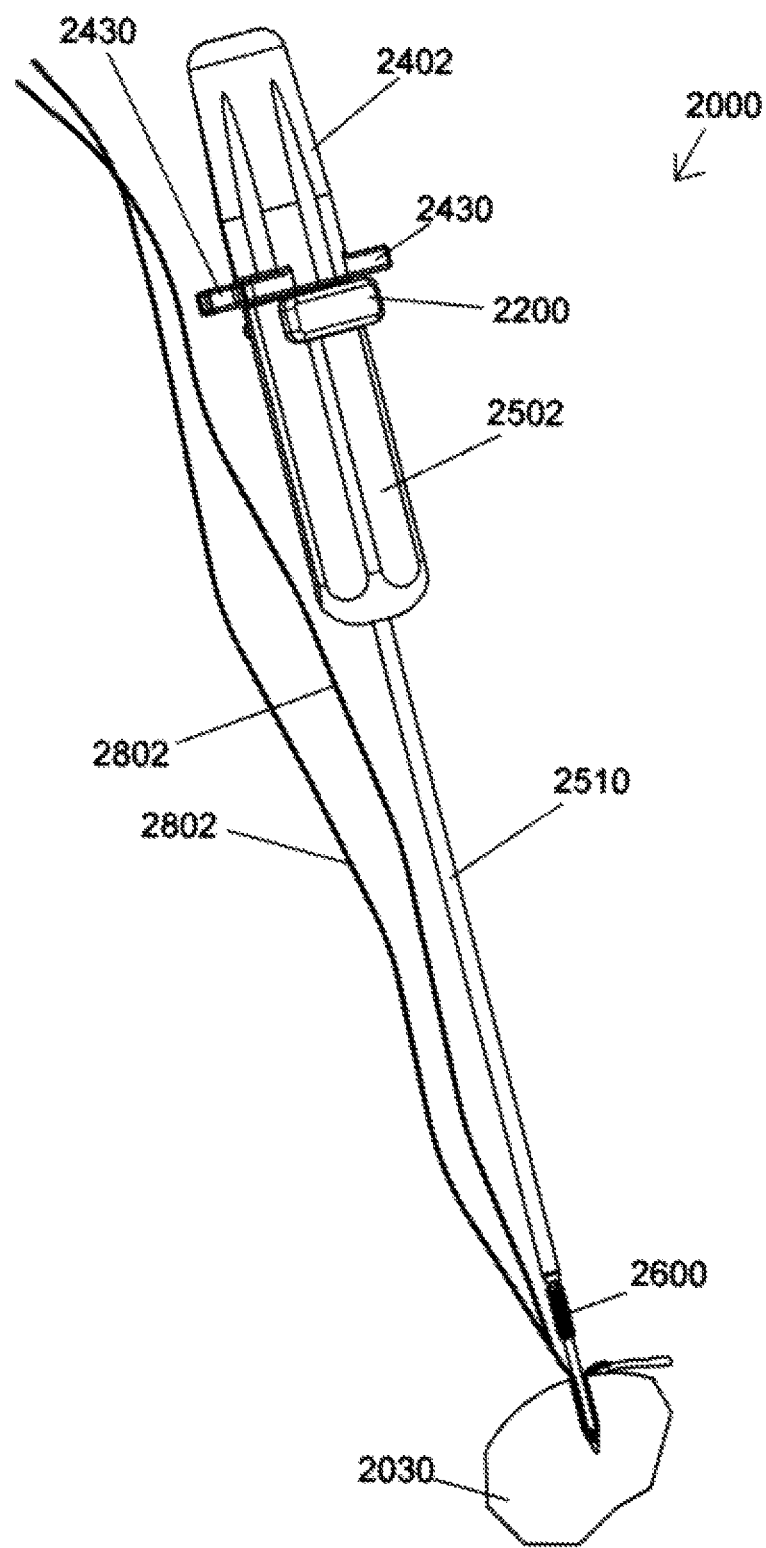
FIG. 43 depicts an alternate embodiment implant system of the present invention in use positioning sutures in a socket for the securing of a graft using an anchor.
Figure 44:
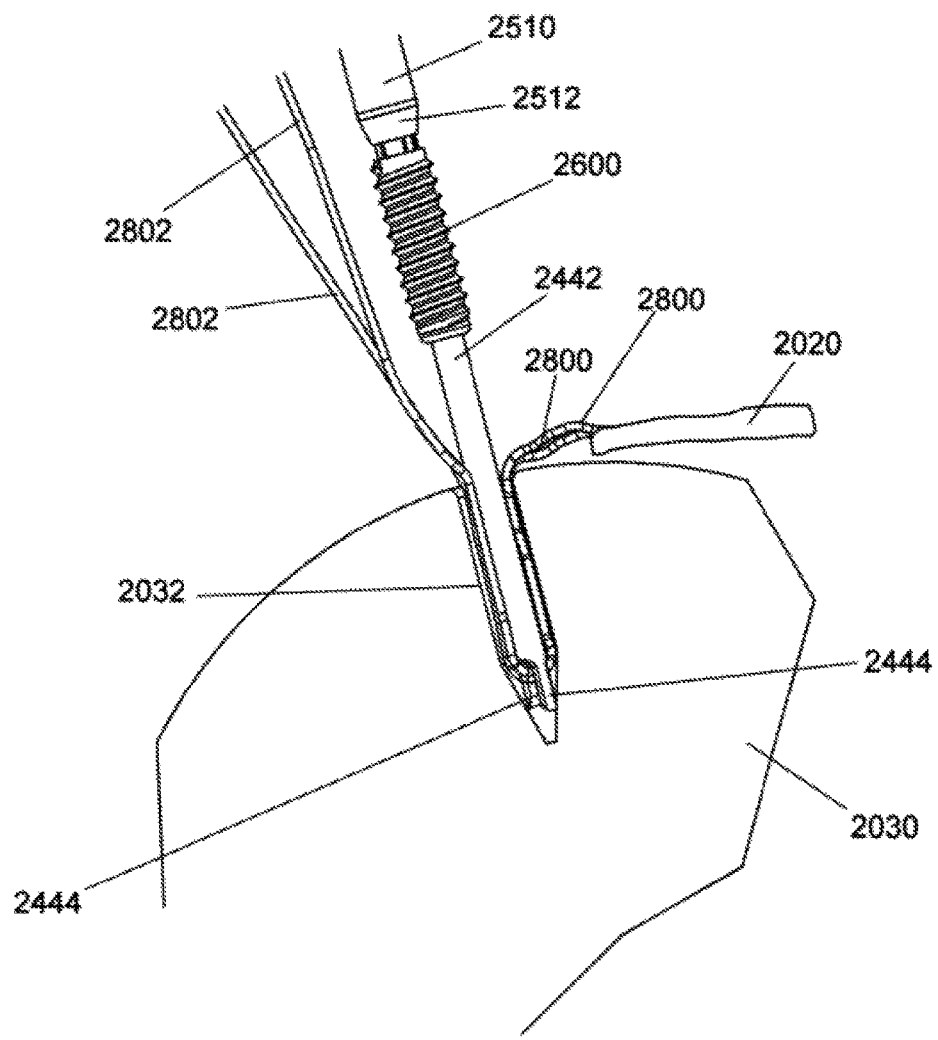
FIG. 44 is an expanded view of the distal portion of the objects of FIG. 43 depicting the placement site.
Figure 45:
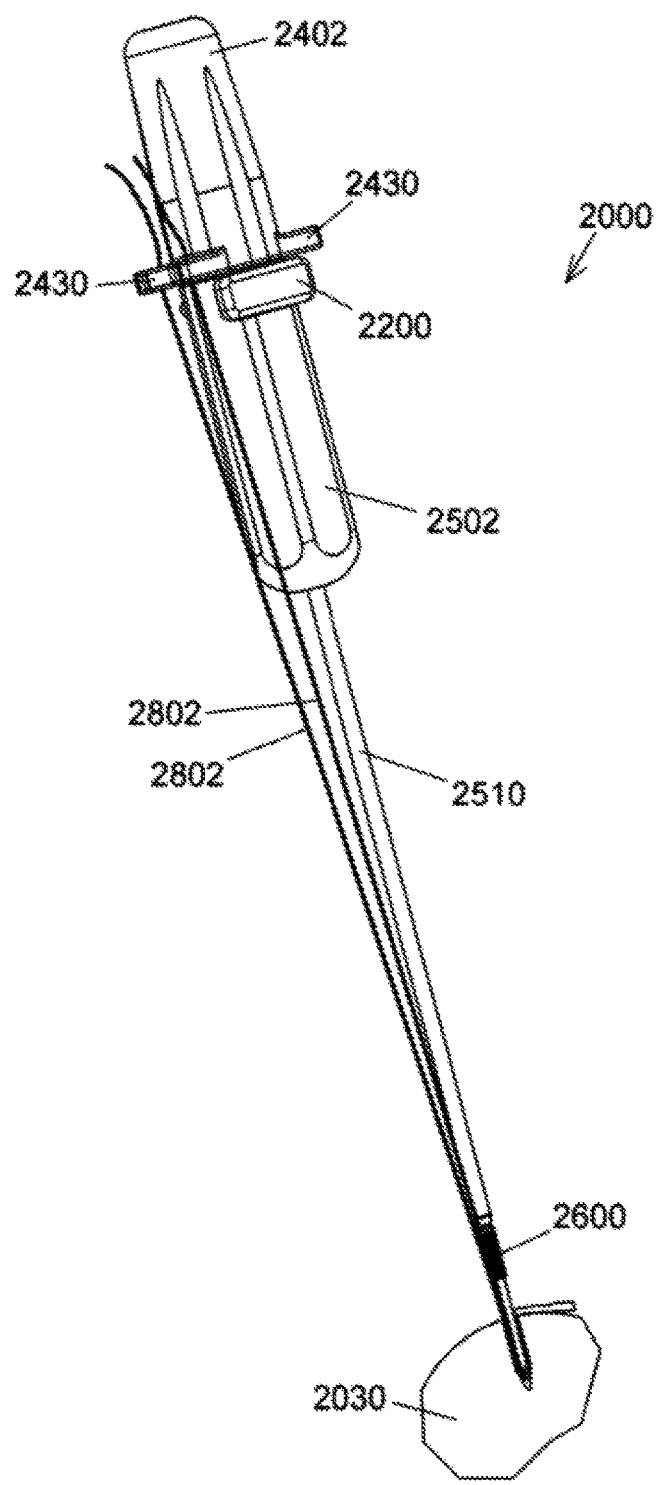
FIG. 45 depicts the alternate "fork" embodiment system with the sutures tensioned so as to position the graft.
Figure 46:
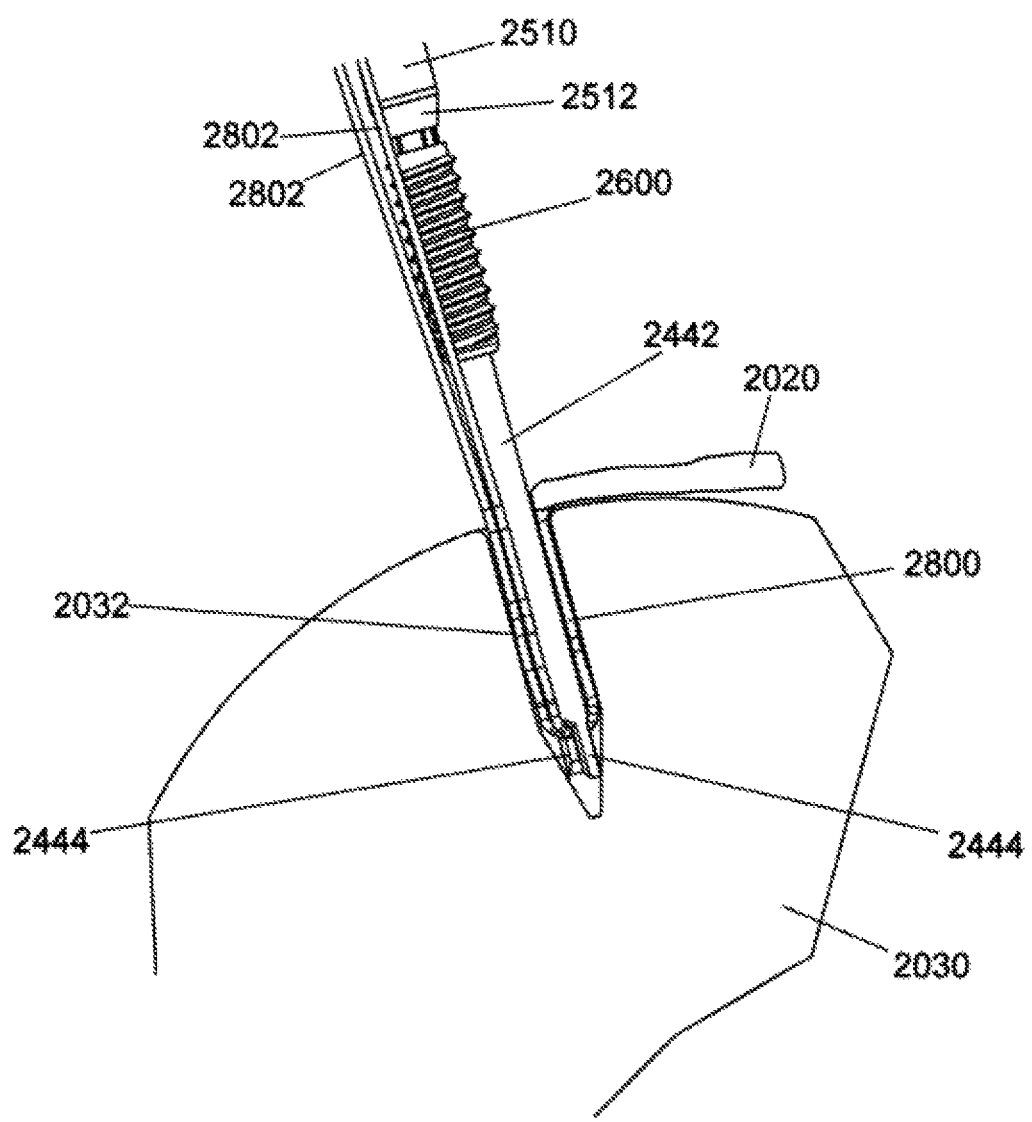
FIG. 46 is an expanded view of the distal portion of the objects of FIG. 45 depicting the placement site.
Figure 47:
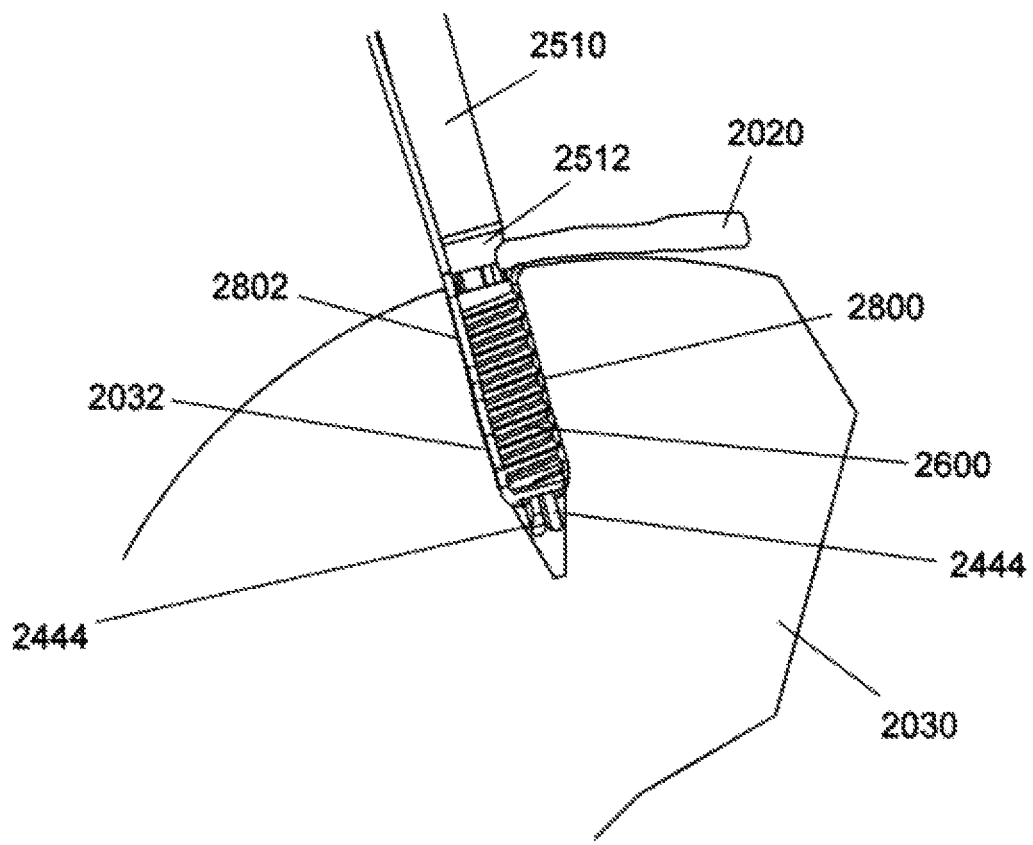
FIG. 47 is an expanded view of the site depicting the system with the anchor placed.
Figure 48:
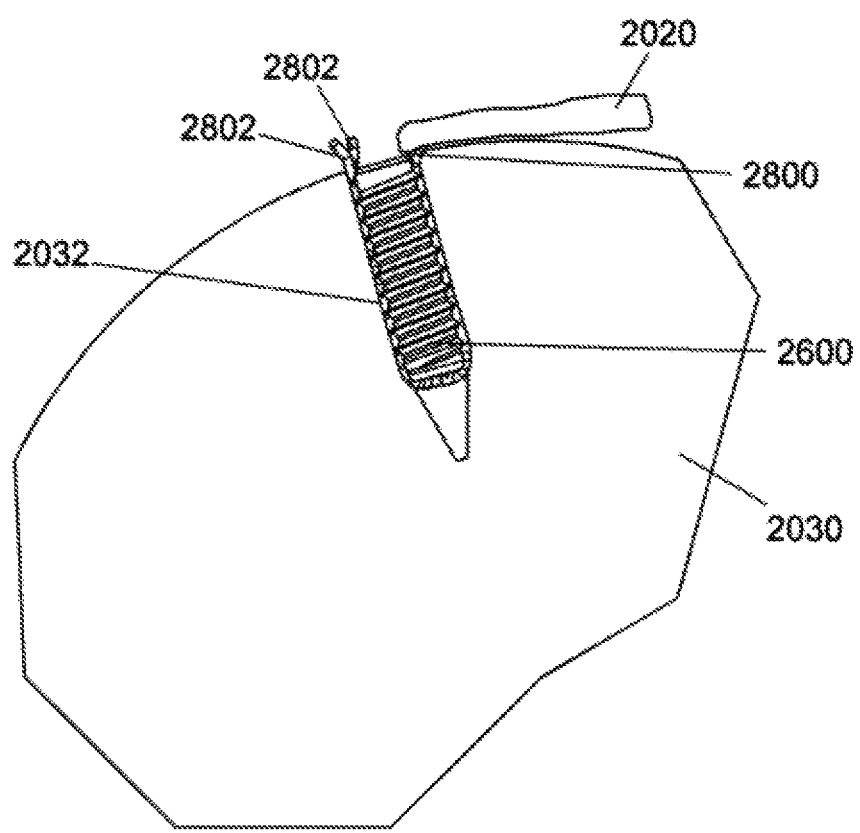
FIG. 48 is an expanded view of the site at completion of the anchor placement and removal of the system with the sutures trimmed.

A method of fixation according to the principles of the instant invention using system 2000 is depicted in FIGS. 43 through 48. A socket 2032 is formed by drilling or punching in bone 2030. Sutures 2800 are passed through graft 2020 in a usual manner. Sutures 2800 are positioned within channel 2446 at the distal end of distal element 2442 of the tensioning device and distal element 2442 is inserted into socket 2032 such that the distal end of elongate portions 2444 contact the bottom of the socket as depicted in FIGS. 43 and 44. Thereafter, referring to FIGS. 45 and 46, the surgeon grasps proximal ends 2802 of sutures 2800 and withdraws them proximally so as to advance graft 2020 towards socket 2032. When graft 2020 is in the desired position, proximal ends 2802 of sutures 2800 are secured in cleats 2432 in flanges 2430 of handle 2402 to maintain the graft position. So long as proximal portions 2802 of sutures 2800 remain cleated and the distal end of distal tensioning element 2442 is maintained in contact with the bottom surface of socket 2032, the position of graft 2020 will not change. The surgeon may adjust sutures 2800 as required to achieve optimal placement of graft 2020. When this optimal placement of graft 2020 has been achieved, while maintaining contact between the distal end off distal tubular element 2442 and the bottom of socket 2032, the surgeon removes key 2200 from system 2000 so as to allow axial and rotational movement of the driver assembly. The surgeon advances anchor 2600 to socket 2032 and screws the anchor into socket 2032 so as to trap sutures 2800 between anchor 2600 and the walls of socket 2032 in bone 2030 as depicted in FIG. 47. When anchor 2600 is fully inserted in socket 2032, proximal portions 2802 of sutures 2800 are released from cleats 2432 and system 2000 is withdrawn from the joint. Subsequently suture proximal portions 2802 of sutures 2800 are cut adjacent to anchor 2600 and the anchor placement is complete. The position of the graft is maintained by friction between the sutures 2800 that are trapped between the exterior surface of anchor 2600 and two laterally opposed portions of the walls of socket 2032.

Anchor placement systems of the present invention are also useful for the attachment of tendons in a procedure called bio tenodesis. When attaching, for instance, a biceps tendon to the humeral shaft, the proximal end of the tendon is inserted into the socket and the implant placed in a manner that traps the tendon between the anchor and the wall of the socket thereby retaining the tendon in the socket.

Figure 49:
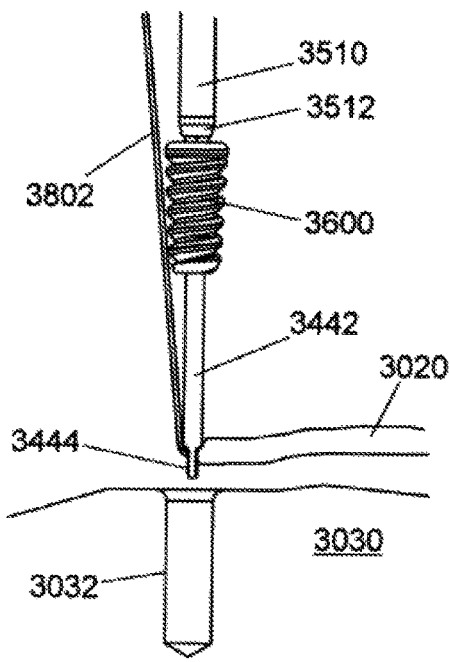
FIG. 49 depicts a first step of an alternate repair method for securing a graft in a socket using an implant as contemplated by the present invention.
Figure 50:
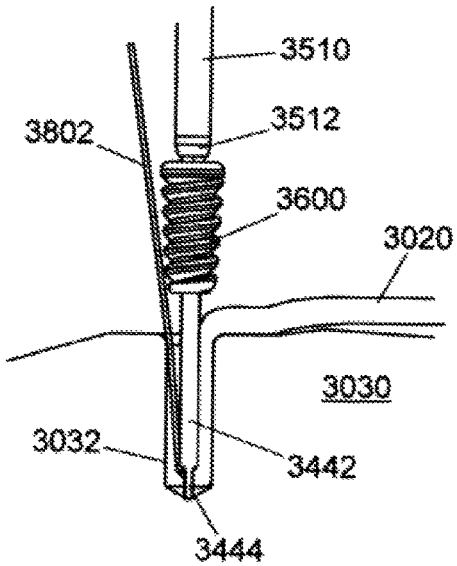
FIG. 50 depicts a second step of the alternate repair method
Figure 51:
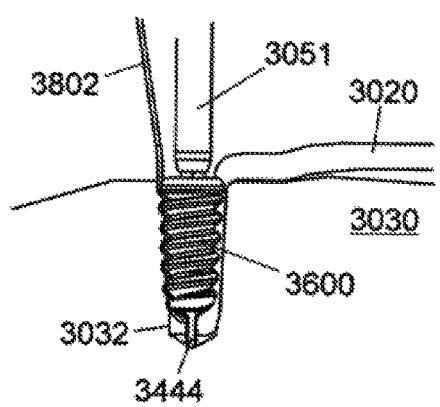
FIG. 51 depicts a third step of the alternate repair method.
Figure 52:
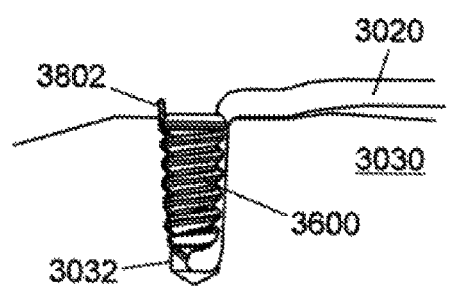
FIG. 52 depicts the site of the graft attachment at the completion of the repair using the alternate repair method.

FIGS. 49 through 52 depict an alternate embodiment method for fixation of a tendon graft using system 2000. As is commonly done in preparation for bio tenodesis, the portion of the graft that is to be inserted into the socket is first sutured in a circumferential manner, the sutures providing added resistance to pull-out when the repair is completed. Excess suture from the circumferential suturing (also called "whip stitching") is used to position the tendon prior to anchoring by the implant. Unlike previous embodiment methods disclosed herein, the positioning of graft 3020 is not achieved by tensioning the sutures after distal element 3442 is inserted into socket 3032. Rather, as depicted in FIG. 49 sutures 3802 are positioned within channel 3446 at the distal end of distal element 3442 of the tensioning device and tensioned such that graft 3020 is positioned and retained adjacent to the distal end of distal element 3442 adjacent to distally extending portions 3444. Tension in sutures 3802 is then maintained by cleating in the manner previously herein described. Thereafter, distal element 3444 is inserted into socket 3032 as shown in FIG. 50 and anchor 3600 is placed as depicted in FIG. 51 trapping graft 3020 between anchor 3600 and the boney surface of the wall of socket 3032 at a first location, and trapping sutures 3082 between anchor 3600 and the boney surface of the wall of socket 3032 at a second location. Friction forces acting at these locations maintain the position of graft 3020 relative to socket 3032 and bone 3030. FIG. 52 depicts the site at completion of the anchor placement and removal of insertion system 3000.

Figure 53:
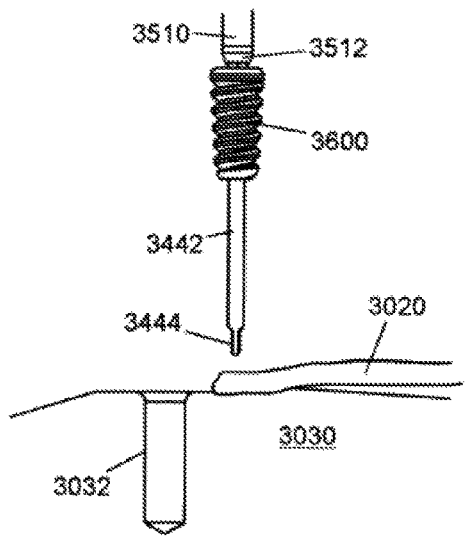
FIG. 53 depicts a first step of a second alternate repair method for securing a graft in a socket using an implant.
Figure 54:
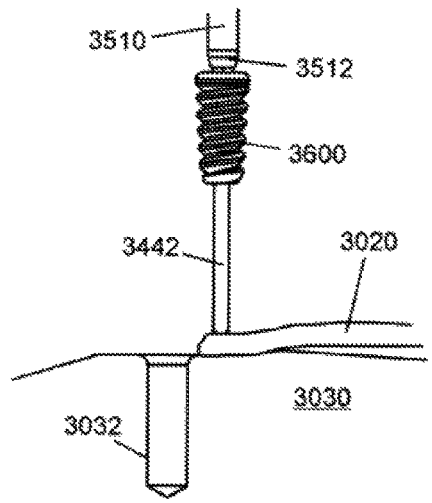
FIG. 54 depicts a second step of the alternate repair method
Figure 55:
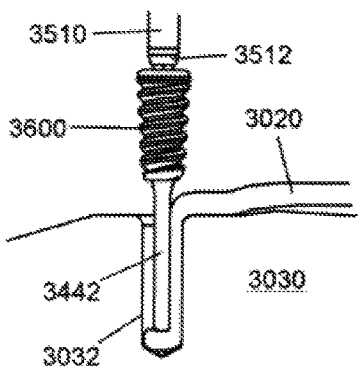
FIG. 55 depicts a third step of the alternate repair method.
Figure 56:
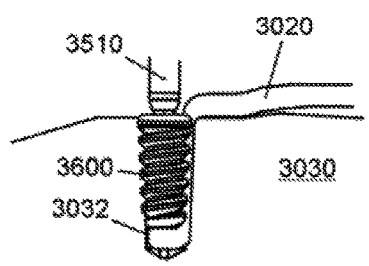
FIG. 56 depicts a fourth step of the alternate repair method.
Figure 57:
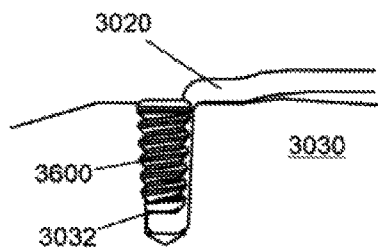
FIG. 57 depicts the site of the graft attachment at the completion of the repair using the alternate embodiment repair method.

FIGS. 53 through 57 depict an alternate embodiment method of anchoring a graft to bone using the alternate anchor placement system 2000 of the present invention. Rather than using tensioned sutures to maintain the placement of a graft at the distal end of distal element 3442 as previously depicted in FIG. 49, the graft is impaled on the distally extending portions 3444 of distal element 3442 as shown in FIGS. 53 and 54, the sharpened distal ends 3448 of extending portions 3444 penetrating the graft. Thereafter, distal element 3444 is inserted into socket 3032 as shown in FIG. 55 and anchor 3600 is placed as depicted in FIG. 56 trapping graft 3020 between anchor 3600 and the boney surface of the wall of socket 3032. Friction force between the inserted portion of graft 3020 and socket 3032 maintains the position of graft 3020 relative to socket 3032 and bone 3030. FIG. 57 depicts the site at completion of the anchor placement and removal of insertion system 3000. If the graft has been whip-stitched and the excess suture remains, the suture tails will also be trapped between anchor 3600 and socket 3032 thereby providing additional resistance to pull out.

Figure 58:
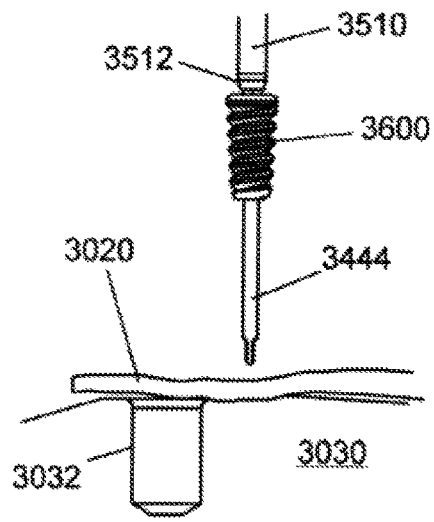
FIG. 58 depicts a first step of a third alternate repair method for securing a graft in a socket using an implant.
Figure 59:
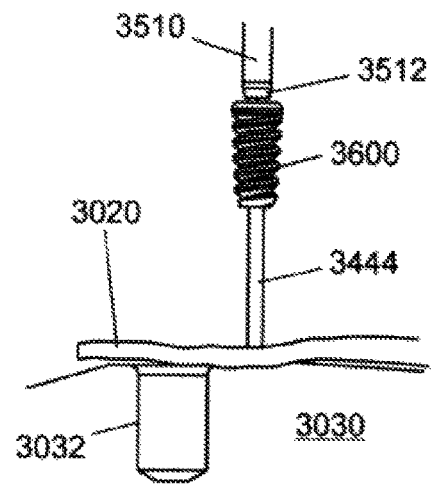
FIG. 59 depicts a second step of the alternate repair method
Figure 60:
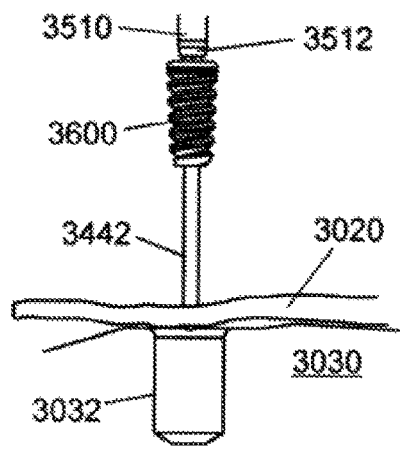
FIG. 60 depicts a third step of the alternate repair method.
Figure 61:
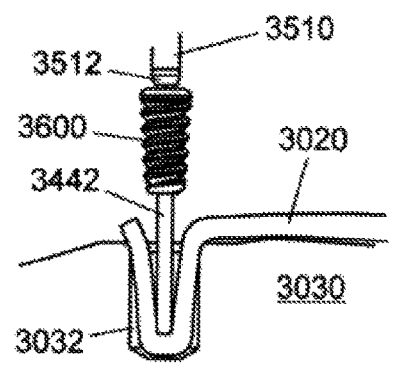
FIG. 61 depicts a fourth step of the alternate repair method.
Figure 62:
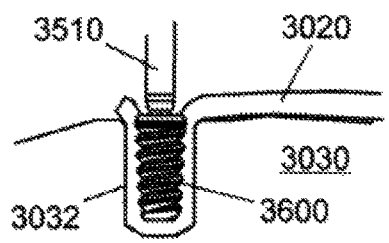
FIG. 62 depicts a fifth step of the alternate repair method.
Figure 63:
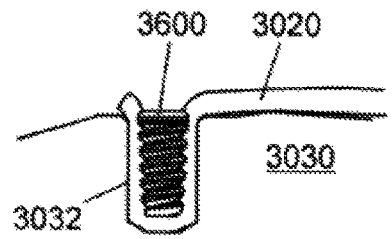
FIG. 63 depicts the site of the graft attachment at the completion of the repair using the alternate embodiment repair method.
Figure 68:
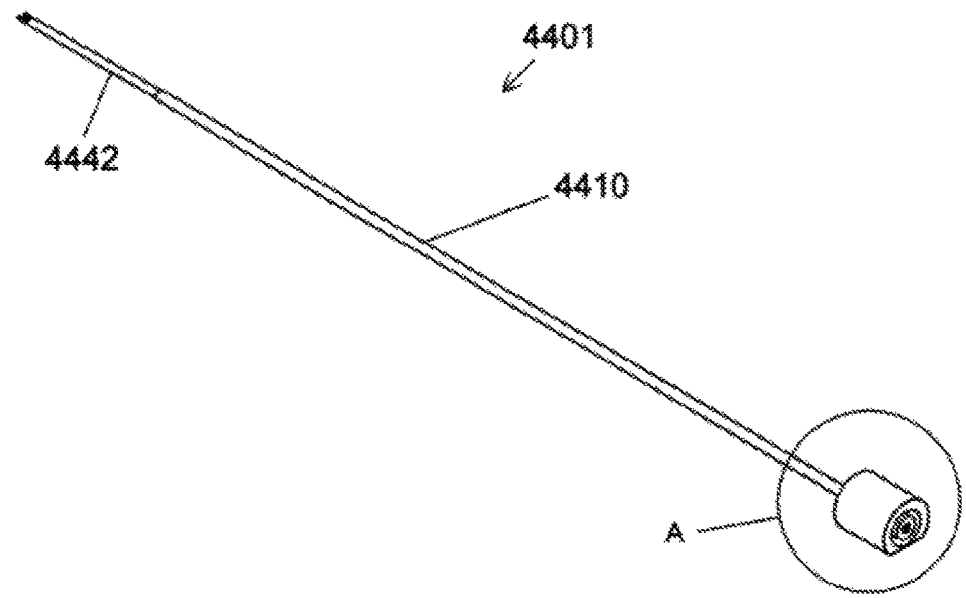
FIG. 68 is a perspective view of the objects of FIG. 64.
Figure 69:
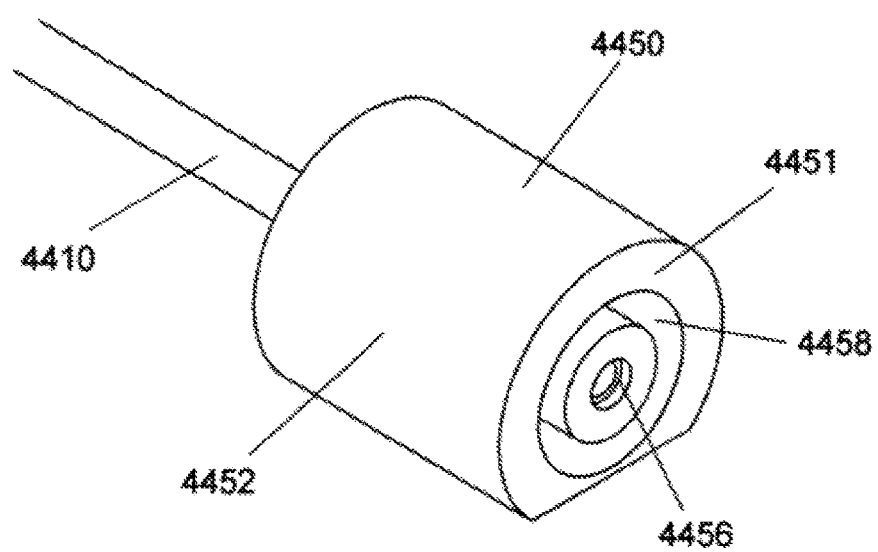
FIG. 69 is a expanded view of the proximal portion of the objects of FIG. 68 at location A.
Figure 70:
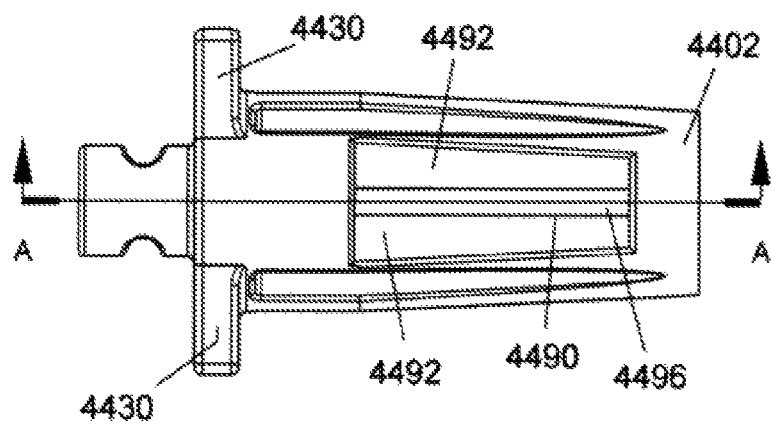
FIG. 70 is a plan view of the handle portion of a tensioning device for an alternate embodiment anchor placement system.
Figure 71:
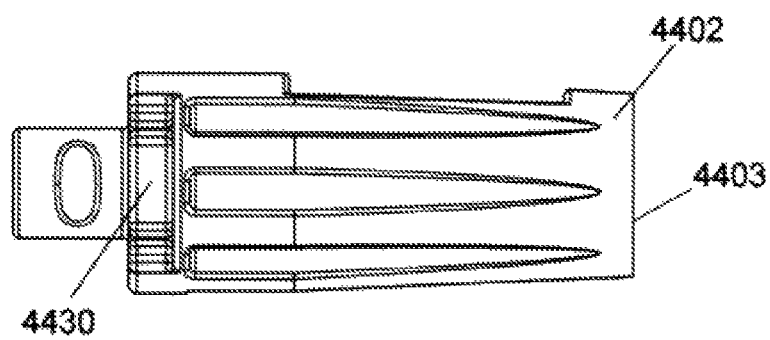
FIG. 71 is a side elevational view of the objects of FIG. 70.
Figure 72:
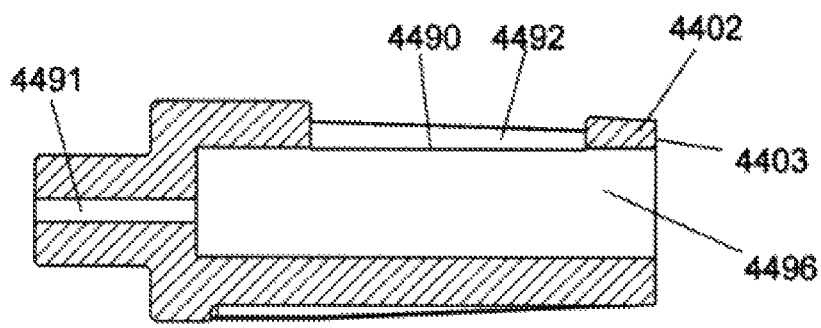
FIG. 72 is a sectional view of the objects of FIG. 70 at location A-A.
Figure 73:
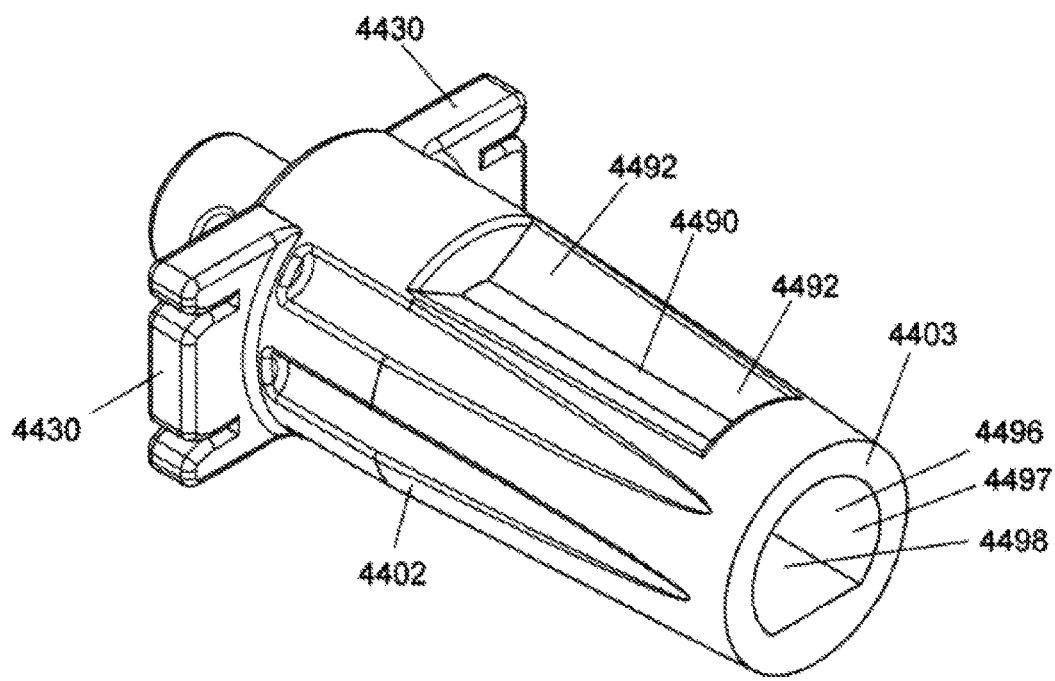
FIG. 73 is a perspective view of the objects of FIG. 70.
Figure 74:
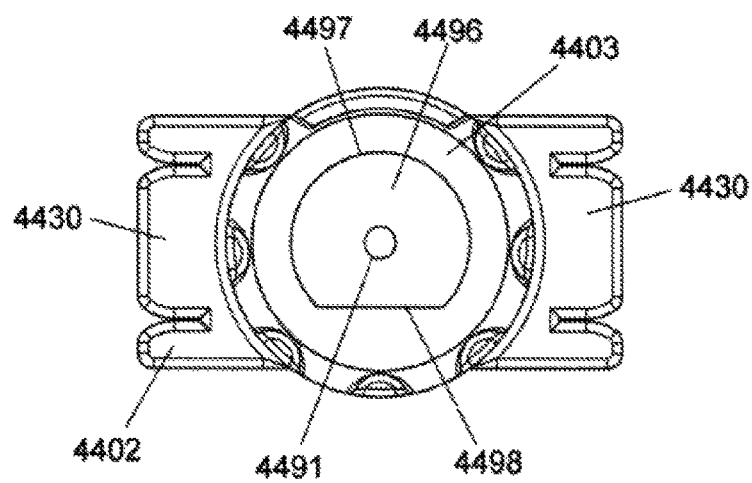
FIG. 74 is an expanded proximal axial view of the objects of FIG. 70.
Figure 75:
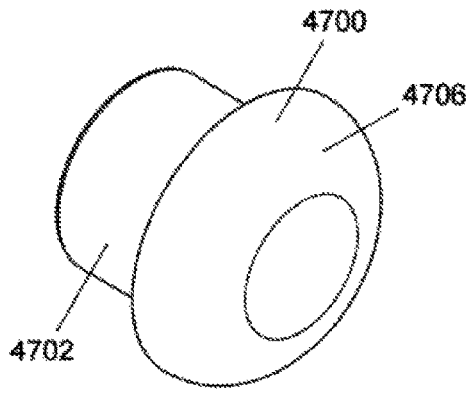
FIG. 75 is a perspective view of an end cap for the tensioning device for an alternate embodiment anchor placement system.
Figure 76:
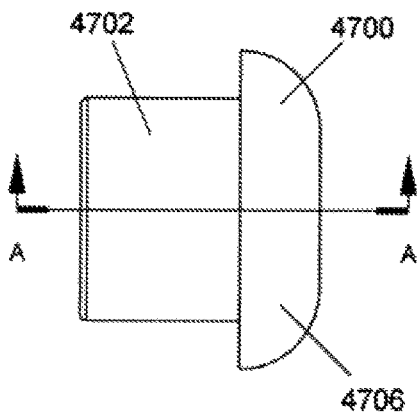
FIG. 76 is a plan view of the objects of FIG. 75.
Figure 77:
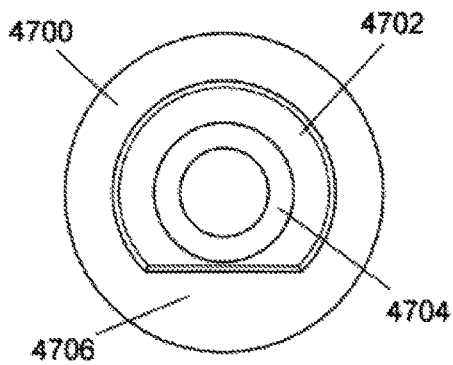
FIG. 77 is a distal axial view of the objects of FIG. 75.
Figure 78:
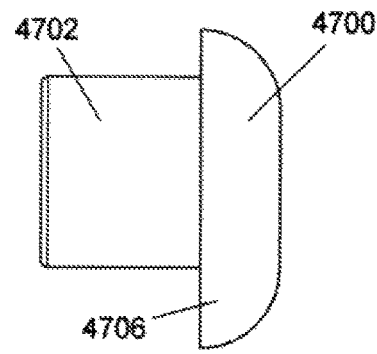
FIG. 78 is a side elevational view of the objects of FIG. 75.
Figure 79:
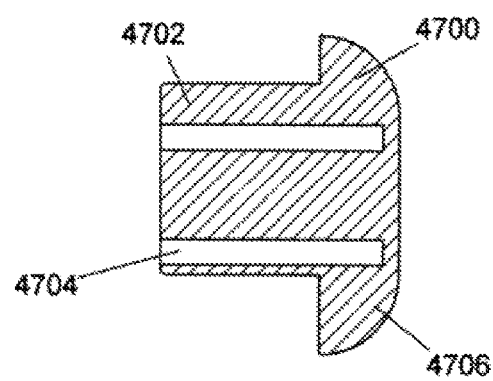
FIG. 79 is a sectional view of the objects of FIG. 76 at location A-A.
Figure 82:
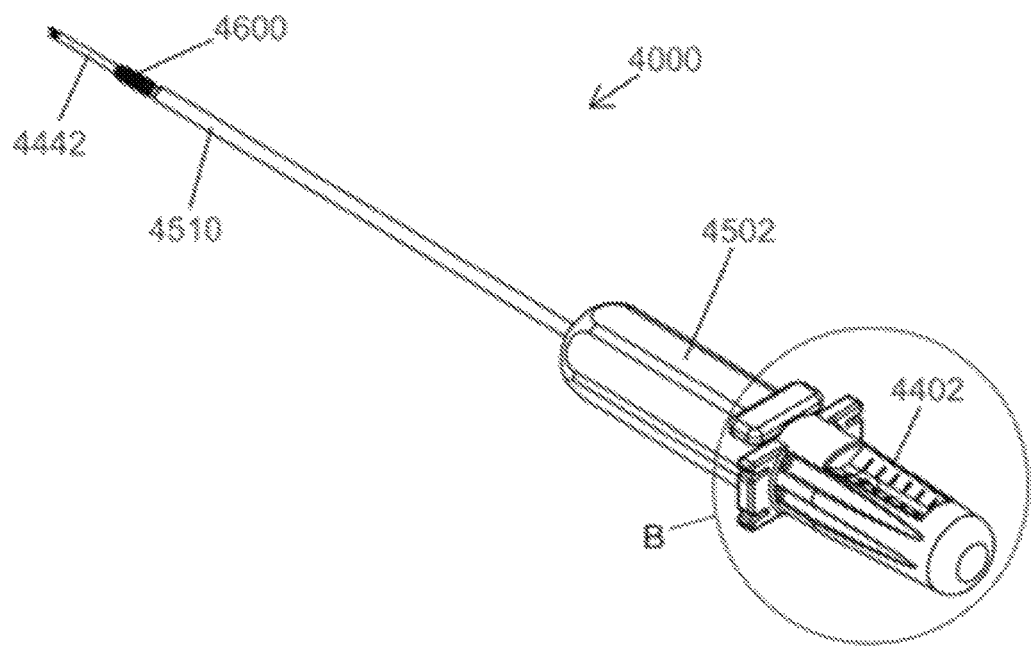
FIG. 82 is a perspective view of the objects of FIG. 80.
Figure 83:
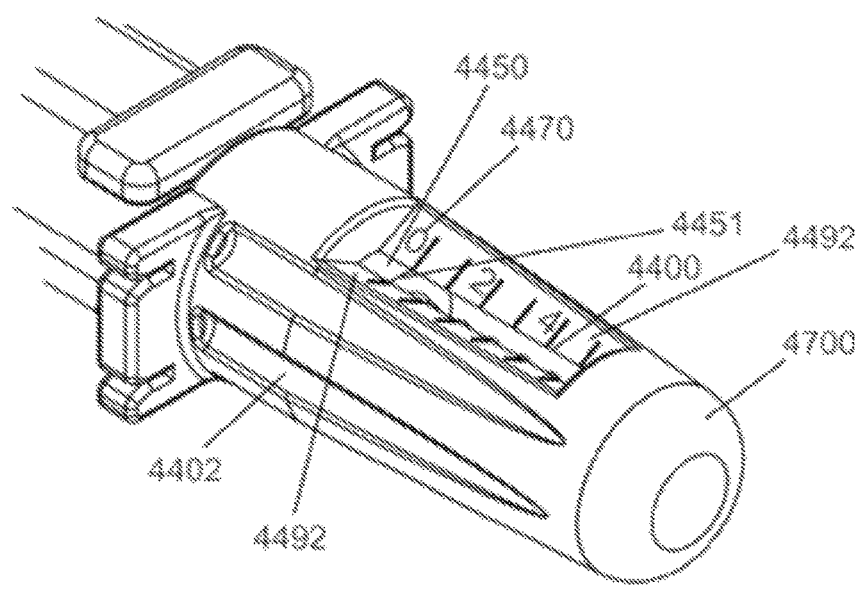
FIG. 83 is an expanded view of the proximal portion of the objects of FIG. 82 at location A.
Figure 84:
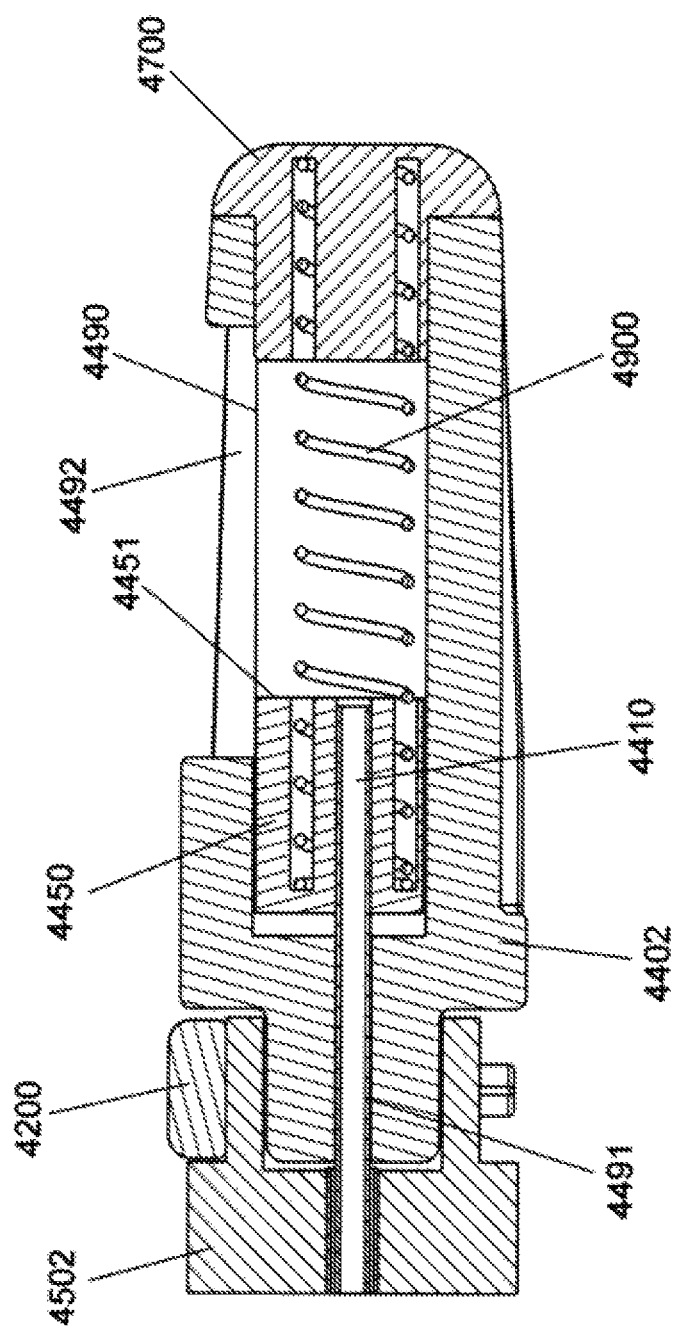
FIG. 84 is a central expanded side elevational sectional view of the objects of FIG. 81.

FIGS. 58 through 63 depict yet another alternate method for securing a ligament graft to bone using anchor system 2000. As in the previous embodiments, sutures are not used to position and tension the graft 3020 in socket 3032. Rather, as in the previous method, graft 3020 is impaled on the distally extending portions 3444 of distal element 3442 as shown in FIGS. 58 and 59, the sharpened distal ends to of extending portions 3444 penetrating the graft. The site for penetration is selected such that when the ligament is inserted to the bottom of socket 3032 the proximal end of graft 3020 protrudes above the rim of socket 3032. As seen in FIG. 60, graft 3020 is positioned above socket 3032, inserted as shown in FIG. 61, and anchor 3600 placed as shown in FIG. 62. FIG. 63 shows the completed repair. Graft 3020 is trapped between the exterior surface of anchor 3600 and first and second laterally opposed portions of the wall of socket 3032 and retained in position by friction therefrom.

It may be useful to determine the tension in a tendon undergoing a tenodesis procedure so that optimal tension may be selected based on the particular anatomy. In another embodiment of the instant invention, the inner tensioning member is provided with a mechanism that indicates the force being applied to the graft during insertion into the socket. The insertion site on the graft may be adjusted such that when the graft is inserted to the bottom of the socket the predetermined optimal tension is achieved, and thereafter maintained during anchor placement.

FIGS. 64 through 69 depict a distal assembly 4401 for a force indicating mechanism for use with an inner tensioning assembly in accordance with the present invention. Elongate tubular element 4410 has at its distal end distal element 4442, identical to distal element 3442 (FIGS. 36 through 40), and at its proximal end element 4450 affixed thereto. Element 4450 has a cylindrical outer surface portion 4452 and a planar outer surface portion 4454. The proximal end of tubular element 4410 is then positioned within lumen 4456. Recess 4458 extends distally from proximal-most surface 4451.

FIGS. 70 to 74 depict a handle 4402 for a force indicating inner tensioning assembly. Handle 4402 is identical to handle 2402 in all aspects except as subsequently described. Specifically, handle 4402 has a distal lumen 4491 with a diameter which allows tubular element 4410 to be slidably positioned therein. Recess 4496 extends distally from proximal-most surface 4403 of handle 4402 and has a cylindrical surface portion 4497 and a planar portion 4498 sized such that element 4450 may be positioned therein. This construction is such that when distal assembly 4401 is assembled to handle 4402 with element 4450 positioned within recess 4496 and tubular member 4410 is positioned within lumen 4491 of handle 4402, distal assembly 4401 may be move axially relative to handle 4402 but rotation is prevented. Handle 4402 has a window 4490 formed in its top surface with adjacent beveled surfaces 4492 so that recess 4496 and elements therein may be viewed.

FIGS. 75 through 79 depict a proximal end cap 4700 for handle 4402. End cap 4700 has a distal portion 4702 with proximally extending recess 4704, and a proximal portion 4706. Distal portion 4702 is configured for assembly to handle 4402.

Referring now to FIGS. 80 through 84 which depict a force indicating anchor system 4000 of the instant invention, distal assembly 4401 may be assembled to handle 4402 as previously described, and end cap 4700 is assembled to the proximal end of handle 4402. Spring 4900 is positioned therebetween with its distal end in recess 4458 of element 4450 and its proximal end in recess 4704 of end cap 4700. As seen in FIG. 81, indicia 4470 are formed on beveled surfaces 4492 such that the position of proximal-most surface 4451 of element 4450 visible through window 4490 may be quantified. The position of element 4450 and its proximal-most surface 4451 is determined by the amount of deflection of spring 4900, which is in turn determined by the force exerted on distal assembly 4401. This force is exerted on distal assembly 4401 by tension in the graft during insertion into a socket by distal element 4442. Device 4000 may be calibrated so that during insertion of the graft into the socket by the surgeon, by observing the position of proximal-most surface 4451 relative to the indicia, will know the insertion force and thereby the tension in the graft.

Figures 92, 93:
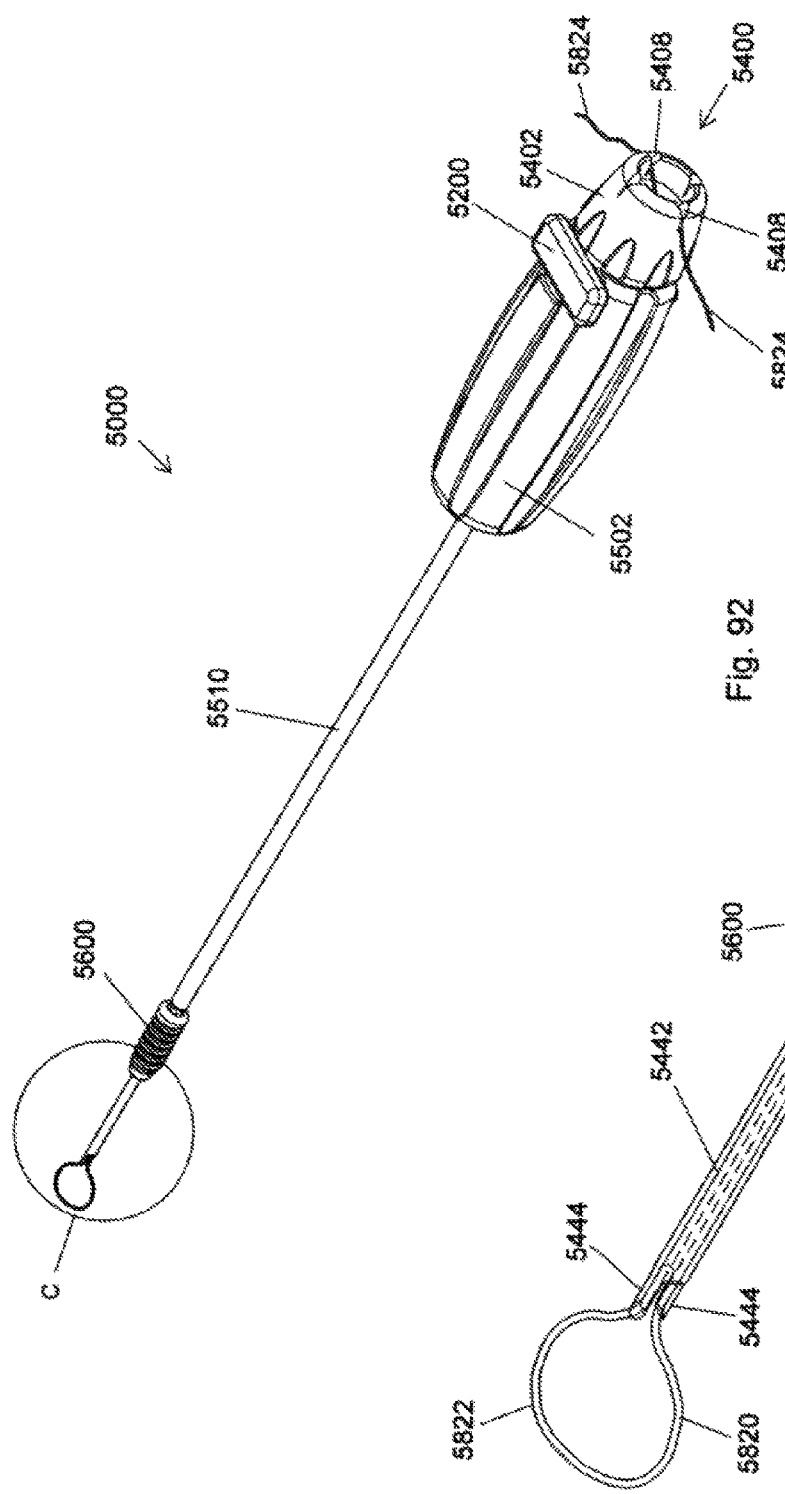
FIG. 92 is a proximal perspective view of an alternate embodiment anchor placement system of the present invention.
FIG. 93 is an expanded view of the objects of FIG. 93 at location C.
Figure 94A:
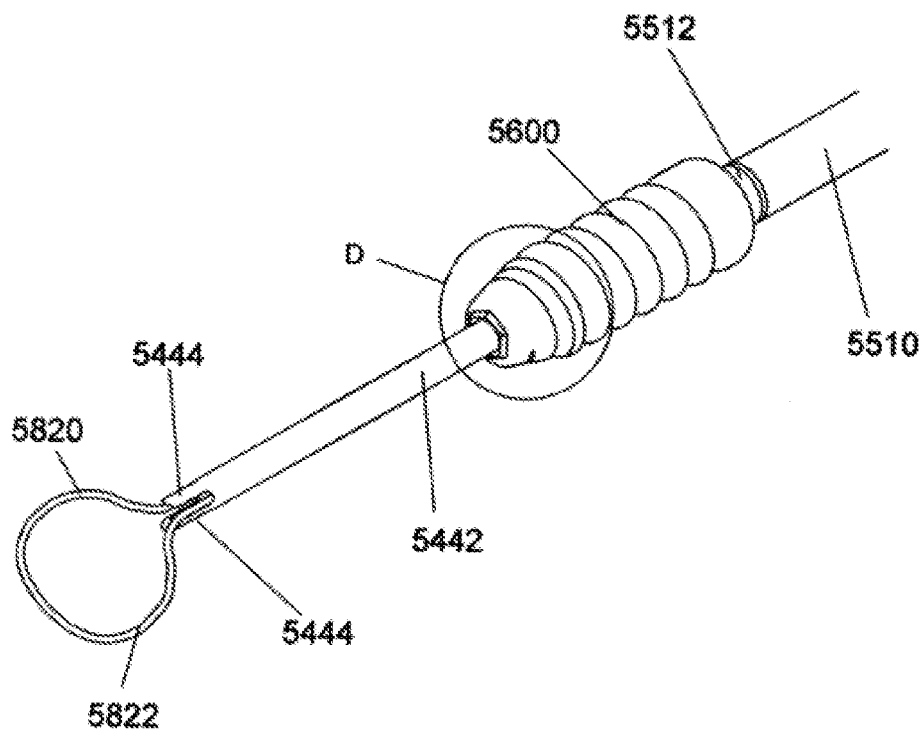
FIG. 94A is an expanded distal perspective view of the distal portion of the objects of FIG. 92.
Figure 94B:
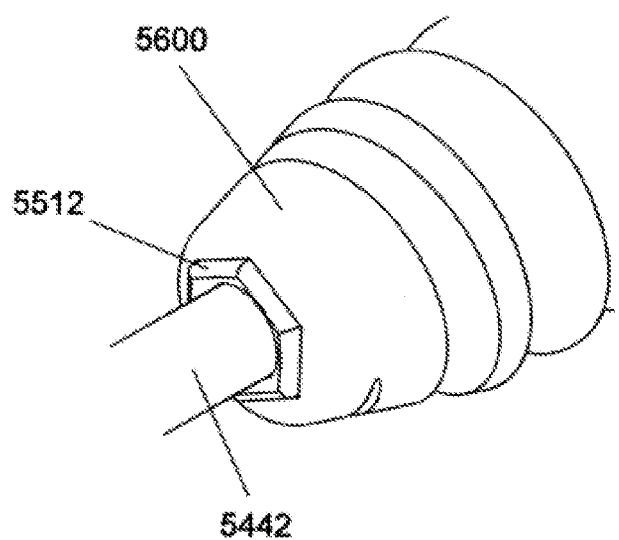
FIG. 94B is an expanded view of the objects of FIG. 94A at location D.

When performing a bio-tenodesis procedure as depicted in FIGS. 53 through 57 and in FIGS. 58 through 63, it may be possible for the graft 3020 to become dislodged from distally extending portions 3444 of tensioning distal element 3442. This problem is addressed in an alternate embodiment implant placement system 5000 of the present invention depicted in FIGS. 92 through 94. Therein, a suture loop releasably maintains the position of the graft during manipulation and placement. Placement system 5000 is alike in all aspects to system 2000 except as specifically described hereafter. Specifically, distal element 5442 of tensioning device 5400 is cannulated and handle 2402 of tensioning device 2400 is replaced by handle 5402 which is identical to handle 1402 of tensioning device 1400 (FIGS. 3 through 9). Suture 5820 has a distal portion forming a loop 5822 distal to the distal end of distal element 5442 of tensioning device 5400. Suture 5820 extends proximally through the cannulation of distal element 5442 of tensioning device 5400, and proximally therefrom such that proximal portions 5824 of suture 5820 extend beyond handle 5402. This allows the surgeon to apply tension to the suture loop 5822 so as to secure a graft placed therein, and to maintain that tension by securing proximal portions 5824 in slots 5408 of handle 5402.

Figure 95:
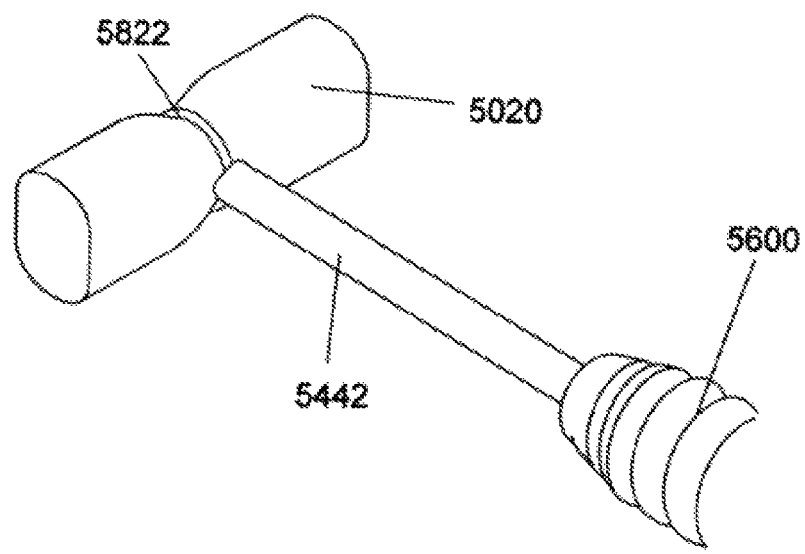
FIG. 95 is an expanded proximal perspective view depicting the alternate embodiment anchor placement system of FIG. 92 in use with a tendon secured to the distal end of the tensioning device in preparation for placement in a socket.
Figure 96:
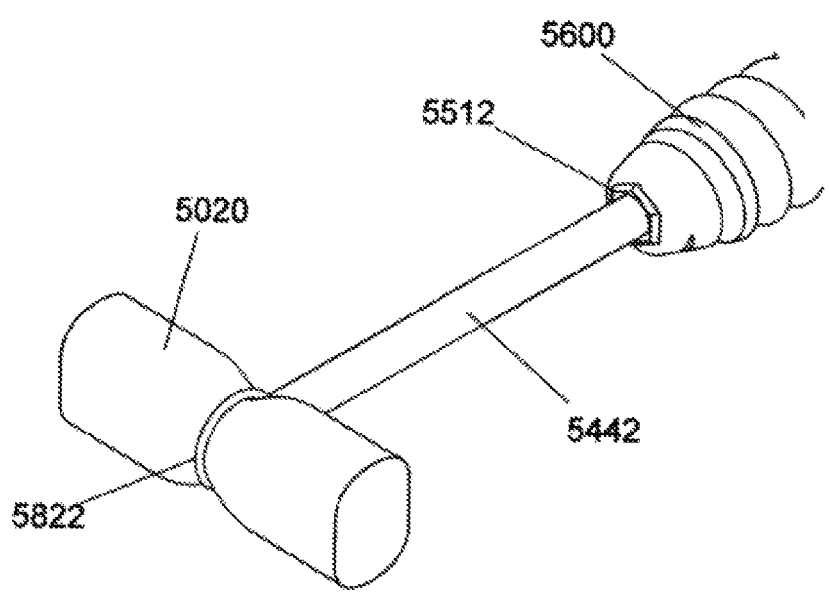
FIG. 96 is a distal perspective view of the objects of FIG. 95.

FIGS. 95 and 96 depict the distal portion of system 5000 as in use wherein a graft 5020 impaled on distal portions 5444 of tensioning device 5400 as previously herein described and referenced in FIGS. 53 through 63. As depicted in FIGS. 95 and 96, tension applied to proximal portions 5824 of suture 5820 has drawn suture loop 5822 tightly around graft 5020 and secured graft 5020 to the distal end of distal element 5442 in a manner that prevents disengagement of graft 5020 from distally extending portions 5444 of distal element 5442. The placement of implant 5600 is accomplished in the same manner as implant 3600 in FIGS. 53 through 63 and previously herein described except for the added steps of securing graft 5020 to the distal end of distal element 5444 using suture 5820 as previously described; the step of after placement of implant 5600 as depicted in FIGS. 56 and 62, releasing proximal ends 5824 of suture 5820 from slots 5408 of handle 5402; and, at the completion of the anchor placement as depicted in FIGS. 57 and 63, the step of trimming the suture 5820 adjacent to implant 5600 or withdrawing suture 5820 from the site.

Unlike prior art device 100, wherein suture loop 108 is adjacent to the distal end of driver 104 which rotates during suture placement (see FIG. 85), loop 5820 passes from the distal end of the non-rotating tensioning device 5400 and removably affixes graft 5020 thereto. Accordingly, no torque is transmitted to graft 5020 and twisting of graft 5020 is wholly prevented. Moreover, graft 5020 cannot easily slip from suture loop 5820 since it is additionally impaled on distally extending portions 5444 of distal element 5442 of tensioning device 5400.

Figure 97:
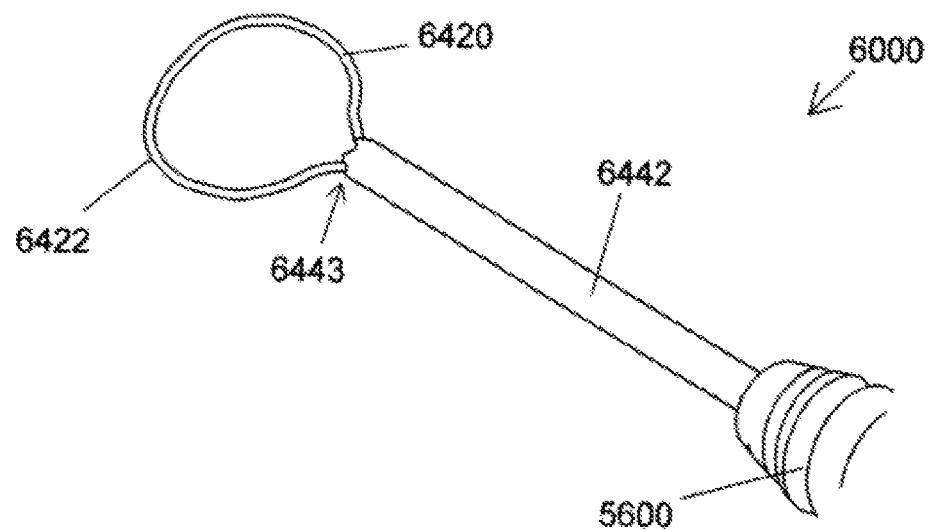
FIG. 97 is an expanded proximal perspective view of the distal portion of an alternate embodiment anchor system of the present invention.
Figure 98:
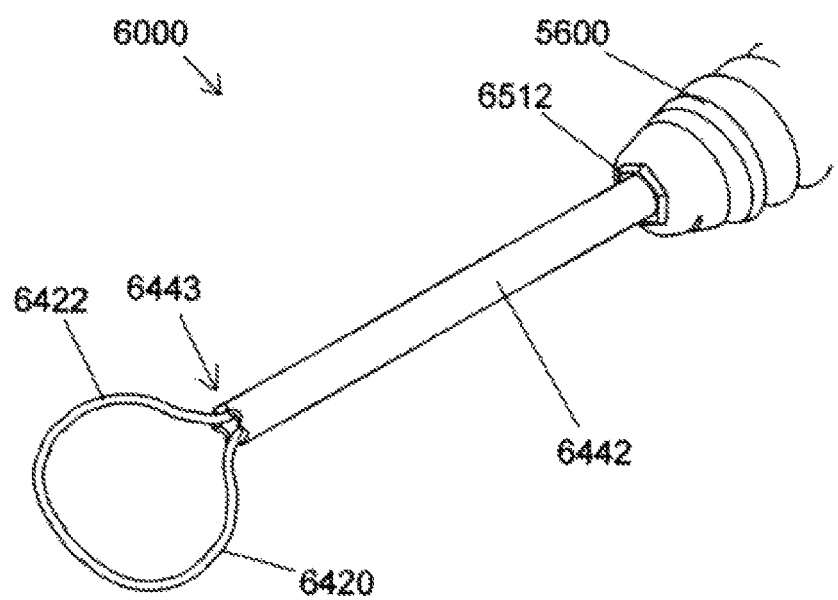
FIG. 98 is a distal perspective view of the objects of FIG. 97.
Figure 99:
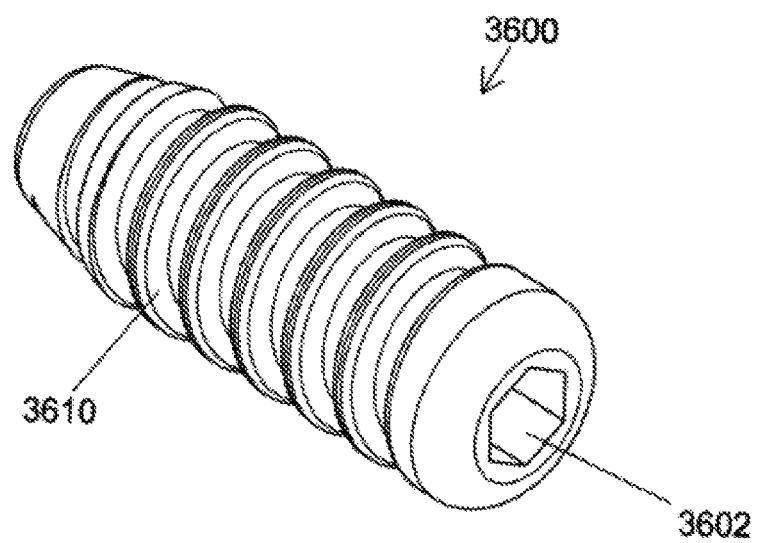
FIG. 99 is a proximal perspective view of an anchor for an implant placement system of the present invention.
Figure 100:
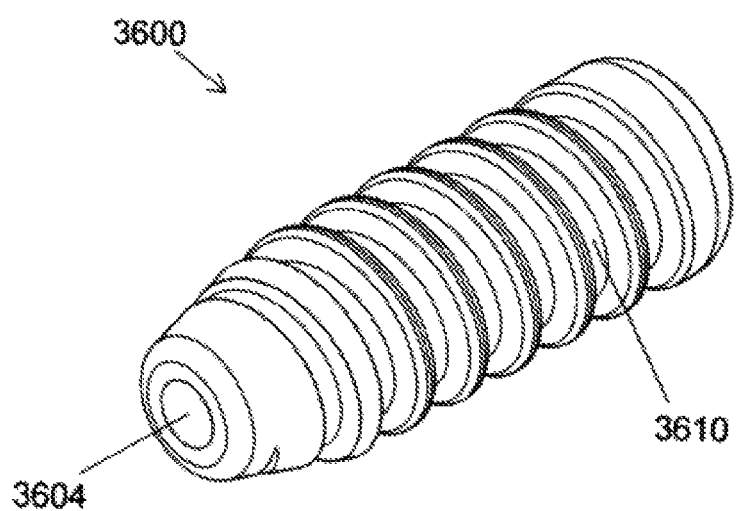
FIG. 100 is a distal perspective view of the objects of FIG. 99.
Figure 101:
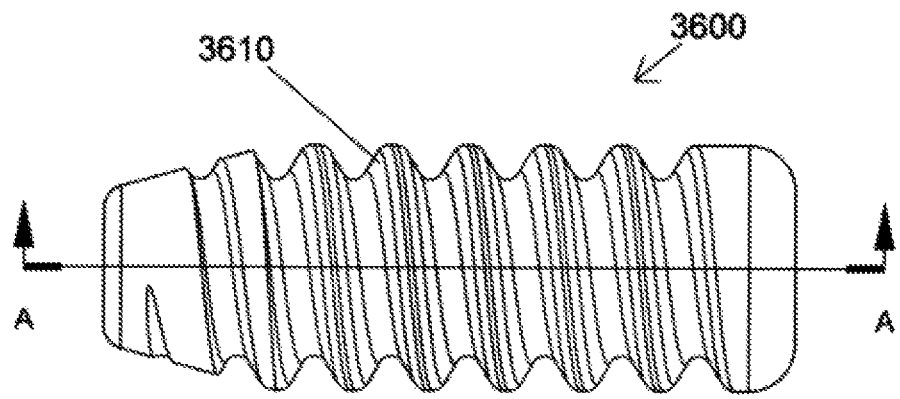
FIG. 101 is a plan view of the objects of FIG. 99.
Figure 102:
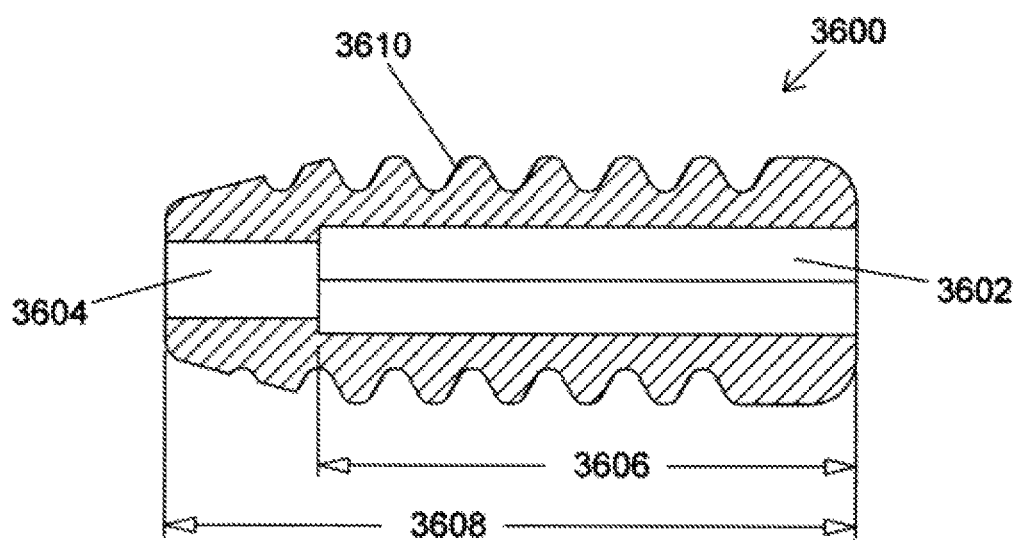
FIG. 102 is a sectional view of the objects of FIG. 101 at location A-A.
Figure 103:
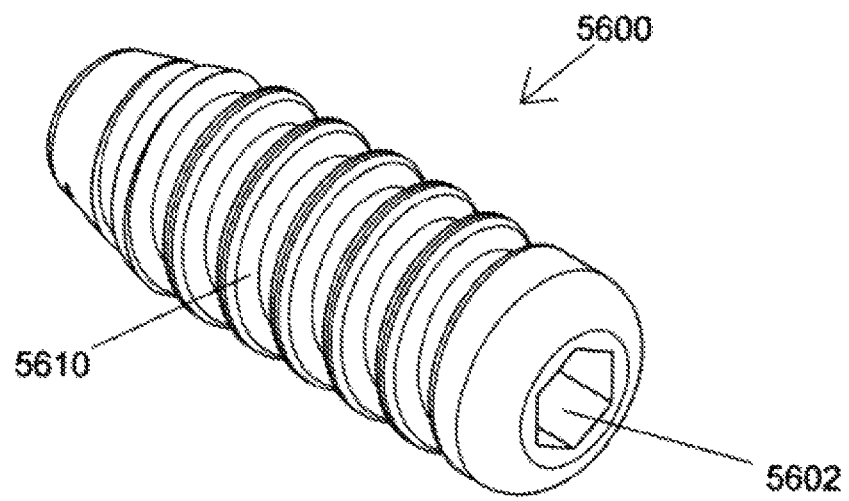
FIG. 103 is a proximal perspective view of an alternate embodiment anchor for an implant placement system of the present invention.
Figure 104:
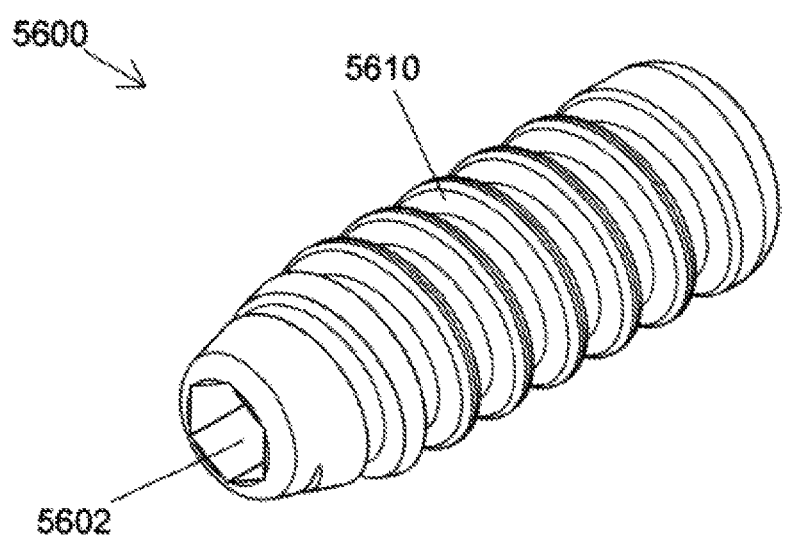
FIG. 104 is a distal perspective view of the objects of FIG. 103.
Figure 105:
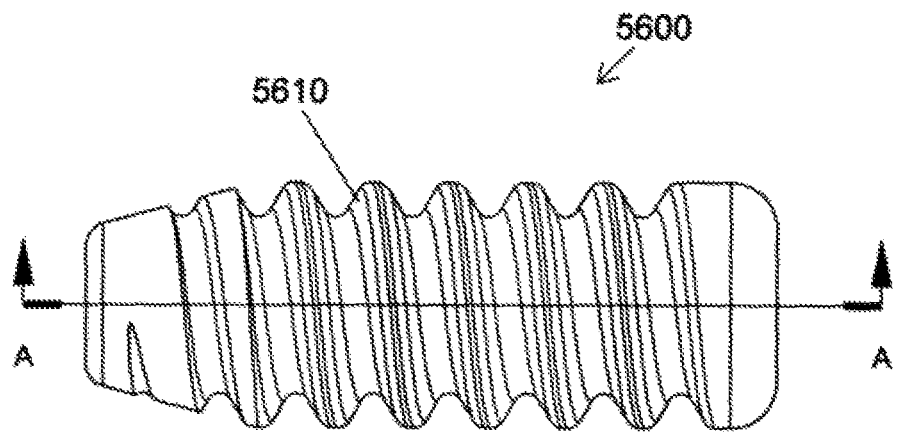
FIG. 105 is a plan view of the objects of FIG. 103.
Figure 106:
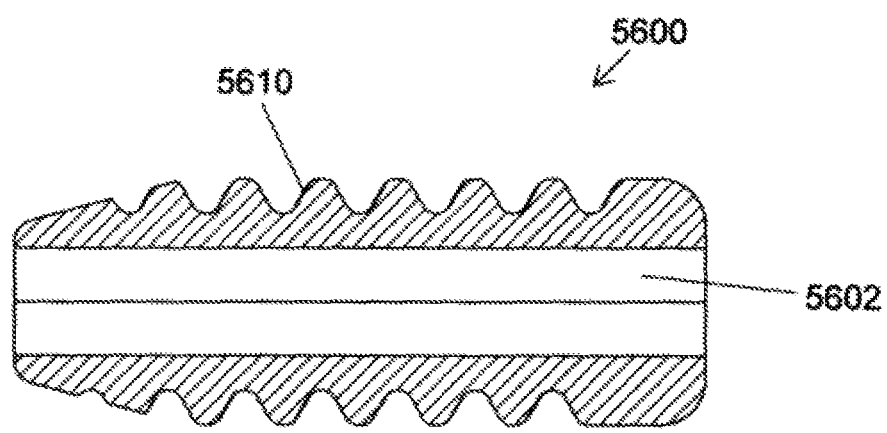
FIG. 106 is a sectional view of the objects of FIG. 105 at location A-A.

In other embodiments, distally extending portions 5444 of distal element 5442 are eliminated. For instance, FIGS. 97 and 98 depict the distal portion of an anchor placement system 6000 in which the distal end 6443 of distal element 6442 of a tensioning device 6400 has formed thereon serrations that penetrate the graft when suture loop 6822 is tightened so as to prevent the graft from slipping out of loop 6422 during insertion of the graft into a socket. Distal end 6443 of distal element 6442 of tensioning device 6400 may have other features formed thereon to aid in maintaining the graft position within suture loop 6822. Illustrative examples of such features include, but are not limited to, notches, slots, protuberances and/or recesses or projecting portions. Accordingly, the present invention is not limited to any one particular configuration.

Indeed, implant placement system 1000 (FIGS. 1 through 19) may be used in the same manner as placement systems 5000 and 6000 if a suture loop is formed distal to the distal end of tubular distal element 1412 of tensioning device 1400. Because distal element 1412 does not rotate during anchor placement, no torque is transmitted to the graft. This allows the graft to be affixed to the distal end of distal element 1412 with sufficient resistance to removal of the graft from the suture loop so that the graft may be reliably inserted into a prepared socket for anchor placement.

FIGS. 99 through 102 depict anchor 3600 of anchor system 3000 depicted in FIGS. 46 through 63. Anchor 3600 of length 3608 has a threaded outer surface 3610, and a central lumen with a drive portion 3602 extending distance 3606 from the proximal end surface of anchor 3600. Distal to lumen drive portion 3602, cylindrical lumen portion 3604 extends to the distal end of anchor 3600.

FIGS. 103 through 106 depict anchor 5600 of anchor system 5000 of FIGS. 94A through 96, and of anchor system 6000 of FIGS. 97 and 98. Anchor 5600 is identical to anchor 3600 in all respects except as specifically described below. Specifically, lumen drive portion 5602 extends from the proximal end of anchor 5600 to the distal end of anchor 5600. During use, as best seen in FIGS. 94A, 94B, 96 and 98, the distal drive portion of distal drive element 5512 extends the length of anchor 5600, the distal-most surface of distal drive element 5512 being flush with, or a short distance beyond the distal-most surface of anchor 5600.

The length 3606 of the drive portion 3602 of an anchor of the present invention is a matter of design choice and may be based on the mechanical properties of the material from which anchor 3600 is made. For anchors 3600 formed of a low-strength material such as, for instance, a bio-absorbable material, it may be desirable to have the torque transmission portion 3602 of the central lumen extend for a large portion of the length of the anchor, or, as in anchor 5600, extend the entire length of the anchor. Any cannulated threaded anchor may be used with anchor systems of the present invention.

Certain embodiments of the present invention previously described herein include an optional key to prevent angular and axial movement of the driver relative to the tensioning device prior to anchor placement. Removal of the key allows the driver to advance the anchor to the socket and to place the anchor in the socket as previously herein described. In other embodiments of the present invention, this key may be eliminated and other alternative mechanisms may be used to prevent unintended axial and rotational motion of the driver relative to the tensioning device.

Figure 107:
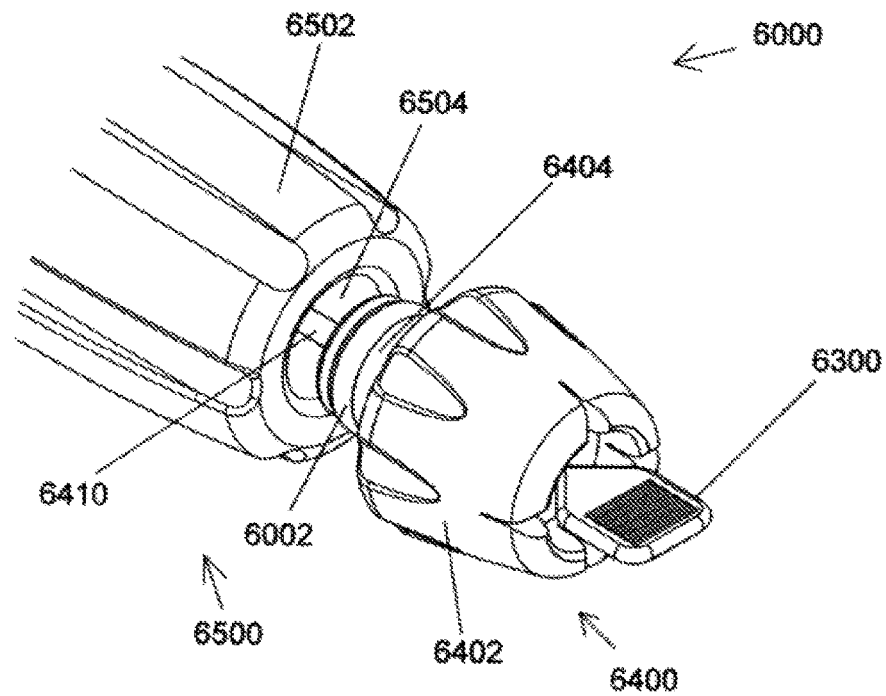
FIG. 107 is a perspective view of the proximal handle portion of an alternate embodiment of the present invention with the tensioning device withdrawn proximally a distance from the driver.
Figure 108:
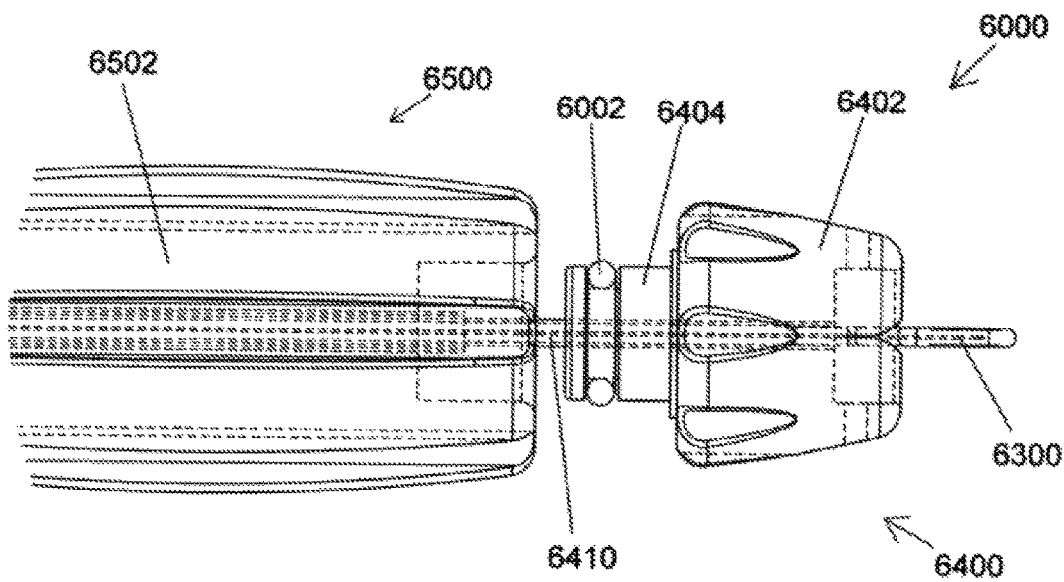
FIG. 108 is a plan view of the objects of FIG. 106.

FIGS. 107 and 108 depict the proximal handle portion of system 6000. Device 6000 is identical to device 1000 (FIGS. 1 through 19) in all aspects of construction and use except as subsequently described herein. Specifically, in FIGS. 107 and 108, tensioning device 6400 is withdrawn proximally to reveal features of hub 6402 and handle 6502. Key 1200 of device 1000 is eliminated along with cooperative mating features of tensioning device 1400 and driver 1500 that secure driver 1500 to tensioning device 1400 when key 1200 is in place (see FIG. 12). Cylindrical distal portion 6404 of hub 6402 has formed therein a groove in which elastomeric O-ring 6002 is seated. When O-ring 6002 is assembled to distal portion 6404 of hub 6402 as depicted, the outer diameter of O-ring 6002 is slightly larger than the diameter of proximal cylindrical recess 6504 of handle 6502 of driver 6500. When tensioning device 6400 is assembled to driver 6500 in preparation for use, cylindrical distal portion 6404 of hub 6402 is inserted into proximal cylindrical recess 6504 of handle 6502, O-ring 6002 is compressed by cylindrical recess 6504 thereby creating a friction force therebetween that resists relative movement between handle 6502 and hub 6402. This frictional force allows relative movement between handle 6502 and hub 6402 when sufficient force is applied. In this manner, during insertion or tensioning of suture, driver 6500 is maintained in its position relative to tensioning device 6400 until the surgeon is ready to advance the anchor to the socket and place the anchor. Applying sufficient force to handle 6502 allows the surgeon to rotate and distally advance driver 6500, the frictional resistance to motion being eliminated when handle 6500 has been sufficiently distally advanced so that O-ring 6002 is no longer positioned within cylindrical recess 6504 of handle 6502.

Figure 109:
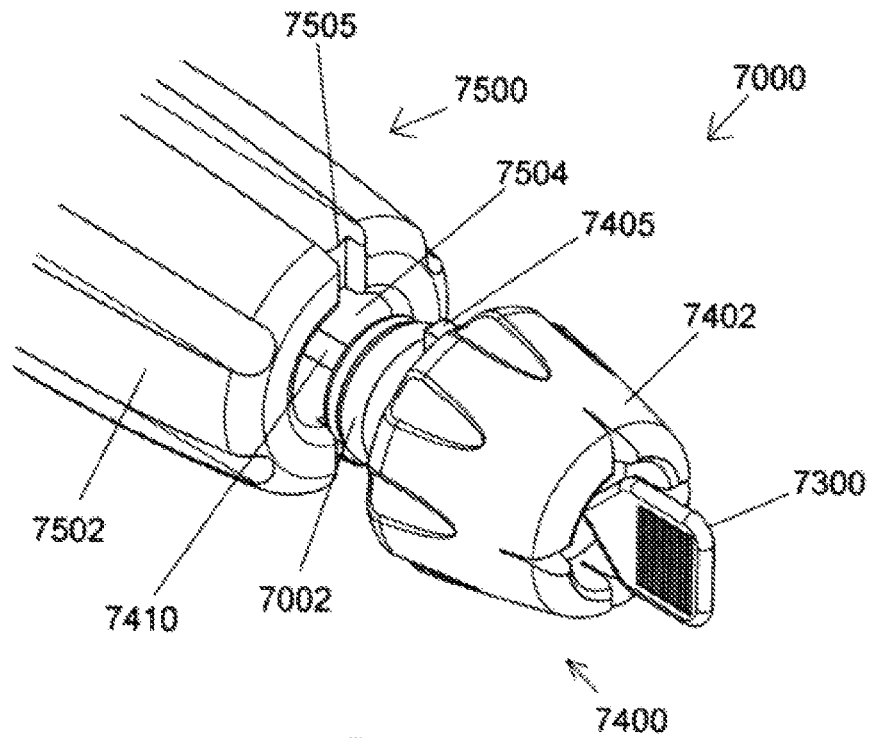
FIG. 109 is a perspective view of the proximal handle portion of another alternate embodiment of the present invention with the tensioning device withdrawn proximally a distance from the driver.
Figure 110:
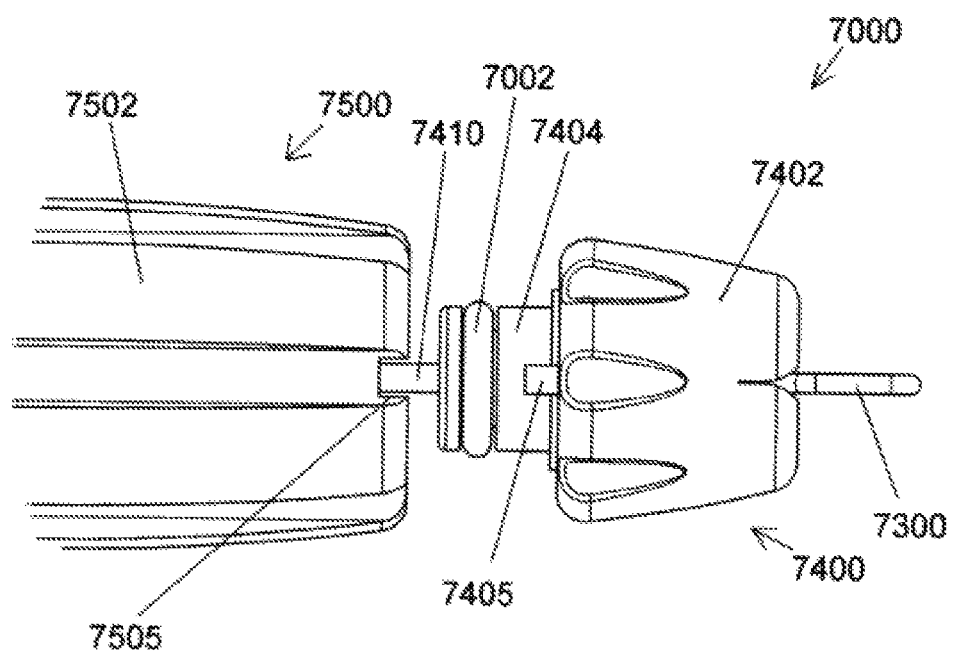
FIG. 110 is a plan view of the objects of FIG. 109.
Figure 111:
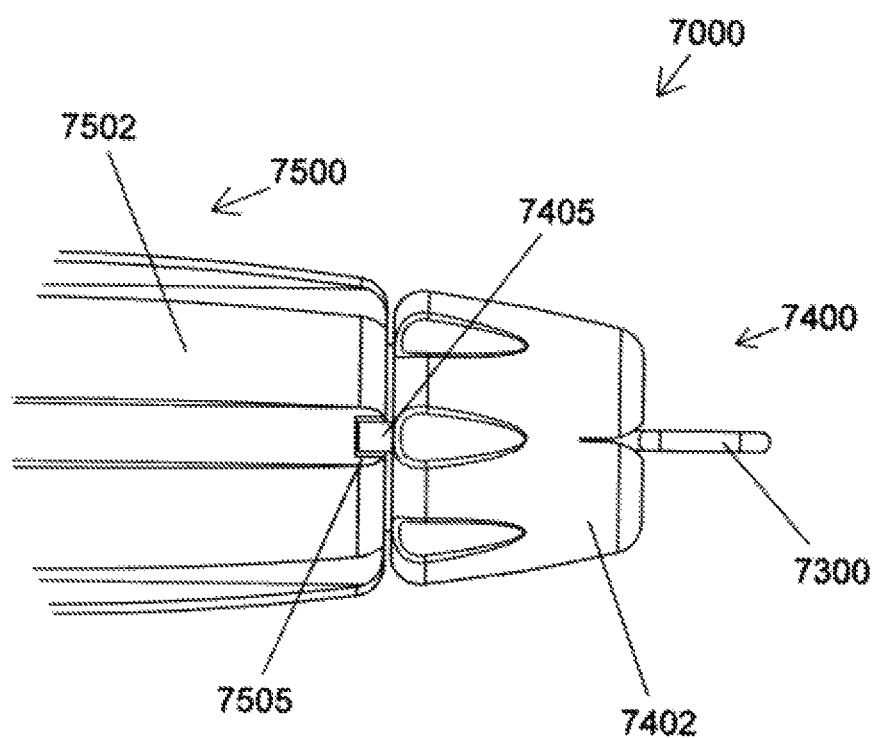
FIG. 111 is a plan view of the objects of FIG. 109 with the tensioning device fully inserted into the driver in preparation for use.

Unlike previous embodiments in which undesired relative motion between the tensioning device and the driver was prevented by a mechanical interlock, system 6000 prevents undesired relative motion by means of a frictional force that may be readily overcome by the surgeon to allow anchor placement without removal of a mechanical interlock. Specifically, system 6000 allows rotation of driver 6500 relative to tensioning device 6400 when tensioning device 6400 is fully inserted into driver 6500. In another embodiment of the present invention depicted in FIGS. 109 through 111, rotation of the driver relative to the tensioning device is prevented when the tensioning device is fully inserted into the driver. Placement system 7000 is identical to system 6000 in all aspects of form and function except as specifically described hereafter. Specifically, handle 7502 has formed in its proximal end channel 7505. Handle 7402 has formed thereon complementary rib 7405. When tensioning device 7400 is fully inserted into driver 7500 rib 7405 is positioned within groove 7505 as depicted in FIG. 111. The mechanical coupling between rib 7405 and channel 7505 prevents rotation of driver 7500 relative to tensioning device 7400 until driver is advanced distally a sufficient distance to disengage rib 7405 from channel 7505.

Figure 117:
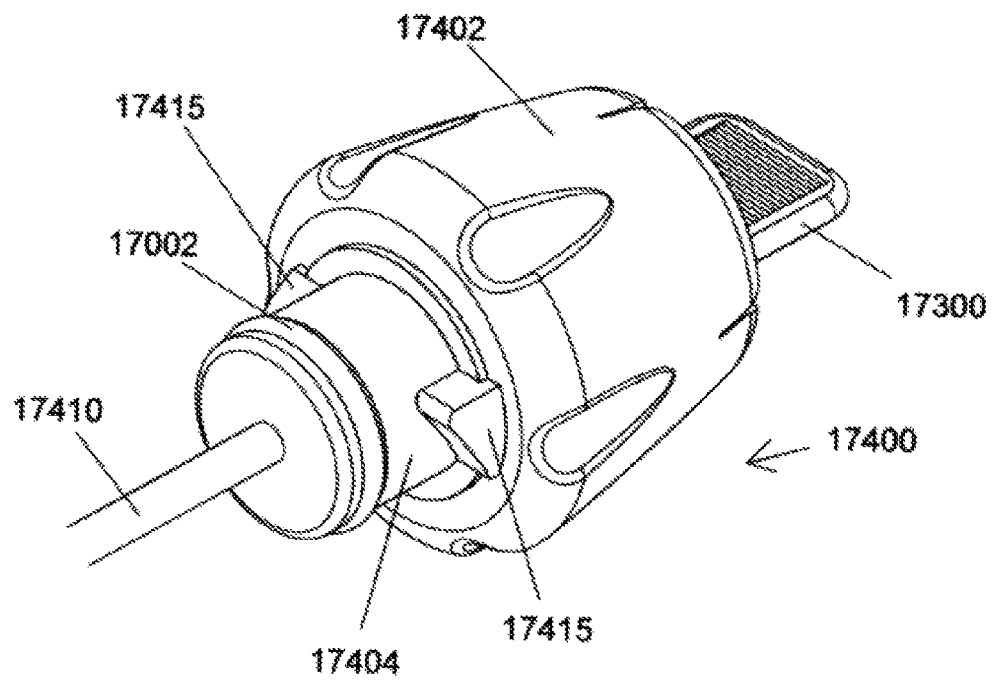
Figure 118:
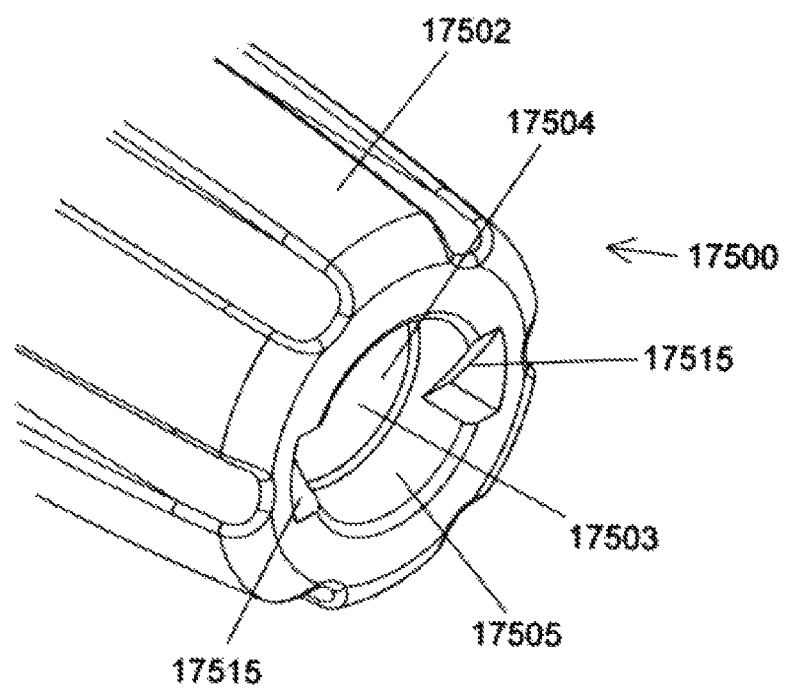

In yet another embodiment of the present invention, rib 7405 of hub 7502 and channel 7505 of hub 7502 are replaced by cams and complementary followers such that rotating the driver handle relative to the tensioning device hub disengages the driver handle from the tensioning hub so as to allow rotational and axial driver motion. Referring now to FIGS. 117 and 118, tensioning device 17400 is identical in all aspects of form and function to tensioning device 7400 except as specifically described hereafter. Driver 17500 is identical in all aspects of form and function to driver 7500 except as specifically described hereafter. In particular, rib 7405 of hub 7400 is eliminated and replaced with cams 17415 on hub 17400. Channel 7505 of handle 7502 is replaced by beveled recesses 17515 complementary to cams 17415 of hub 17400. Proximal cylindrical recess 17504 of driver handle 17502 has a distal portion 17503 and a larger diameter proximal portion 17505. The diameter of distal portion 17503 is such that when cylindrical distal portion 17404 of hub 17402 is positioned within cylindrical recess 17505, O-ring 17002 is compressed by distal portion 17503 of cylindrical proximal recess 17504 so as to create a frictional resistance to axial and rotational motion of driver 17500 relative to tensioning device 17400. In use, tensioning device 17400 is fully inserted into driver 17400 in the manner previously herein described with regard to system 1000 (FIGS. 12 through 19). O-ring 17002 provides a frictional resistance to motion between driver 17500 and tensioning device 17400. Rotating driver handle 17502 relative to hub 17402 causes driver 17500 to be displaced axially due to cooperative interaction between cams 17415 of hub 17402 and beveled recesses 17515 of handle 17502. This axial motion causes O-ring 17002 to move proximally relative to distal portion 17503 of proximal cylindrical recess 17504 until it is fully proximal of portion 17503 whereupon driver 17500 may be freely rotated and moved axially for anchor placement.

Figure 112:
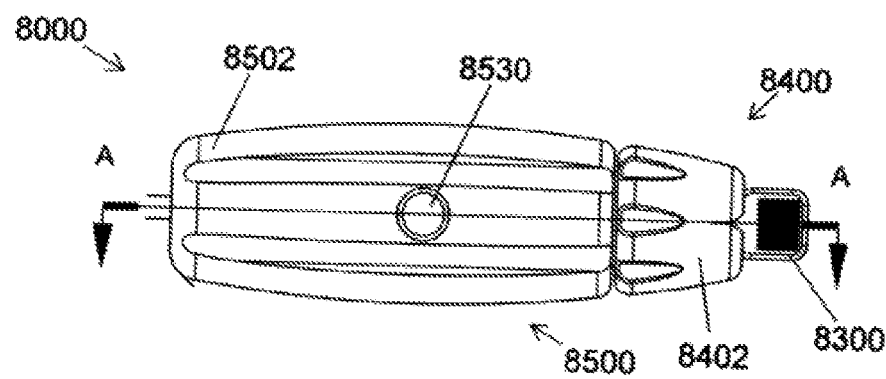
FIG. 112 is a plan view of the handle portion of another alternate embodiment of the present invention.
Figure 113:
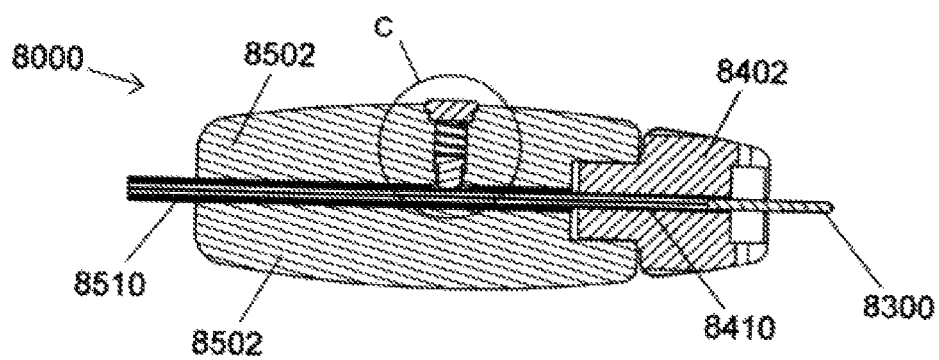
FIG. 113 is a sectional view of the objects of FIG. 112 at location A-A.
Figure 114:
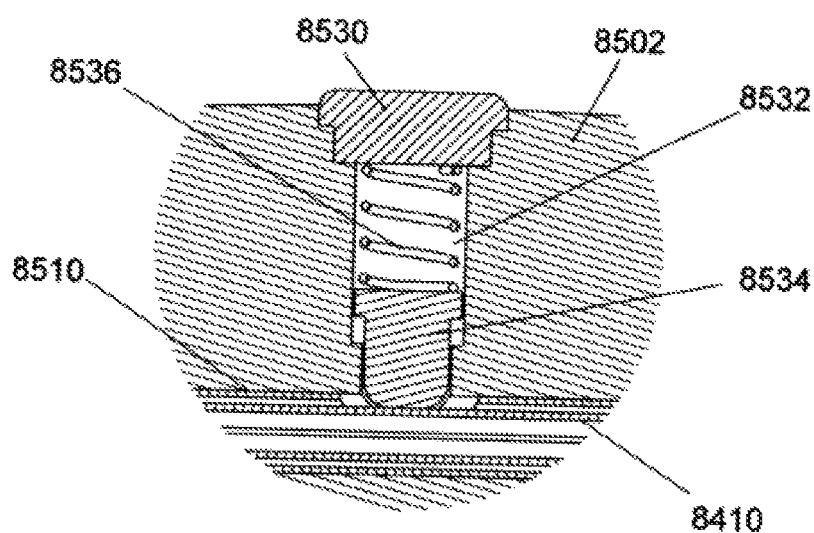
FIG. 114 is an expanded view of the objects of FIG. 113 at location C.

When using systems 6000, 7000 and 17000, frictional resistance to relative motion between the tensioning device and driver is maintained until the driver is advanced a predetermined distance relative to the tensioning device. In other embodiments, the frictional resistance to relative motion is maintained throughout the full range of travel of the driver relative to the tensioning device. An exemplary system 8000 having this full range of travel frictional resistance is depicted in FIGS. 112 through 114. Handle 8502 has formed therein cylindrical recess 8532 wherein is positioned movable element 8534, compression spring 8536 and cap 8530, cap 8530 being affixed to handle 8502 such that spring 8536 applies force to movable element 8534. The insertion of tensioning tubular member 8410 into driver tubular member 8510 causes movable element 8534 to compress spring 8536 so as to create a frictional resistance to relative movement between driver tubular member 8410 and handle 8502. This, in turn, provides frictional resistance to motion between driver 8500 and tensioning device 8400. This resistance extends over the full range of travel of driver 8500 relative to tensioning device 8400.

Other ways of creating this frictional force are contemplated by the present invention, including but not limited to, for example, O-rings or other elastomeric members positioned between elements of driver 8500 and tensioning device 8400, or mechanical interference of metallic or polymeric elements of driver 8500 and tensioning device 8400. Any system that has a non-rotating tensioning device, a driver device positioned coaxially external to the tensioning device, and a means for creating a frictional resistance to relative motion therebetween falls within the scope of this invention.

Figure 115:
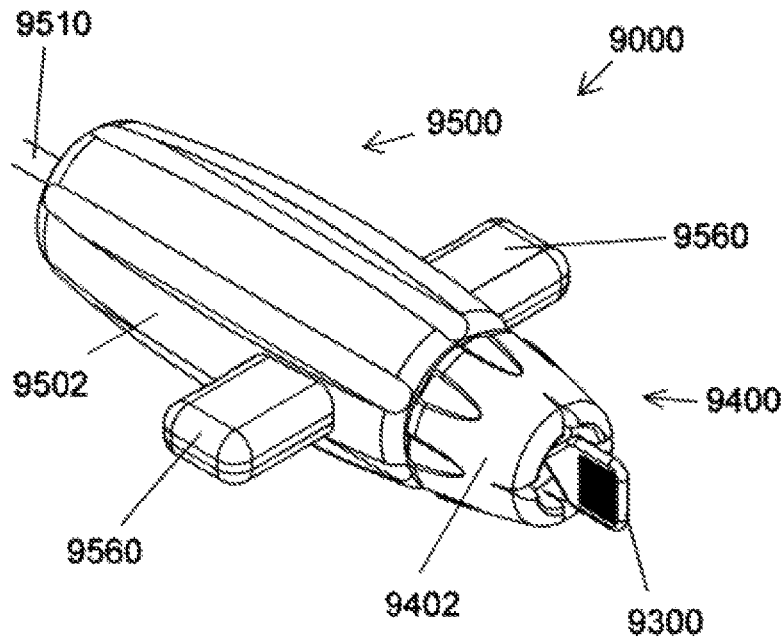
Figure 116:
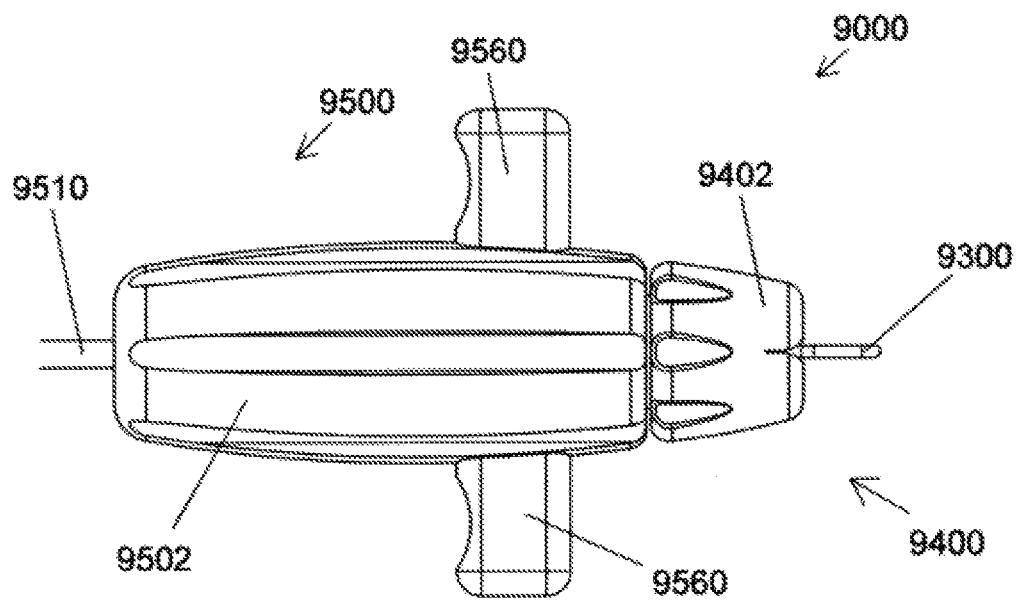

Other embodiments may forego either or both mechanical interlocking of the tensioning device and driver and friction forming means between the devices. In such cases, unintended relative motion between the tensioning device and driver may be prevented by the surgeon. For example, in a preferred embodiment, protrusions formed on the handle of the driver provide grasping surfaces for the surgeon's fingers so that the driver may be retained in a proximal position on the tensioning device until seating of the anchor is required. System 9000 depicted in FIGS. 115 and 116 is identical in all aspects of form and function to system 6000 (FIGS. 107 and 108) except as specifically described below. Specifically, in this embodiment, distal cylindrical portion 9404 (not shown in FIGS. 115 and 116) does not have a groove formed therein for an O-ring, and the O-ring is eliminated. Instead, hub 9502 of driver 9500 has formed thereon laterally opposed protruding portions 9560. Protruding portions 9560 are configured and positioned so that during insertion of the tensioning device distal portion into the socket and positioning of the graft, the surgeon may retain the driver in its proximal position on the tensioning device. The surgeon advances the driver and anchor as in previous embodiments for anchor placement.

It will be understood that while protruding portions 9560 may increase the ease with which driver 9500 is retained in its proximal position by the surgeon, they are not required for operability and thus are considered to be optional. Thus, any anchor system having a cannulated implant, a cannulated driver and a non-rotating tensioning member positioned in the cannula, the tensioning device having a distal portion which extends beyond the implant, wherein the driver is axially and rotationally movable relative to the driver device is within the scope of this invention.

Figure 119:
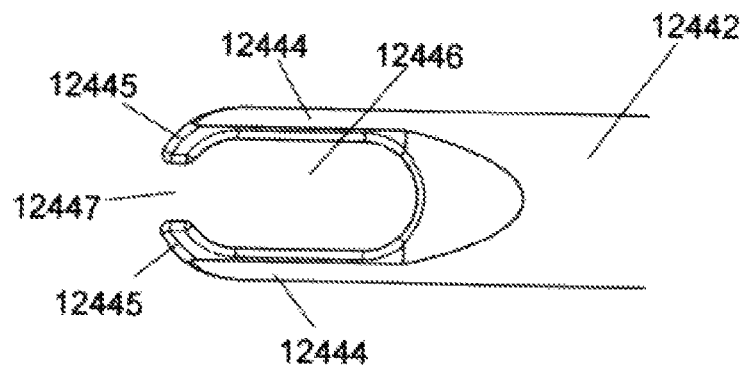
Figure 120:
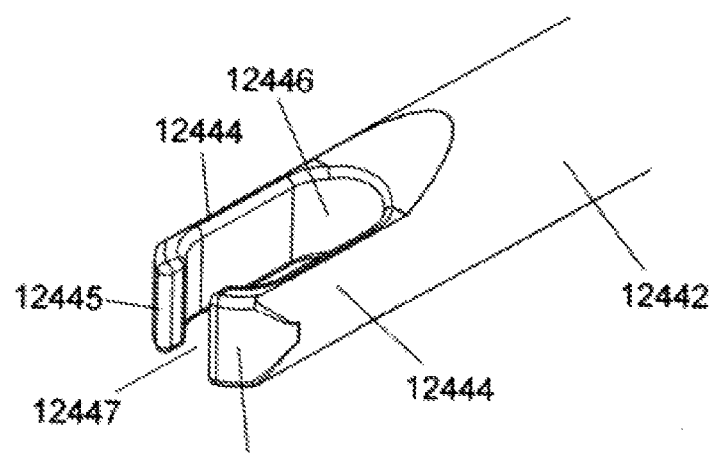
Figure 121:
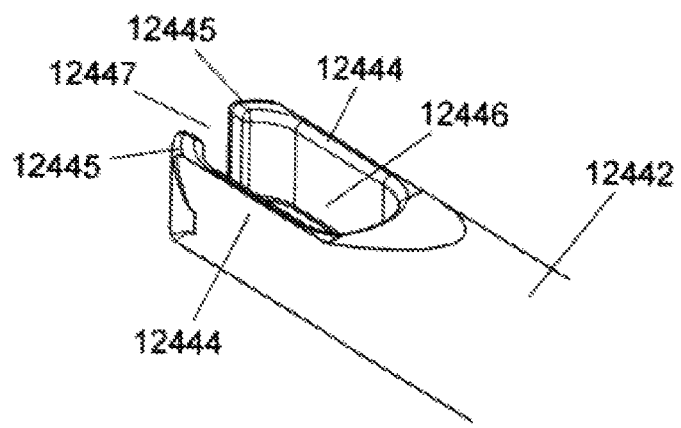

Anchor placement system 2000, depicted in FIGS. 33 through 42, may be used as in FIGS. 43 through 52 wherein sutures are retained within channel 2446 between distally extending portions 2444 of distal element 2442 of tensioning device 2400, or as in FIGS. 53 through 63 wherein distally extending portions 2444 pierce the graft for insertion of the graft into the socket for anchor placement. In other embodiments of the present invention, the distal end of the distal element of the tensioning device is optimized for use in the manner of FIGS. 43 through 52 wherein sutures are retained at the distal end of the tensioning device. For example, FIGS. 119 through 121 depict distal element 12442 that is alike in form and function to distal element 2442 (FIGS. 36 through 40) in all aspects except as specifically subsequently described herein. Specifically, distally extending portions 12444 has distal portions 12445 that extend medially at their distal ends so that channel 12446 formed between distally extending portions 12444 forms an eyelet having a gap 12447 in its distal end. Some current repair techniques for attaching a graft to a boney surface anchor utilize multiple strands of suture with a single implant. Accordingly, it may be desirable to affix as many as six sutures with a single implant. The length of distally extending portions 12444 may thus be extended thereby increasing the size of channel 12446 to accommodate a desired number of suture strands.

Figure 122:
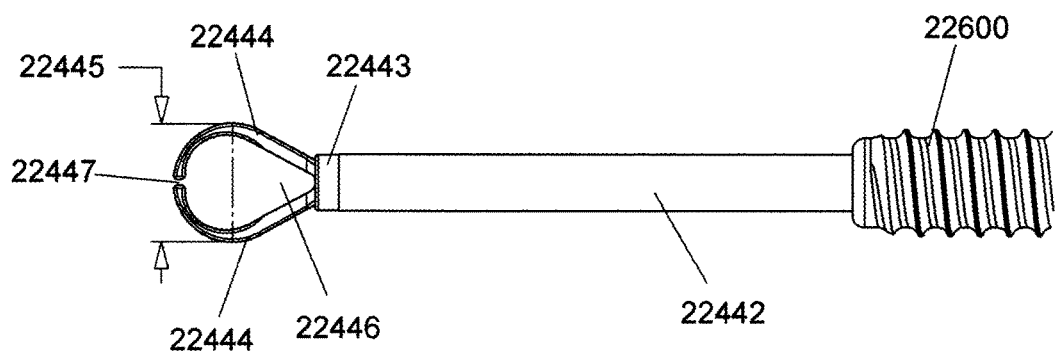
Figure 123:
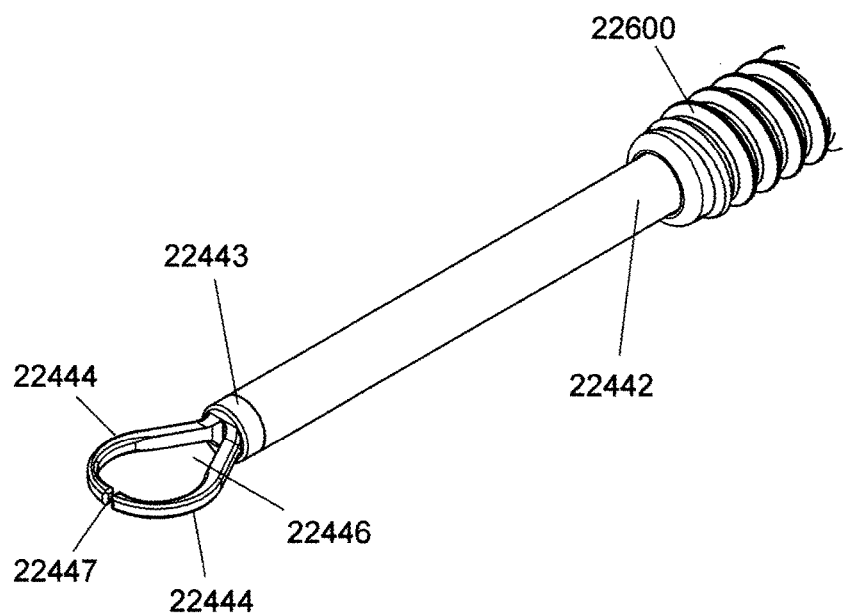
Figure 124:
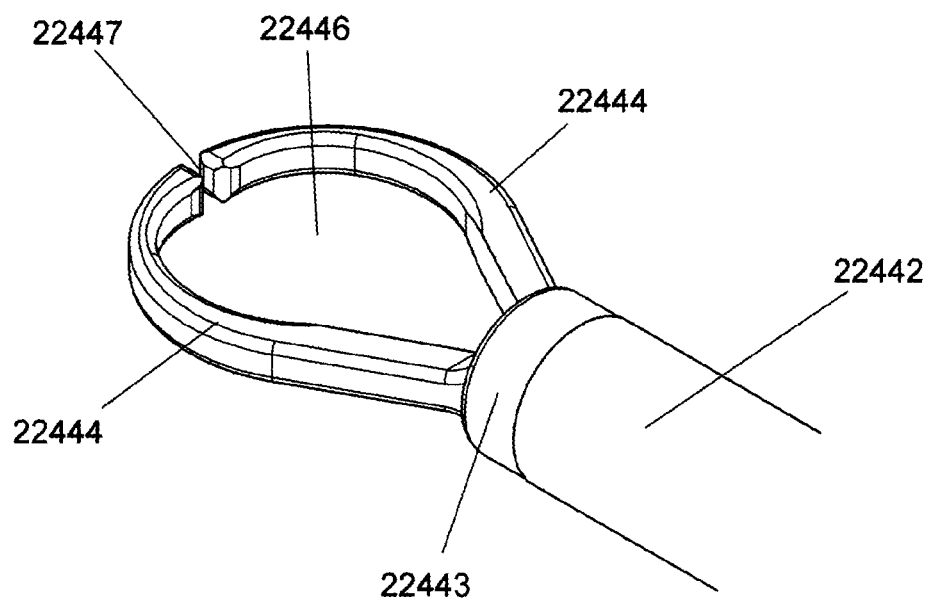

Another alternate embodiment 22000, the distal portion of which is depicted in FIGS. 122 through 124, has a resiliently deformable polymeric distal element 22443 affixed to the distal end of element 22442. Like distally extending portions 12444 of the distal portion of distal element 12442, distally extending portions 22444 of polymeric distal element 22443 are configured for the retention of sutures therebetween, the distal portions of extending portions 22444 curving inward to form a distal gap 22447 between their distal ends, a configuration referred to herein as a "split" suture-capturing loop. Because distally extending portions 22444 are formed of a resiliently deformable preferably polymeric material, the maximum width 22445 across portions 22444 may exceed the diameter of the lumen of implant 22600, with distally extending portions 22444 deforming or bending in an inward direction to allow withdrawal of distal elements 22442 and 22443 from implant 22600 after placement, or for the reinsertion of these elements for implant removal and reinsertion.

In a preferred embodiment, distal element 22443 is formed of PEEK or a similar resilient polymeric material. In other embodiments, distally extending elements 22444 are formed of a super-elastic metallic material such as nitinol. The distally extending portions of the distal end of the distal tensioning element may be rigid, resilient, or elastically deformable, integral with the distal tensioning element or affixed thereto, and formed of a metallic or nonmetallic material. All such variations are contemplated by the present invention.

Figure 126:
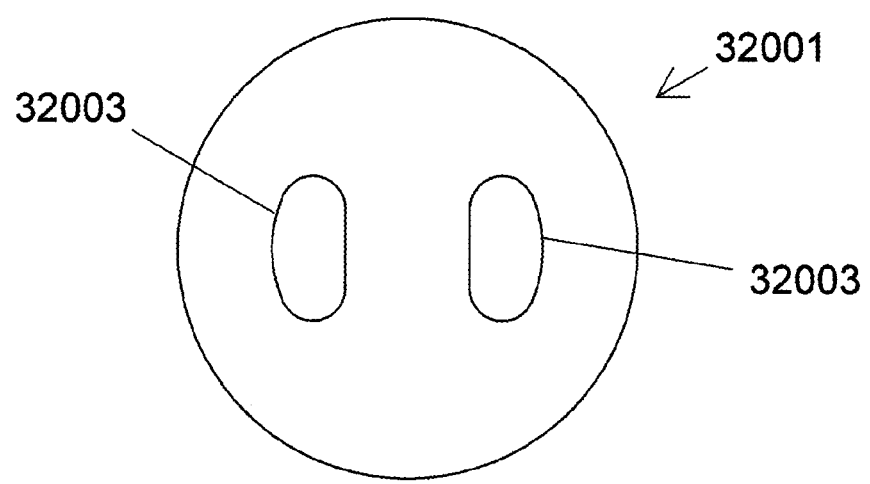

FIGS. 125 and 126 depict a depth-limiting element 32001 formed of a suitable metallic or polymeric material for use with implant placement system 2000 (FIGS. 33 through 42) when used for attachment of a soft tissue graft to bone, for example following a procedure as depicted in FIGS. 53 through 57 and/or FIGS. 58 through 63. Referring now to FIGS. 53 through 57, wherein graft 3020 is impaled on distally extending portions 3444 of distal element 3442 and thereafter inserted into socket 3032 prior to the placement of implant 3600, the force required to insert graft 3020 may be sufficient to cause failure of graft 3020 at the impalement site. Specifically, the distal end of distal element 3442 may excessively penetrate graft 3020 so as to tear graft 3020 such that graft 3020 slides proximally up distal element 3442 rather than being inserted into socket 3032. The depth of penetration of distal element 3442 into graft 3020 may be limited by means of a depth-limiting element. For example, referring to FIGS. 125 and 126, illustrative depth-limiting element 32001 has formed therein slots 32003 configured for removable mounting to distally extending portions 3444 of distal element 3442.

Referring now to FIGS. 127 through 130, the distal portion of alternate embodiment system 32000 is identical in all aspects to system 3000 depicted in FIGS. 53 through 57 and 58 through 63 and in all aspects of form and function except that depth-limiting element 32001 is removably affixed to distally extending portions 32444 of distal element 32442. As described and depicted in co-pending U.S. patent application Ser. No. 15/012,060, in an alternate embodiment placement system 42000, the distal portion of which is depicted in FIGS. 131 and 132, distally extending portions 32444 of placement system 32000 may be replaced by a single distally extending portion 42444 configured for piercing of a soft tissue graft. In this case, the depth-limiting element 42001 may be configured for removable mounting to the distal end of elongate distal element 42442.

Placement system 42000 may be used in the same manner for attaching a graft to a boney surface as system 3000 depicted in FIGS. 53 through 57. The method for fixation of graft 3020 to boney surface 3030 is alike in all aspects of form and function except as specifically herein described; an illustrative method is depicted in FIGS. 133 through 137. With reference thereto, socket 3032 is formed in boney surface 3030 in a predetermined location. Depth-limiting element 42001 is then removably affixed to the distal end of elongate distal portion 42442 of placement system 42000. As depicted in FIGS. 133 through 137, whip stitches 3021 may be placed in the distal portion of graft 3020. Whip stitches 3021 are optionally added to increase the resistance of the completed construct to failure due to tensile load but are not considered a required element of forming a construct in accordance with the principles of the present invention.

Graft 3020 is impaled on the distally extending portion 42444 of distal element 42442 as shown in FIGS. 133 and 134, with depth-limiting element 42001 limiting the depth of penetration of distally extending portion 42444 into graft 3020. Thereafter, distal element 42444 is inserted into socket 3032 as shown in FIG. 135 with depth-limiting element 42001 preventing additional penetration of graft 3032 due to the force applied during insertion. Anchor 42600 is placed as depicted in FIG. 136 trapping graft 3020 between anchor 42600 and the boney surface of the wall of socket 3032. Friction force between the inserted portion of graft 3020 and socket 3032 maintains the position of graft 3020 relative to socket 3032 and bone 3030. Optional whip stitches 3021 increase the resistance to movement of graft 3020 relative to socket 3032 when a tension force is applied to graft 3020. FIG. 137 depicts the site at completion of the anchor placement and removal of insertion system 42000. Depth-limiting element 42001 remains in the construct adjacent to the distal end of implant 42600, between implant 42600 and graft 3020.

An alternative method for affixing a soft tissue graft to a boney surface using placement system 42000 is like the placement method depicted in FIGS. 58 through 63 in all aspects of form and function except as specifically described below; an illustrative example is depicted in FIGS. 138 through 143. With reference thereto depth-limiting element 42001 is removably affixed to the distal end of elongate distal portion 42442 of placement system 42000. As depicted in FIGS. 133 through 137, optional whip stitches 3021 may be formed in the distal portion of graft 3020. As noted above, whip stitches 3021 are optionally added to increase the resistance of the completed construct to failure due to tensile load but are not considered a required element of forming a construct in accordance with the principles of the present invention.

A preferred method of affixing graft 3020 to boney surface 3030 thereafter has the following steps: Socket 3032 is formed in boney surface 3030 at a predetermined location. Graft 3020 is then impaled on the sharpened distally extending portion 42444 of distal element 42442 as shown in FIGS. 138 and 139, wherein the sharpened distal end of distally extending portion 42444 penetrates the graft but the depth of penetration is limited by depth-limiting element 42001. The site for penetration is selected such that when the distal portion of graft 3020 is inserted to the bottom of socket 3032 the distal end of graft 3020 protrudes above the rim of socket 3032. As seen in FIG. 140, graft 3020 is positioned above socket 3032 and inserted as shown in FIG. 141. Depth-limiting element 42001 prevents penetration of graft 3020 by distal element 42442 during insertion due to the insertion force applied. Thereafter, anchor 42600 placed as shown in FIG. 142. FIG. 143 shows the completed repair. Graft 3020 is then trapped between the exterior surface of anchor 3600 and first and second laterally opposed portions of the wall of socket 3032 and retained in position by friction therefrom. Depth limiting element 42001 remains in the construct adjacent to the distal end of implant 42600, between implant 42600 and graft 3020.

Affixing soft tissue graft 3020 to boney surface 3030 may optionally include the step of providing a force indicating anchor system 4000 of the instant invention (such as depicted in FIGS. 80 through 84) so as to allow the tension in graft 3020 after fixation to have a measured predetermined value. When affixing graft 3020 using force indicating anchor system 4000, graft 3020 is impaled on distal portion 42444 as depicted in FIG. 139, moved into position as depicted in FIG. 140 and inserted to the bottom of socket 3032 as depicted in FIG. 141. The force required for insertion, equal to the tensile force in graft 3020, is determined as previously described herein and the observed value compared to the predetermined value desired. If the force is higher than the predetermined value, the graft is returned to the state as depicted in FIG. 139 and the site for penetration by distally extending portion 42444 is moved distally, and if lower than the predetermined value, moved proximally. Thereafter, the graft is moved into position as depicted in FIG. 140 and inserted as in FIG. 141. The force of insertion (graft tensile force) may be observed and again compared to the predetermined value and the penetration site may be adjusted accordingly until the desired insertion force is attained. Thereafter, implant 42600 may be placed as previously described.

INDUSTRIAL APPLICABILITY

As noted previously, there is a need in the art for simplified placement systems and methods for tissue graft anchors by which the surgeon may introduce one or more sutures into a prepared socket in the boney tissue, apply tension to the suture(s) to advance a soft tissue graft to a desired location, and then advance an anchor into the bone, all while maintaining suture tension. The present invention addresses this need by providing a system and method for the placement of an implant, especially a suture anchor, threaded, knotless or otherwise, that allows the surgeon to establish the graft position and, while maintaining that position, secure the anchor without changing the suture tension or causing a shift in the graft position and furthermore, when the anchor is threaded, without spinning of the suture. The present invention also provides off-axis socket drills and implant driving devices that enable implantation in remote and difficult to access boney surfaces using minimally invasive procedures. The present invention further provides specially configured distal end designs, including, for example, a resiliently deformable polymeric distal element that allows for the retention of multiple sutures and/or a depth or penetration-limiting element formed of a suitable metallic or polymeric material that serves to prevent the distal end of the device from excessively penetrating, damaging or tearing a tissue graft of interest. Although described in detail with respect to ligament repairs, such as repair of a torn rotator cuff, it will be readily apparent to the skilled artisan that the utility of the present invention extends to other tissues and injuries.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An implant placement system for affixing a soft tissue graft to a prepared socket in a boney surface via an anchoring implant, said system comprising:
   a. a cannulated driver device comprising a proximal handle portion having an open proximal end and an elongate tubular distal portion that defines the longitudinal axis of the system and includes an open distal end that is configured to receive said anchoring implant, wherein at least one lumen extends from said proximal to distal end; and
   b. an elongate insertion device that is configured to be slidably received within said at least one lumen of said cannulated driver device and that comprises a proximal portion, an elongate rigid medial portion and a distal portion,
      wherein, when said anchoring implant is coupled to the open distal end of said cannulated driver device and said elongate insertion device is slidably received within said at least one lumen of said cannulated driver device, at least the distal portion of said elongate insertion device extends distally past a distal end of said anchoring implant;
      further wherein said distal portion of said elongate insertion device comprises either (a) two or more distally extending elements that together define a channel that is configured for and capable of receiving and retaining the first ends of one or more elongate sutures or (b) one or more sharp-tipped distally extending elements designed to pierce and thereby receive and retain at least one end of said soft tissue graft and
      further wherein the proximal handle portion of said cannulated driver device may be releasably engaged to and disengaged from the proximal hub element of said elongate insertion device, such that (a) when said proximal handle portion and said proximal hub element are engaged, relative rotational and axial movement between said cannulated driver device and said elongate insertion device is precluded and (b) when said proximal handle portion and said proximal hub element are disengaged, relative rotational and axial movement between said cannulated driver device and said elongate insertion device is enabled.

2. The implant placement system of claim 1, wherein said distal portion of said elongate insertion device comprises a pair of opposed, distally extending elements that curve inward, towards each other at their respective distal ends so as to define a split suture-capturing loop.

3. The implant placement system of claim 2, wherein a maximum width of said split suture-capturing loop is greater than a maximum diameter of said at least one lumen of said cannulated driver device.

4. The implant placement system of claim 3, wherein said opposed, distally extending elements are formed of a resiliently deformable material.

5. The implant placement system of claim 4, wherein said resiliently deformable material is a polymeric material selected from the group consisting of polyetheretherketone (PEEK), carbon fiber reinforced PEEK (PEEK CF), and polylactic acid (PLA).

6. The implant placement system of claim 3, wherein opposed, distally extending elements are formed of a shape memory material.

7. The implant placement system of claim 6, wherein said shape memory material is a superelastic metal alloy of nickel and titanium.

8. The implant placement system of claim 1, wherein said distal portion of said elongate insertion device comprises two or more sharp-tipped tines disposed in relative parallel that are designed to pierce at least one end of said soft tissue graft, wherein said distal portion further comprises a depth-limiting element that is axially slidable over said tines and removably mountable to said distal portion.

9. The implant placement system of claim 8, wherein said depth-limiting element comprises a relatively thin disk having two or more transverse slots configured to receive said two or more sharp-tipped tines.

10. The implant placement system of claim 1, wherein said distal portion of said elongate insertion device comprises a single conical element designed to pierce and thereby receive and retain at least one end of said soft tissue graft, wherein said distal portion further comprises a depth-limiting element that is axially slidable over said conical element and removably mountable to said distal portion.

11. The implant placement system of claim 10, wherein said depth-limiting element comprises a relatively thin annular disk having a single centrally disposed opening configured to receive said single conical element.

12. The implant placement system of claim 1, wherein the proximal portion of said elongate insertion device includes a hub element.

13. The implant placement system of claim 1, wherein said anchoring implant comprises a threaded anchor.

14. The implant placement system of claim 1, wherein said anchoring implant comprises a cannulated interference plug-type anchor.

15. The implant placement system of claim 1, wherein the distal end of said cannulated driver device and a proximal end of said anchoring implant are provided with mating features that enable secure attachment of said anchoring implant to said cannulated driver device.

16. The implant placement system of claim 15, wherein the distal end of said cannulated driver device includes torque transmitting features that, together with complementary torque receiving features formed in a proximal portion of the anchoring implant, allow the transmission of torque to said anchoring implant necessary to drive said anchoring implant into said prepared socket.

17. The implant placement system of claim 1, wherein the proximal handle portion of said cannulated driver device and the proximal hub portion of said elongate insertion device are provided with complementary mating features that enable secure engagement.

18. The implant placement system of claim 17, wherein said complementary mating features comprise (a) one or more off-axis lateral hole(s) disposed near the proximal end of the proximal handle portion of said cannulated driver device and (b) one or more off-axis lateral groove(s) disposed near the distal end of the proximal hub portion of said elongate insertion device, wherein said placement system further comprises a key element comprised of a proximal portion having one or more cylindrical projections extending therefrom, whereby said cylindrical projection(s) extend through said off-axis lateral hole(s) and engage said off-axis lateral groove(s) to lock said elongate insertion device to said cannulated driver device and preclude relative rotational and axial movement therebetween.

19. A method for affixing a soft tissue graft to a target boney surface, the method comprising the steps of:

a. providing the implant placement system of claim 1, wherein the distal portion of the elongate insertion device comprises a pair of opposed, distally extending elements that curve inward, towards each other at their respective distal ends so as to define a split suture-capturing loop;
b. positioning an anchoring implant comprising a cannulated knotless suture anchor onto the distal end of said cannulated driver device;
c. providing one or more elongate sutures, each of which has a first free end and a second end attached to said soft tissue graft;
d. threading said first free ends through the split suture capturing loop that extends out of and distally past the open distal end of said elongate insertion device;
e. inserting the distal end of the elongate insertion device into a suitably configured socket disposed in said target boney surface;
f. applying tension to the one or more elongate sutures to draw the soft tissue graft to a desired position;
g. distally advancing said cannulated driver device so as to drive said anchoring implant in the socket, whereby said anchoring implant serves to anchor said soft tissue graft to said target boney surface.

20. The method of claim 19, wherein the proximal portion of said elongate insertion device includes a hub element.

21. The method of claim 20, wherein, prior to insertion step (e), a proximal end of the proximal handle portion of said cannulated driver device is engaged to a distal end of the proximal hub element of said elongate insertion device so as to preclude relative rotational and axial movement between said driver device and insertion device.

22. The method of claim 19, further comprising step (h) of withdrawing the components of the implant placement system after step (g).

23. The method of claim 22, further comprising step (i) of trimming the free end(s) of said one or more elongate sutures after step (h).

24. The method of claim 19, further comprising repeating steps (b) through (g) as required.

25. A method for affixing an elongate soft tissue graft to a target boney surface, the method comprising the steps of:

a. providing the implant placement system of claim 1, wherein the distal portion of the elongate insertion devices comprises one or more sharp-tipped distally extending elements designed to pierce and thereby receive and retain at least a portion of said elongate soft tissue graft;
b. positioning an anchoring implant on the distal end of said cannulated driver device;
c. piercing and releasably retaining a proximal portion of said elongate soft tissue graft with said one or more sharp-tipped distally extending elements that comprise the distal portion of said elongate insertion device so as to allow positioning of said proximal portion of said elongate soft tissue graft;
d. drawing said proximal portion of said elongate soft tissue graft to a suitably configured socket disposed in said target boney surface;
e. inserting the distal portion of said elongate insertion device and said proximal portion of said elongate soft tissue graft retained thereto into said socket; and
f. distally advancing said cannulated driver device so as to drive the anchoring implant in the socket, whereby said anchoring implant serves to anchor said elongate soft tissue graft to said target boney surface.

26. The method of claim 25, wherein the proximal portion of said elongate insertion device includes a hub element.

27. The method of claim 26, wherein, prior to insertion step (e), a proximal end of the proximal handle portion of said cannulated driver device is engaged to a distal end of the proximal hub element of said elongate insertion device so as to preclude relative rotational and axial movement between said driver device and insertion device.

28. The method of claim 25, wherein the anchoring of step (f) is performed in the absence of one or more sutures.

29. The method of claim 25 wherein said distal portion of said elongate insertion device comprises two or more sharp-tipped tines disposed in relative parallel that are designed to pierce at least one end of said soft tissue graft, wherein said distal portion further comprises a depth-limiting element that is axially slid over said tines and removably mounted to said distal portion.

30. The implant placement system of claim 29, wherein said depth-limiting element comprises a relatively thin disk having two or more transverse slots configured to receive said two or more sharp-tipped tines.

31. The implant placement system of claim 25, wherein said distal portion of said elongate insertion device comprises a single conical element designed to pierce and thereby receive and retain at least one end of said soft tissue graft, wherein said distal portion further comprises a depth-limiting element that is axially slid over said conical element and removably mounted to said distal portion.

32. The implant placement system of claim 31, wherein said depth-limiting element comprises a relatively thin annular disk having a single centrally disposed opening configured to receive said single conical element.

\* \* \* \* \*